(12) United States Patent
Ferrara et al.

(10) Patent No.: US 8,858,936 B2
(45) Date of Patent: *Oct. 14, 2014

(54) COMPOSITIONS WITH HEMATOPOIETIC AND IMMUNE ACTIVITY

(75) Inventors: Napoleone Ferrara, San Francisco, CA (US); Jennifer LeCouter, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/566,920

(22) Filed: Aug. 3, 2012

(65) Prior Publication Data

US 2013/0195885 A1 Aug. 1, 2013

Related U.S. Application Data

(60) Continuation of application No. 12/611,397, filed on Nov. 3, 2009, now Pat. No. 8,257,702, which is a division of application No. 10/549,241, filed as application No. PCT/US2004/007622 on Mar. 12, 2004, now Pat. No. 7,632,810.

(60) Provisional application No. 60/454,462, filed on Mar. 12, 2003, provisional application No. 60/511,390, filed on Oct. 14, 2003.

(51) Int. Cl.
| | | |
|---|---|---|
| A61K 39/00 | (2006.01) | |
| A61K 39/395 | (2006.01) | |
| A61K 38/18 | (2006.01) | |
| A61K 38/02 | (2006.01) | |
| C12N 5/077 | (2010.01) | |

(52) U.S. Cl.
CPC ......... *A61K 39/3955* (2013.01); *A61K 38/1866* (2013.01); *A61K 38/02* (2013.01); *C12N 5/0673* (2013.01); *A61K 38/1891* (2013.01)
USPC .................. 424/130.1; 424/133.1; 424/141.1; 424/142.1; 424/145.1; 514/1.1; 514/7.9

(58) Field of Classification Search
CPC .............. A61K 39/3955; A61K 38/02; A61K 38/1866; A61K 38/1891; C12N 5/0673
See application file for complete search history.

(56) References Cited

U.S. PATENT DOCUMENTS

| | | | |
|---|---|---|---|
| 5,240,848 A | 8/1993 | Keck et al. | |
| 5,332,671 A | 7/1994 | Ferrara et al. | |
| 6,020,473 A | 2/2000 | Keyt et al. | |
| 6,485,938 B1 | 11/2002 | Sheppard et al. | |
| 6,828,425 B2 | 12/2004 | Sheppard et al. | |
| 7,060,278 B2 | 6/2006 | Ferrara et al. | |
| 7,264,801 B2 | 9/2007 | Ferrara et al. | |
| 7,632,810 B2 | 12/2009 | Ferrara et al. | |
| 8,257,702 B2 | 9/2012 | Ferrara et al. | |
| 2002/0115610 A1 | 8/2002 | Zhou et al. | |
| 2003/0027998 A1 | 2/2003 | Holtzman et al. | |
| 2003/0171306 A1 | 9/2003 | Davis et al. | |
| 2004/0156842 A1 | 8/2004 | Thompson et al. | |
| 2010/0316633 A1 | 12/2010 | Ferrara et al. | |

FOREIGN PATENT DOCUMENTS

| | | |
|---|---|---|
| WO | WO 97/08313 | 3/1997 |
| WO | WO 98/10071 | 3/1998 |
| WO | WO 99/06550 | 2/1999 |
| WO | WO 99/63088 | 12/1999 |
| WO | WO 00/52022 | 9/2000 |
| WO | WO 00/53753 | 9/2000 |
| WO | WO 00/63380 | 10/2000 |
| WO | WO 00/70049 | 11/2000 |
| WO | WO 00/73454 | 12/2000 |
| WO | WO 00/75327 | 12/2000 |
| WO | WO 01/36465 | 5/2001 |
| WO | WO 01/40466 | 6/2001 |
| WO | WO 01/93983 | 12/2001 |
| WO | WO 02/00690 | 1/2002 |
| WO | WO 02/00711 | 1/2002 |
| WO | WO 02/08284 | 1/2002 |
| WO | WO 02/08288 | 1/2002 |
| WO | WO 02/36625 | 5/2002 |
| WO | WO 03/020892 | 3/2003 |

OTHER PUBLICATIONS

Bellamy WT, 2002, "Vascular endothelial growth factor as a target opportunity in hematological malignancies". Curr Opin Oncol. 14(6):649-56.
Cheng et al., 2002, "Prokineticin 2 transmits the behavioural circadian rhythm of the suprachiasmatic nucleus." Nature 417:405-410.
Gerber & Ferrara, 2003, "The role of VEGF in normal and neoplastic hematopoiesis." J Mol. Med 81:20-31.
Gerber et al., 2002, VEGF regulates haematopoietic stem cell survival by an internal autocrine loop mechanism. Nature. 417(6892):954-8.
Glinka et al., 1998, "Dickkopf-1 is a member of a new family of secreted proteins and functions in head induction." Nature 391:357-362.
Janowska-Wieczorek et al., 2001, "Autocrine/Paracrine Mechanisms in Human Hematopoiesis." Stem Cells 19:99-107.
Joubert & Strydom, 1980, Hopper-Seler's Z. Physiol Chem. 361:1787-1794.
Ju et al., 1991, "Conversion of the interleukin 1 receptor antagonist into an agonist by site-specific mutagenesis." Proc Natl Acad Sci 88(7):2658-62.
Kaser et al., 2003,. "The AVIT protein family. Secreted cysteine-rich vertebrate proteins with diverse functions." Embo Reports 4:469-473.
Keck et al., 1989, "Vascular permeability factor, an endothelial cell mitogen related to PDGF." Science 246:1309-1312.

(Continued)

*Primary Examiner* — Daniel C Gamett
(74) *Attorney, Agent, or Firm* — Jones Day

(57) ABSTRACT

The present invention provides methods of using Bv8 and EG-VEGF polypeptides and nucleic acids to promote hematopoiesis. Also provided herein are methods of screening for modulators of Bv8 and EG-VEGF activity. Furthermore, methods of treatment using Bv8 and EG-VEGF polypeptides or Bv8 and EG-VEGF antagonists are provided.

18 Claims, 29 Drawing Sheets

(56) References Cited

OTHER PUBLICATIONS

Kisliouk et al., 2005, "Prokineticins (endocrine gland-derived vascular endothelial growth factor and BV8) in the bovine ovary: expression and role as mitogens and survival factors for corpus luteum-derived endothelial cells." Endocrin. 146:3950-3958.

Kruse et al., 1992, "Conversion of human interleukin-4 into a high affinity antagonist by a single amino acid replacement." Embo J 11(9):3237-44.

LeCouter et al., 2001, "Identification of an angiogenic mitogen slectrive for endocrine gland endothelium." Nature 412(6850):877-884.

LeCouter et al., 2002, "Endocrine gland-derived VEGF and the emerging hypothesis of organ-specific regulation of angiogenesis." Nat. Med 8(9):913-917.

LeCouter et al., 2003, "Mouse endocrine gland-derived vascular endothelial growth factor: a distinct expression pattern from its human ortholog suggests different roles as a regulator of organ-specific angiogenesis" Endocrin. 144:2606-2616.

LeCouter et al., 2003, "The endocrine-gland-derived VEGF homologue Bv8, promotes angiogenesis in the testis: Localization of Bv8 receptors to endothelial cells." Proc. Natl. Acad. Sci. 100:2685-2690.

Leung et al., 1989, "Vascular endothelial growth factor is a secreted angiogenic mitogen." Science 246:1306-1309.

Li et al., 2001, "Identification of two prokineticin cDNAs: recombinant proteins potently contract gastrointestinal smooth muscle." Mol. Pharmacol. 59:692-698.

Lin et al, 2002, "Identification and molecular characterization of two closely related G protein-coupled receptors activated by prokineticins/endocrine gland vascular endothelial growth factor." J biol. Chem. 277:19276-19280.

Masuda et al., 2002, "Isolation and identification of EG-VEGF/prokineticins ascognate ligands for two orphan G-protein=coupled receptors." Biochem Biopyhys Res. Commun. 293:396-402.

Melchiorri et al., 2001, "The mammalian homologue of the novel peptide Bv8 is expressed in the central nervous system and supports neuronal survival by activating the MAP kinase/PI-3-kinase pathways." Eur. J Neurosci 13:1694-1702.

Mollay et al., 1999, "Bv8, a small protein from frog skin and its homologue from snake venom induce hyperalgesia in rats,." Eur J. Pharmacol. 374:189-196.

Negri et al., 2005, "Biological activities of Bv8 analogues." Brit J. Pharmacol. 146:625-632.

Schweitz et al., 1999, "MIT(1), a black mamba toxin with a new and highly potent activity on intestinal contraction." FEBS Lettts 461:183-188.

Wechselberger et al., 1999, "The mammalian homologues of frog Bv8 are mainly expressed in spermatocytes." FEBS Lett 462(1-2):177-181.

International Search Report and Written Opinion dated Sep. 14, 2004 for PCT Application No. PCT/US04/07622, filed Mar. 12, 2004.

FIG. 1

```
1    tgagggcgcc atgaggagcc tgtgctgcgc cccactcctg ctcctcttgc tgctgccgcc
61   gctgctgctc acgccccgcg ctgggacgc ctgggacgc cgccgtgatc acggggctt gtgacaagga
121  ctcccaatgt ggtggaggca tgtgctgtgc tgtcagtatc tgggtcaaga gcataaggat
181  ttgcacacct atgggcaaac tgggagacag ctgccatcca ctgactcgta aaaacaattt
241  tggaaatgga aggcaggaaa gaagaaagag gaagagaagc aaaaggaaaa aggaggttcc
301  attttttggg cggaggatgc atcacacttg cccatgtctg ccaggcttgg cctgtttacg
361  gacttcattt aacgattta tttgttttagc ccaaaagtaa tcgctctgga gtagaaacca
421  aatgtga
```

FIG. 2

MRSLCCAPLLLLLLLPPLLLTPRAGDAAVITGACDKDSQCGGMCCAVSIWVKSIRICT
PMGKLGDSCHPLTRKNNFGNGRQERRKRKRSKRKKEVPFFGRRMHHTCPCLPGLACLRT
SFNRFICLAQK

FIG. 3

```
  1  tgagggcgcc atgaggagcc tgtgctgcgc cccactcctg ctcctcttgc tgctgccgcc
 61  gagggcgcca tgaggagcct gtgctgcgcc ccactcctgc tcctcttgct gctgccgccg
121  ctgctgctca cgccccgcgc tgggacgcc tggtgtgct gccgtgatca ccgggcttg tgacaaggac
181  tcccaatgtg gtggaggcat gtgctgtgct gtcagtatct gggtcaagag cataaggatt
241  tgcacaccta tgggcaaact gggagacagc tgccatccac tgactcgtaa agttccattt
301  tttgggcgga ggatgcatca cacttgccca tgtctgccag gcttggcctg tttacggact
361  tcatttaacc gatttatttg tttagcccaa aagtaatcgc tctggagtag aaaccaaatg
421  tga
```

FIG. 4

MRSLCCAPLILLLLLLPPLLLTPRAGDAAVITGACDKDSQCGGGMCCAVSIWVKSIRICT
PMGKLGDSCHPLTRKVPFFGRRMHHTCPCLPGLACLRTSFNRFICLAQK

FIG. 5

```
   1  cgacgcgtg ggcgtccct aaccgccacc gcgtccccgg gacgccatgg gggacccgcg
  61  ctgtccccg ctactgctac ttctgctgct acgcgctgct ttcacaccgc ccgccgggga
 121  tgccgcggtc atcaccgggg cttgcgacaa ggactctcag tgccggagag gcatgtgctg
 181  tgctgtcagt atctgggtta agagcataag gatctgcaca cctatgggcc aagtgggcga
 241  cagctgccac cccctgactc ggaaagttcc attttggggg cggaggatgc accacactg
 301  cccctgcctg ccaggcttgg cgtgtttaag gacttctttc aaccggttta tttgcttgc
 361  ccggaaatga tcactctgaa gtaggaactt gaaatgcgac cctccgctgc acaatgtccg
 421  tcgagtctca cttgtaattg tggcaaacaa agaatactcc agaaagaaat gttctccccc
 481  ttccttgact ttccaagtaa cgtttctatc tttgatttt gaagtggctt tttttttttt
 541  tttttttcc tttccttgaa ggaaagtttt gatttttgga gagatttata gaggactttc
 601  tgacatggct tctcatttcc ctgtttatgt tttgccttga catttttgaa tgccaataac
 661  aactgttttc acaaatagga gaataagagg gaacaatctg ttgcagaaac ttccttttgc
 721  cctttgcccc actcgccccg cccgccccg cccgccctg cccatgcgca gacagacaca
 781  cccttactct tcaaagactc tgatgatcct caccttactg tagcattgtg ggtttctaca
 841  cttcccccgcc ttgctggtgg accactgag gaggctcaga gagctagcac tgtacaggtt
 901  tgaaccagat cccccaagca gctcatttgg ggcagacgtt gggagcgctc caggaacttt
 961  cctgcaccca tctgcccac tggcttttcag ttctgctgtt taactggtgg gaggacaaaa
1021  ttaacgggac cctgaaggaa cctggcccgt ttatctagat ttgtttaagt aaaagacatt
1081  ttctcccttgt tgtgaatat tacatgtctt tttctttttt atctgaagct tttttttttt
1141  ttctttaagt cttccttgttg gagacatttt aagaacgcc actcgaggaa gcattgattt
1201  tcatytggca tgacaggagt catcatttta aaaaatcggt gttaagttat aatttaaact
1261  ttatttgtaa cccaaaggty taatgtaaat ggatttcctg atatcctgcc atttgtactg
1321  gtatcaatat ttytatgt
```

FIG. 6

MGDPRCAPLLLLLLLPLLFTPPAGDAAVITGACDKDSQCGGMCCAVSIWVKSIRICTP
MGQVGDSCHPLTRKVPFWGRRMHHTCPCLPGLACLRTSFNRFICLARK

```
                    10                  20                   30                   40              50
Human Bv8  MRSLCCAPILLLLLLPPLLLTPRAGDAAVITGACDKDSQCGGGMCCAVSI
Mouse Bv8  MGDPRCAPLLLLLLLP-LLFTPPAGDAAVITGACDKDSQCGGGMCCAVSI 60                  70                   80                   90             100
Human Bv8  WVKSIRICTPMGKLGDSCHPLTRKNNFGNGRQERRKRKRSKRKE|VPFF-G
Mouse Bv8  WVKSIRICTPMGQVGDSCHPLTRKSHVANGRQERRRAKRRKRKE|VPFWG 110                 120         129
Human Bv8  RRMHHTCPCLPGLACLRTSFNRFICLAQK
Mouse Bv8  RRMHHTCPCLPGLACLRTSFNRFICLARK
```

```
   1 tggcctcccc agcttgccag gcacaaggct gagcgggagg aagcgagagg catctaagca ggcagtgttt
  71 tgccttcacc ccaagtgacc atgagaggtg ccacgcgagt ctcaatcatg ctcctcctag taactgtgtc
 141 tgactgtgct gtgatcacag gggcctgtga gcggatgtc cagtgtgggg caggcacctg ctgtgccatc
 211 agcctgtggc ttcgagggct gcggatgtgc acccgctgg ggcgggaagg cgaggagtgc cacccggca
 281 gccacaaggt cccttcttc aggaaacgca agcaccacac ctgtccttgc ttgcccaacc tgctgtgctc
 351 caggttcccg gacggcaggt accgctgctc catggacttg aagaacatca attttaggc gcttgcctgg
 421 tctcaggata ccccaccatcc ttttcctgag cacagctgg attttattt ctgccatgaa accagctcc
 491 catgactctc ccagtcccta cactgactac cctgatctct cttgtctagt acgcacatat gcacacaggc
 561 agacatacct cccatcatga catggtcccc agctggcct gaggatgtca cagcttgagg ctgtggtgtg
 631 aaaggtggcc agcctggttc tcttccctgc tcaggctgcc agagaggtgg taaatgcag aaaggacatt
 701 ccccctcccc tcccaggtg acctgctctc tttcctgggc cctgccctc tcccacatg tatcctcgg
 771 tctgaattag acattcctgg gcacaggctc ttggtgcat tgctcagagt ccaggtcct ggcctgaccc
 841 tcaggccctt cacgtgaggt ctgtgaggac caattgtgg gtagttcatc ttccctcgat tggttaactc
 911 cttagtttca gaccacagac tcaagattgg ctcttcccag aggggcagcag acagtcaccc caaggcaggt
 981 gtagggaggcc cagggaggcc aatcagcccc ctgaagactc tggtcccagt cagcctgtgg cttgtggcct
1051 gtgacctgtg accttctgcc agaattgtca tgcctctgag gcccctcctt accacacttt accagttaac
1121 cactgaagcc cccaattccc acagcttttc cattaaaatg caaatgtgg tggttcaatc taatctgata
1191 ttgacatatt agaaggcaat taggtgttt ccttaaacaa ctcctttcca aggatcagcc ctgagagcag
1261 gttggtgact ttgaggaggg cagtcctctg tccagattgg ggtgggagca agggacaggg agcagggcag
1331 gggctgaaag gggcactgat tcagaccagg gaggcaacta cacccaaca tgctgctttt agaataaaag
1401 caccaactga aaaaa
```

FIG. 9

```
Met Arg Gly Ala Thr Arg Val Ser Ile Met Leu Leu Val Thr Val Ser
                20                      10              30
Asp Cys Ala Val Ile Thr Gly Ala Cys Glu Arg Asp Val Gln Cys Gly Ala
                        40                                      50
Gly Thr Cys Cys Ala Ile Ser Leu Trp Leu Arg Gly Leu Arg Met Cys Thr
                                    60
Pro Leu Gly Arg Glu Gly Glu Glu Cys His Pro Gly Ser His Lys Val Pro
        70                                      80
Phe Phe Arg Lys Arg Lys His His Thr Cys Pro Cys Leu Pro Asn Leu Leu
                        90                                      100
Cys Ser Arg Phe Pro Asp Gly Arg Tyr Arg Cys Ser Met Asp Leu Lys Asn
                105
Ile Asn Phe
```

```
  1  GAA GTG AGG GGT ACC AAA GTA GAC TGT GTT TGT CGT CAC CTC AAG TGA TC

51  ATG AGA GGC GCT GTG CAT ATC TTC ATC ATG CTC CTT CTA GCA ACG GCG TCC
      M   R   G   A   V   H   I   F   I   M   L   L   L   A   T   A   S

102  GAC TGT GCG GTC ATC ACA GGG GCC TGT GAA CGA GAT ATC CAG TGT GGG GCC
      D   C   A   V   I   T   G   A   C   E   R   D   I   Q   C   G   A

153  GGC ACC TGC TGC GCT ATC AGT CTG TGG CTG CGG GGC TTG TGT ACC
      G   T   C   C   A   I   S   L   W   L   R   G   L   C   T

204  CCA CTG GGG CGT GAA GGA GAG TGC CAA CAC CAT ACC TGT CCC AGC CTG CTG
      P   L   G   R   E   G   E   C   Q   H   H   T   C   P   S   L   L

255  TTC TTG AGG AAA CGC CGA AAG CGC TTC CCG GAC GGC AGG TAC CGC TGC TTC CGG GAC TTG AAG AAT
      F   L   R   K   R   Q       C       Y   R   C   F   R   D   L   K   N

306  TGC TCC AGG TTC CCG GAC GGC AGG TAC CGC TGC TTC CGG GAC TTG AAG AAT
      C   S   R   F   P   D   G   R   Y   R   C   F   R   D   L   K   N

357  GCC AAC TTT TAGTTGTCTCTGGACTCTGTCTCGGAGCCTGACTGGGTGACCTCTTGCTTTACACCT
      A   N   F   *

GTGTGATTAGCTCCCTGCAACTTCGCCATTCCCATCTGTCCGTGTATGTGCAGACAGGCAGACC
     TTCCGCTATGGAATAGTTCACCAGGTGCAGAGAGAGTTCGTGGCCTTGAGAAGTTGGCCAGCCCG
     ACCTTCCTGCTCAGACTGCCTGAAGTTGTGACAGTGTGGCCTTCTCAGTTGCCTGCCCCTTCCTG
     CATGTGCGCTTCTCCTAAACCACACCTTTCTGGGCACTGGCCCATGGATGCACCACTAAATCAACA
     GGTCTGTGGGGTGGATGATCAACTTCTTCCATTTTCTTTATTGACTGGCTTCCTAATTTAAGG
     ACTGT
```

```
                       10          20          30          40          50
human  EG-VEGF  MRGATRVSIM LLLVTVSDCA VITGACERDV QCGAGTCCAI SLWLRGLRMC
murine EG-VEGF  MRGAVHIFIM LLLATASDCA VITGACERDI QCGAGTCCAI SLWLRGLRLC 60          70          80          90         100    105
human  EG-VEGF  TPLGREGEEC HPGSHKVPFF RKRKHHTCPC LPNLLCSRFP DGRYRCSMDL KNINF
murine EG-VEGF  TPLGREGEEC HPGSHKIPFL RKRQHHTCPC SPSLLCSRFP DGRYRCFRDL KNANF
```

FIG. 12

```
Human Bv8        28  AVITGACDKDSQCGGGMCCAVSIWVKSIRICTPMGKLGDSCHPLTRKVPF
Human EG-VEGF    20  AVITGACERDVQCGAGTCCAISLWLRGLRMCTPLGREGEECHPGSHKVPF Human Bv8        78  FGRRMHHTCPCLPGLACLRTSFNRFICLAQK               108
Human EG-VEGF    70  FRKRKHHTCPCLPNLLCSRFPDGRYRCSMDLKNINF         105
```

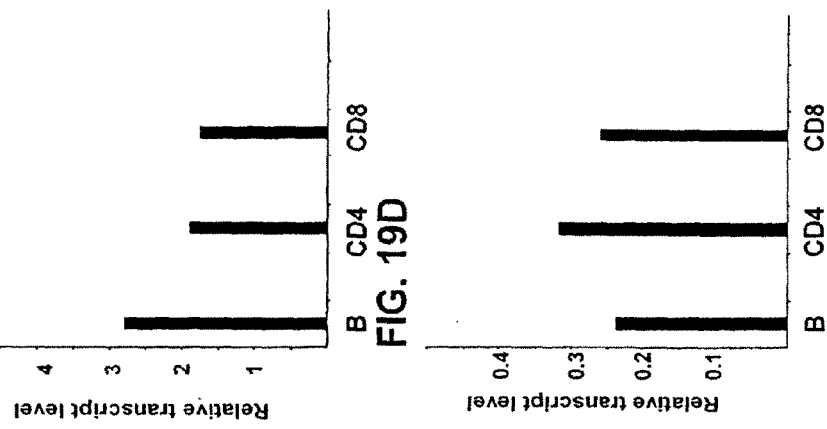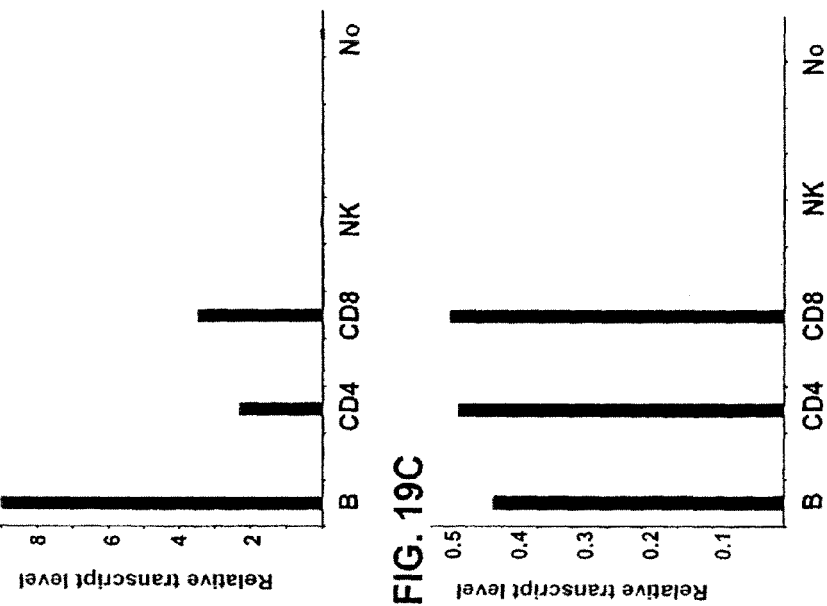

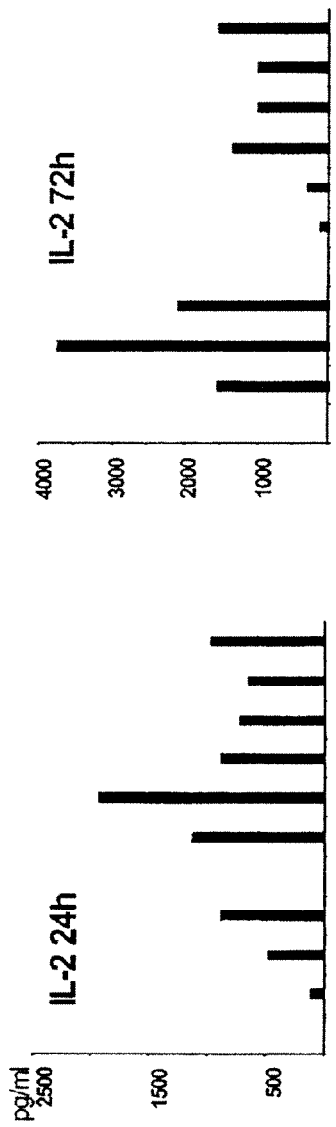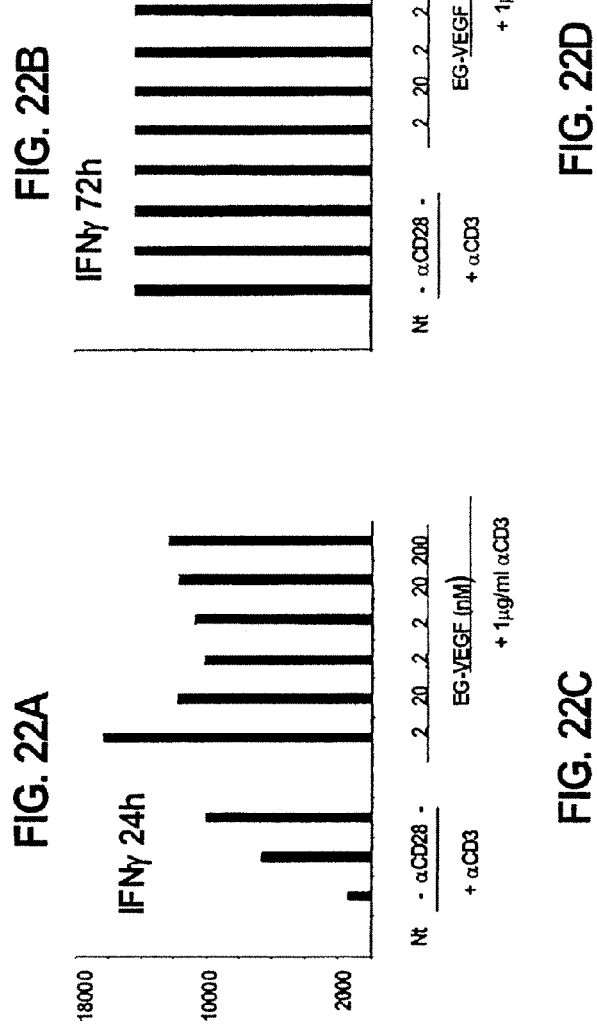

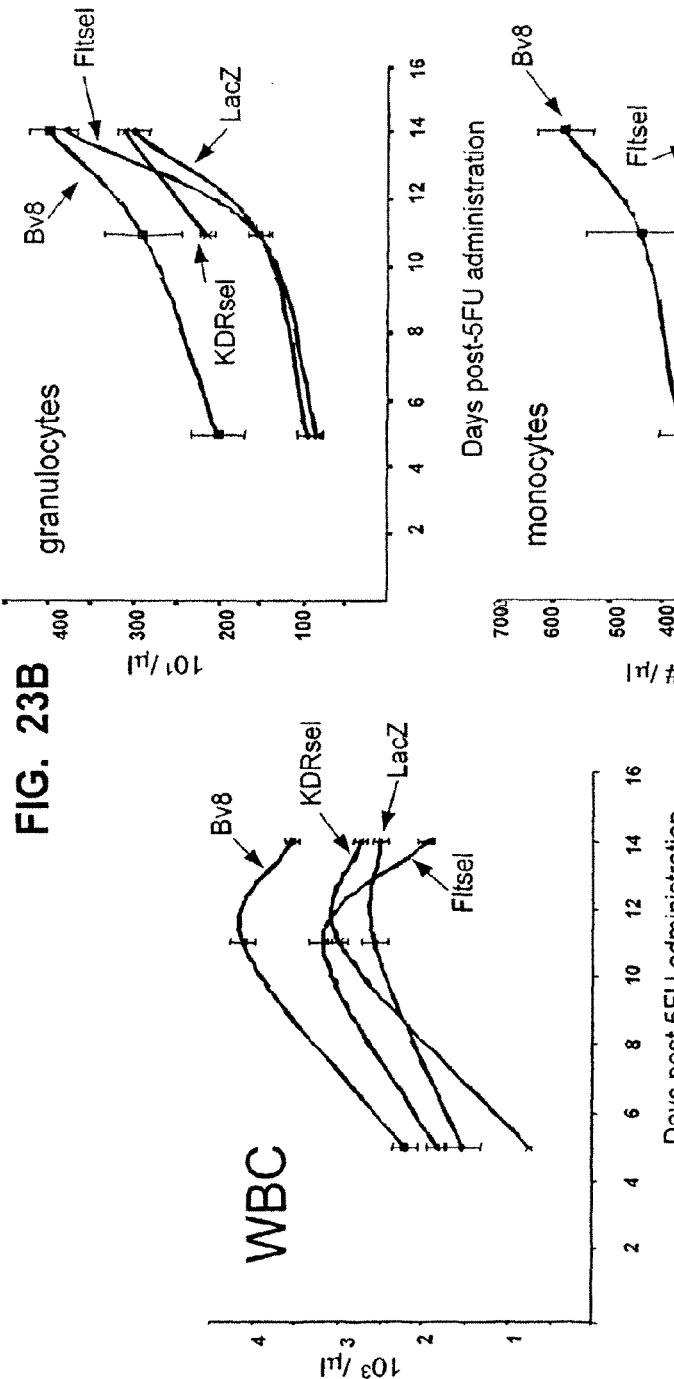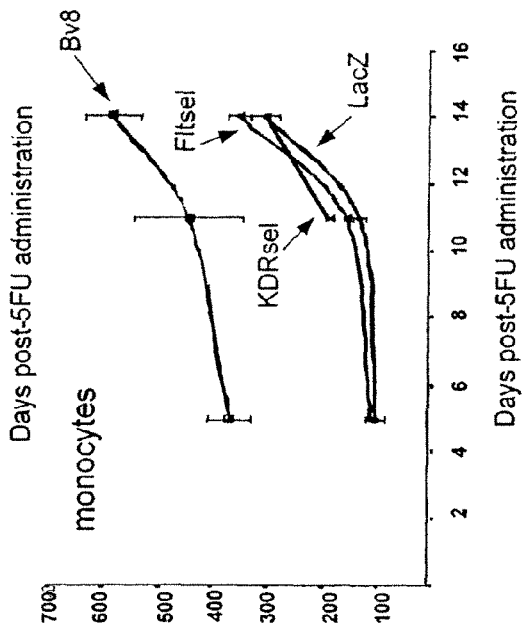

COMPOSITIONS WITH HEMATOPOIETIC AND IMMUNE ACTIVITY

CROSS-REFERENCE TO RELATED APPLICATIONS

This application is a continuation of U.S. application Ser. No. 12/611,397 filed Nov. 3, 2009, now U.S. Pat. No. 8,257,702, which is a divisional of U.S. application Ser. No. 10/549,241 filed Jun. 12, 2006, now U.S. Pat. No. 7,632,810, which is a national stage of PCT application No. PCT/US04/07622 filed Mar. 12, 2004, which claims the benefit of U.S. Provisional Application Nos. 60/454,462 filed Mar. 12, 2003 and 60/511,390 filed Oct. 14, 2003, the disclosures of each of which are incorporated herein in their entireties.

BACKGROUND OF THE INVENTION

Bv8 is a small protein that was originally isolated from the skin secretions of the frog Bombina variegate (Mollay et al., Eur. J. Pharmacol., 374:189-196 (1999)). Bv8 belongs to a structurally related class of peptides that includes endocrine gland derived vascular endothelial growth factor (EG-VEGF) (LeCouter et al., Nature, 412:877-884 (2001)). A distinguishing structural motif of these molecules is a colipase-fold, where 10 cysteine residues form five disulfide bridges within a conserved span.

Bv8 and EG-VEGF are homologs of vascular endothelial growth factor (VEGF), an angiogenic factor known to have an important role in tumor growth and survival. Both Bv8 and EG-VEGF have been identified as angiogenic factors with selective activities for endothelial cells of specific tissues. EG-VEGF promoted proliferation, migration, survival, and fenestration in cultured adrenal capillary endothelial cells and induced angiogenesis in ovary and testis. LeCouter et al., 2001, Nature, 412:877-884; LeCouter et al., 2003, Proc. Natl. Acad. Sci. USA, 100:2685-2690.

Like EG-VEGF, Bv8 promoted proliferation, survival, and migration of adrenal cortical capillary endothelial cells and induced angiogenesis in testis. LeCouter et al., 2003, Proc. Natl. Acad. Sci. USA, 100:2685-2690. The testis exhibits relatively high turnover of endothelial cells. Thus. Bv8 and EG-VEGF, along with other factors such as VEGF, are considered to be important in maintaining the integrity and regulating proliferation of the blood vessels in the testis.

VEGF is an angiogenic factor known to have an important role in tumor growth and survival. Because Bv8 and EG-VEGF are angiogenic factors with selective activity for specific tissues, it is desirable to further characterize the molecules.

SUMMARY OF THE INVENTION

The present invention is based on the identification of novel expression and activities of Bv8 and EG-VEGF in hematopoietic stem cells (HSCs), lineage-committed blood progenitor cells, and lymphocytes. In particular, as described in detail herein, Bv8, EG-VEGF, and their receptors are expressed in bone marrow HSCs, peripheral blood leukocytes (PBLs), as well as many hematological malignant cell lines. Both in vitro and in vivo experiments showed that Bv8 and EG-VEGF are capable of promoting colony formation of bone marrow mononuclear cells and spleen-derived progenitor cells, increasing populations of white blood cells, and promoting activation of B lymphocytes and T lymphocytes. Accordingly, Bv8 nucleic acids and polypeptides, EG-VEGF nucleic acids and polypeptides, or combinations thereof can be used in a number of assays and in diagnosis and treatment of conditions associated with hematopoiesis, neutropenias, immunodeficiency disorders, and autoimmune disorders.

Receptors for BV8 and EG-VEGF have now been found on bone marrow hematopoietic stem cells (CD34+) and on lineage committed progenitor cells (CD34+). BV8 and/or EG-VEGF induce proliferation of CD34+ myeloid and lymphoid progenitor cells. This proliferation leads to an increase in the number of white blood cells, including B cells, T cells, and in particular, neutrophils. BV8, EG-VEGF, and their agonists are therapeutically useful, for example, in the treatment of immunodeficiency disorders, such as lymphopenia, neutropenia, and others. These molecules are also useful to promote hematopoietic recovery after myelosupression, for example as induced by chemotherapy.

Various leukemic cells, such as ALL, AML, MPD, CML, and MDS cells, have now also been found to express receptors for BV8 and EF-VEGF. Antagonists of the growth factors EG-VEGF and/or BV8 are useful to inhibit proliferation of these leukemic cells.

BV8 and/or EG-VEGF have also surprisingly been found to induce B and T activation. Agonists and antagonists of these molecules are therapeutically useful to modulate an immune response. BV8. EG-VEGF, and their agonists are useful to and induce proliferation and activation of T cells in immunocompromised individuals, for example, in HIV patients. Antagonists of these molecules are therapeutically useful to inhibit an immune response, for example, those associated with an autoimmune disorder.

Proliferation of Bone Marrow Cells

In one aspect, the present invention provides a method of inducing bone marrow cell proliferation. In one embodiment, the method comprises contacting BM cells with Bv8. EG-VEGF, or a combination thereof in an amount effective to induce proliferation of the cells. In another embodiment, the method comprises introducing a polynucleotide sequence encoding Bv8, EG-VEGF, or a combination thereof, into BM cells in an amount effective to induce BM cell proliferation.

In one embodiment, the Bv8 and/or EG-VEGF is a native sequence polypeptide. Preferably, the native sequence Bv8 polypeptide is a native human Bv8 polypeptide. The native human Bv8 polypeptide may comprise the amino acid sequence of SEQ ID NO: 2 or of SEQ ID NO: 4. In another embodiment, the native sequence Bv8 polypeptide comprises the amino acid sequence of SEQ ID NO: 6. In another embodiment, the Bv8 polypeptide is capable of binding heparin. Preferably, the native sequence EG-VEGF polypeptide is a native human EG-VEGF polypeptide. The native human EG-VEGF polypeptide may comprise the amino acid sequence of SEQ ID NO:8. In another embodiment, the native sequence EG-VEGF comprises the amino acid sequence of SEQ ID NO: 10. In yet another embodiment, the Bv8 and/or EG-VEGF is an immunoadhesin. In a further embodiment, the Bv8 and/or EG-VEGF is chimeric.

In one embodiment, Bv8/EG-VEGF promote proliferation of BM hematopoietic stem cells and/or lineage committed progenitor cells. The lineage committed progenitor cells are generally of the myeloid and/or lymphoid lineage.

In a further aspect, the invention provides a method of maintaining specific blood cell populations in a patient in need of such cells. In one embodiment this method comprises contacting the cells with Bv8, EG-VEGF, or a combination thereof, in an amount effective to promote proliferation of said cells, thereby maintaining the population thereof. In another embodiment this method comprises introducing a polynucleotide sequence encoding Bv8, EG-VEGF, or a combination thereof, into cells in an amount effective to enhance cell survival. This method may further comprise introducing a polynucleotide sequence encoding VEGF to the cells. In one aspect, the particular cell types in need are leukocytes, preferably neutrophils, B lymphocytes, CD4+ T lymphocytes, and/or T lymphocytes. In another aspect, the patients suffer from neutropenia, lymphopenia, or an immunodeficiency disorder, and are therefore in need of neutrophils, B lymphocytes, CD4+ T lymphocytes, and/or CD8+ T lymphocytes.

Treatment of Abnormal Hematopoiesis

In a further aspect, the present invention provides a method of treating a mammal for a condition associated with abnormal hematopoiesis. In one embodiment, the method preferably comprises administering to the mammal a composition comprising Bv8, EG-VEGF, or a combination thereof, or an agonist or antagonist thereof, in an amount effective to treat the condition. The mammal is preferably human.

In one aspect, the composition comprising Bv8, EG-VEGF, or a combination thereof used in any of the methods of the invention comprises a native sequence Bv8 polypeptide and/or native sequence EG-VEGF polypeptide. Preferably, the native sequence Bv8 polypeptide is a native human Bv8 polypeptide. The native human Bv8 polypeptide may comprise the amino acid sequence of SEQ ID NO: 2 or the amino acid sequence of SEQ ID NO: 4. In another embodiment, the native sequence Bv8 comprises the amino acid sequence of SEQ ID NO: 6. In another embodiment, the Bv8 polypeptide binds heparin. Preferably, the native sequence EG-VEGF polypeptide is a native human EG-VEGF polypeptide. The native human EG-VEGF polypeptide may comprise the amino acid sequence of SEQ ID NO: 8. In another embodiment, the native sequence EG-VEGF comprises the amino acid sequence of SEQ ID NO: 10.

Treatment of Hematological Disorders

In yet a further aspect the invention provides a method of treating a hematological disorder in a mammal, preferably a human. In one embodiment the method comprises administering to the mammal a Bv8 antagonist, EG-VEGF antagonist, or a combination thereof, in an amount effective to inhibit cell proliferation. In one embodiment, the hematological disorders treatable with the methods of the invention include various leukemia, myeloproliferative disorders, myelodysplastic disorders, lymphoproliferative disorders, and lymphodysplastic disorders. Preferably, the hematological disorders is selected from the group consisting of acute myeloid leukemia (AML), chronic myelogenous leukemia (CML), acute lymphoblastic leukemia (ALL), multiple myeloma, T-cell lymphoma, polycythaemia vera (PV), essential thrombocythaemia (ET), and myeloid metaplasia (myelofibrosis), and the like.

Treatment of Immune Disorders

A further aspect of the invention provides a method for treating an immunodeficiency disorder in a mammal, preferably human, by administering Bv8, EG-VEGF, or a combination thereof. Patients suffering an immunodeficiency disorder lack B and T lymphocytes and are in need of enhanced B lymphocyte and/or T lymphocyte populations. Bv8, EG-VEGF, or a combination thereof can be provided to increase B and T cell population. The immunodeficiency disorder may be primary or secondary. In one embodiment, the secondary immunodeficiency disorder is a condition associated with an infectious disease including human immunodeficiency virus (HIV) or hepatitis. In another embodiment, the immunodeficiency disorder is a condition associated with the administration of an immunosuppressive agent, such as a therapeutic agent including but not limited to, fluorouracil, vincristine, cisplatin, oxoplatin, methotrexate, 3'-azido-3'-deoxythymidine, paclitaxel, doxetaxel, an anthracycline antibiotic, or mixtures thereof having a secondary immunosuppressive effect.

A further aspect of the invention provides a method for treating an autoimmune disorder in a mammal, preferably human. Bv8 antagonists, EG-VEGF antagonists, or combinations thereof, can be useful to treat autoimmune disorders where a decrease in the number of activated B cells, CD4+ T cells, and/or CD8+ T cells is desirable. Specific embodiments include using the agents and compositions provided herein to treat type II, III, and IV hypersensitivity responses associated with autoimmune disorders. In one embodiment, the method comprises administering to a mammal, a Bv8 antagonist, EG-VEGF antagonist, or a combination thereof, in an amount effective to inhibit the autoimmune disorder. In another embodiment, the method comprises administering a Bv8 antagonist, EG-VEGF antagonist, or a combination thereof, to a patient in an amount effective to inhibit proliferation of CD4+ T lymphocytes and/or CD8+ T lymphocytes.

Modulation of Immune Response

A further aspect of the invention provides a method for modulating an immune response. Bv8, EG-VEGF, or a combination thereof, or an agonist thereof, can be administered to activate B lymphocytes, CD4+ T lymphocytes, and/or CD8+ T lymphocytes. In one embodiment, Bv8, EG-VEGF, or a combination thereof, or an agonist thereof, can be administered to selectively promote or inhibit the proliferation of CD4+ T lymphocytes and/or CD8+ T lymphocytes.

Bv8 and EG-VEGF induce cytokine production in CD4+ T lymphocytes and CD8+ T lymphocytes. In one embodiment, a Bv8. EG-VEGF, an agonist thereof, or a combination thereof, that induces IL-2 synthesis in CD4+ T lymphocytes can be used to induce the proliferation of CD4+ lymphocytes. In another embodiment, Bv8. EG-VEGF, an agonist thereof, or a combination thereof, that induces IFN-γ in CD4+ T lymphocytes can be administered to inhibit the proliferation of CD4+ T lymphocytes.

Antagonists

Bv8 antagonists and EG-VEGF antagonists useful in the invention can be any composition capable of blocking, interfering, or minimizing Bv8 and/or EG-VEGF activities. These antagonists include anti-Bv8 and/or anti-EG-VEGF antibodies or fragments thereof, truncated peptides capable of binding to Bv8 and/or EG-VEGF receptors without eliciting signal transduction activities, soluble Bv8 and/or EG-VEGF receptors capable of sequestering Bv8 and/or EG-VEGF peptides, anti-Bv8 and/or anti-EG-VEGF receptor antibodies or small molecules capable of interfering with Bv8 or EG-VEGF receptor activities. In one embodiment, the Bv8 or EG-VEGF receptor is Bv8/EG-VEGF Receptor-1 and/or Bv8/EG-VEGF Receptor-2. Both Bv8 and EG-VEGF bind to Receptor 1 and Receptor 2 as described more fully in the detailed description.

Article of Manufacture

In a still further aspect, the invention provides an article of manufacture comprising a container, Bv8 and/or EG-VEGF, and instructions for using the Bv8 and/or EG-VEGF. In one embodiment, the instructions are for using the Bv8 and/or EG-VEGF to treat a condition that is associated with abnormal hematopoiesis. In another embodiment, the instructions are for using the Bv8 and/or EG-VEGF to treat a condition that is associated with immunodeficiency disorders. In another aspect the invention provides an article of manufacture comprising a container, a Bv8 antagonist and/or EG-VEGF antagonist, and instructions for using the Bv8 antagonist and/or EG-VEGF antagonist. In one embodiment the instructions are for using the Bv8 antagonist and/or EG- VEGF antagonist to treat hematological disorders. In another embodiment, the instructions are for using the Bv8 antagonist and/or EG-VEGF antagonist to treat immunodeficiency disorders. In another embodiment, the instructions are for using the Bv8 antagonist and/or EG-VEGF antagonist to treat autoimmune disorders.

Method to Identify Antagonist

Another aspect of the invention provides a method for identifying a Bv8 or EG-VEGF antagonist by contacting a candidate compound with Bv8 or EG-VEGF, determining the effect of the compound on a Bv8 or EG-VEGF biological activity, and identifying an antagonist where a Bv8 or EG-VEGF biological activity is inhibited. In one embodiment, a Bv8 antagonist is identified by its inhibition of the ability of Bv8 to stimulate endothelial cell proliferation. In another embodiment, a Bv8 or EG-VEGF antagonist is identified by its inhibition of the ability of Bv8 or EG-VEGF to promote endothelial cell survival.

BRIEF DESCRIPTION OF THE DRAWINGS

FIG. 1 shows the nucleotide sequence (SEQ ID NO: 1) of a cDNA encoding a human Bv8 homologue. Positions of the respective start codon ("ata" beginning at nucleic acid position 11) and stop codon ("tau" beginning at nucleic acid position 398) are presented in bold font and underlined.

FIG. 2 shows the amino acid sequence (SEQ ID NO: 2) of a human Bv8 homologue polypeptide as derived from the coding sequence of SEQ ID NO: 1. A putative signal sequence comprises amino acids 1 through 21.

FIG. 3 shows the nucleotide sequence (SEQ ID NO: 3) of a cDNA encoding an alternatively spliced version of the human Bv8 homologue. Positions of the respective start codon ("atg" beginning at nucleic acid position 11) and stop codon ("taa" beginning at nucleic acid position 394) are presented in bold font and underlined.

FIG. 4 shows the amino acid sequence (SEQ ID NO: 4) of a human Bv8 homologue polypeptide derived from the coding sequence of SEQ ID NO: 3.

FIG. 5 shows the polynucleotide sequence (SEQ ID NO: 5) of a mouse Bv8 homologue. Positions of the respective start codon ("atg" beginning at nucleic acid position 46) and stop codon ("tag" beginning at nucleic acid position 382) are presented in bold font and underlined.

FIG. 6 shows the amino acid sequence (SEQ ID NO: 6) of a mouse Bv8 homologue polypeptide derived from the coding sequence of SEQ ID NO: 5.

FIG. 7 shows an alignment of mouse and human Bv8 homologues. A potential heparin-binding domain is boxed. This domain is not present in an alternatively spliced transcript. A putative signal sequence is underlined. The mouse and human Bv8 homologues are approximately 96% identical.

FIG. 8 shows the polynucleotide sequence (SEQ ID NO:7) of a cDNA encoding human native sequence EG-VEGF.

FIG. 9 shows the amino acid sequence (SEQ ID NO:8) of a human native sequence EG-VEGF polypeptide derived from the coding sequence of SEQ ID NO:7.

FIG. 10 shows the polynucleotide sequence (SEQ ID NO:9) of a cDNA encoding a native mouse EG-VEGF polypeptide (SEQ ID NO: 10).

FIG. 11 shows an alignment of human native EG-VEGF polypeptide (SEQ ID NO:8) and native mouse EG-VEGF polypeptide (SEQ ID NO:8).

FIG. 12 shows an alignment of the amino acid sequences of human Bv8 homologue (amino acids 28-108 of SEQ ID NO:4) and human EG-VEGF (amino acids 20-105 of SEQ ID NO: 10). The signal sequence is not shown for either molecule. Human Bv8 is approximately 60% identical to human EG-VEGF.

FIGS. 14A and B show Bv8 expression in tonsillitis, where FIG. 14A shows hematoxylin-eosin staining of the tissue and FIG. 14B shows Bv8 expression in the same tissue sample using $^{33}$P-labeled probes. FIGS. 14C and D show Bv8 expression in appendicitis, where FIG. 14C shows a hematoxylin-eosin staining of the tissue and FIG. 14D shows Bv8 expression in the same tissue sample using $^{33}$P-labeled probes.

FIG. 15A shows that Bv8 is strongly expressed in bone marrow as well as testis; FIG. 15B shows differential expression of Bv8 in various types of hematopoietic cells; and FIGS. 15C and D show hematopoietic cell expression of Bv8/EG-VEGF receptor-1 (FIG. 15C) and Bv8/EG-VEGF receptor-2 (FIG. 15D).

FIG. 17A shows that Bv8 (at both 5 nM and 50 mM) increases colony formation in mouse bone marrow mononuclear cells. FIG. 17B shows that Bv8, similar to EG-VEGF, increases colony formation of certain types of myeloid progenitor cells in human bone marrow mononuclear cell cultures. Ct refers to complete medium as described in Example 2. Basal refers to basal medium as described in Example 2.

FIGS. 19A-D are graphs showing the results of real time quantitative PCR expression analysis of Bv8/EG-VEGF receptor-1 and Bv8/EG-VEGF receptor-2 in human and mouse derived B lymphocytes, CD4+ T lymphocytes, CD8+ T lymphocytes, and Natural Killer cells. FIGS. 19A and B show the relative transcript level of Bv8/EG-VEGF receptor-1 in human (FIG. 19A) and mouse (FIG. 19B) derived B lymphocytes, CD4+ T lymphocytes, CD8+ T lymphocytes, and Natural Killer cells. FIGS. 19C and D show the relative transcript level of Bv8/EG-VEGF receptor-2 in human (FIG. 19C) and mouse (FIG. 19C) derived B lymphocytes, CD4+ T lymphocytes, CD8+ T lymphocytes, and Natural Killer cells.

FIGS. 22A-D are graphs showing that EG-VEGF induces cytokine production in CD4+ T cells. EG-VEGF induced production of IL-2 and IFN-γ in CD4+ T cells.

FIGS. 23A-E are graphs showing that Bv8 promotes hematopoietic recovery in vivo after myelosuppression with 5-FU. Cells counts were measured 5 days, 11 days, and 14 days after in vivo introduction of Bv8-expressing adenoviral vectors. Flt$^{sel}$ refers to a VEGF mutant that selectively binds FLT1 receptor. KDR$^{sel}$ refers to a VEGF mutant that selectively binds KDR receptor. Bv8 increased white blood cell count, granulocyte count, monocyte count, and platelet count after myelosuppression with 5-FU.

DETAILED DESCRIPTION OF THE PREFERRED EMBODIMENTS

I. Definitions

Figure 13:
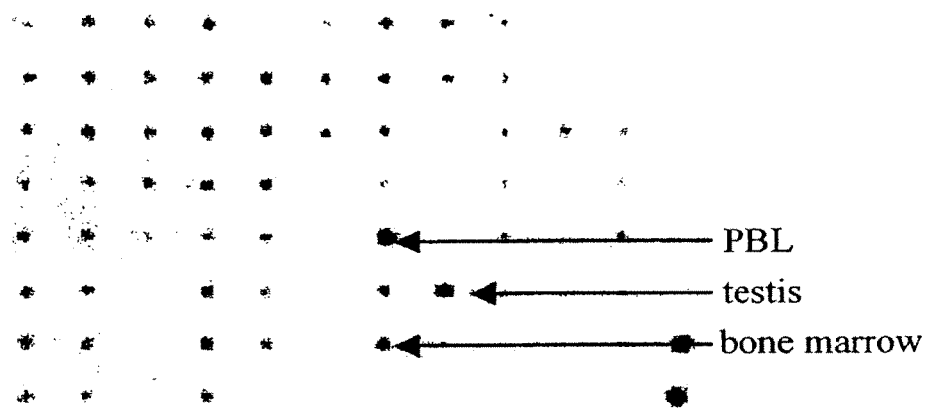
FIG. 13 shows the results of a dot blot hybridization of RNA assay that reveals a hBv8 signal in bone marrow. PBLs, as well as testis.
Figure 14A:
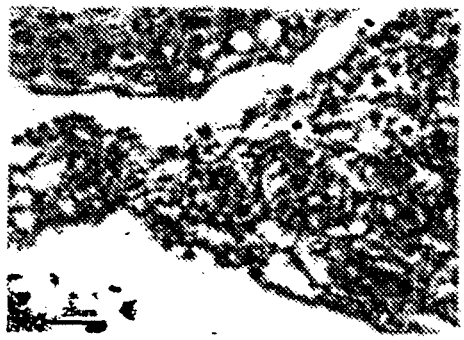
FIGS. 14A-D are photographs showing results of in situ hybridization studies that reveal restricted expression of Bv8 in neutrophils and associated infiltrating cells.
Figure 14B:
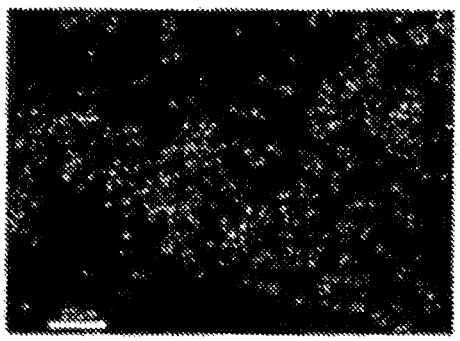
Figure 14C:
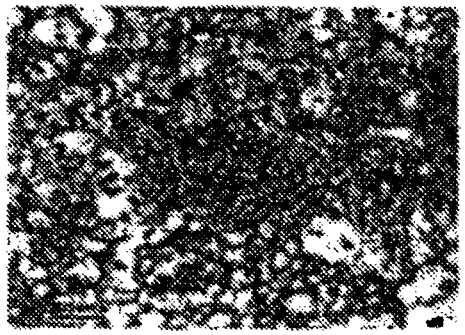
Figure 14D:
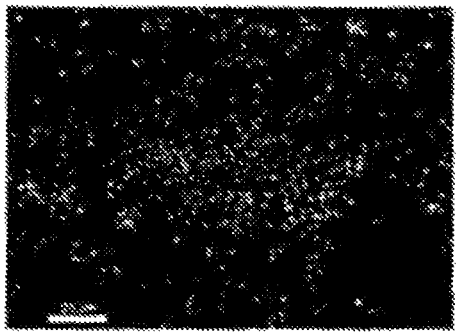

Unless defined otherwise, technical and scientific terms used herein have the same meaning as commonly understood by one of ordinary skill in the art to which this invention belongs. See, e.g. Singleton et al., *Dictionary of Microbiology and Molecular Biology* 2nd ed., J. Wiley & Sons (New York, N.Y. 1994); Sambrook et al., *Molecular Cloning, A Laboratory Manual*, Cold Springs Harbor Press (Cold Springs Harbor, N.Y. 1989). For purposes of the present invention, the following terms are defined below.

The terms "Bv8" and "Bv8 polypeptide," are used interchangeably herein, and refer to native sequence Bv8, Bv8 variants, and chimeric Bv8, each of which is defined herein. Optionally, the Bv8 is not associated with native glycosylation. "Native glycosylation" refers to the carbohydrate moieties that are covalently attached to Bv8 when it is produced in mammalian cells, particularly in the cells in which it is produced in nature. Accordingly, human Bv8 produced in a non-human cell is an example of Bv8 that may "not be associated with native glycosylation." Bv8 may not be glycosylated at all, as in the case where it is produced in prokaryotes, e.g. *E. coli*.

Bv8 polynucleotide is RNA or DNA that encodes a Bv8 polypeptide, as defined above, or which hybridizes to such DNA or RNA and remains stably bound to it under stringent hybridization conditions and is greater than about 10 nucleotides in length. Stringent conditions are those which (1) employ low ionic strength and high temperature for washing, for example, 0.15 M NaCl/0.015 M sodium citrate/0.1% NaDodSO$_4$ at 50° C., or (2) use during hybridization a denaturing agent such as formamide, for example, 50% (vol/vol) formamide with 0.1% bovine serum albumin/0.1% Ficoll/0.1% polyvinlypyrrolidone/50 mM sodium phosphate buffer at pH 6.5 with 750 mM NaCl, 75 mM sodium citrate at 42° C.

A polynucleotide is operably linked when it is placed into a functional relationship with another nucleic acid sequence. Bv8 polynucleotide may be operably linked with another nucleic acid sequence in a vector such that it may be expressed in a particular host organism. This may be done by methods well known in the art. For example, DNA for a presequence or a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adapters or linkers are used in accord with conventional practice.

"Native sequence Bv8" comprises a polypeptide having the same amino acid sequence as Bv8 derived from nature, regardless of its mode of preparation. Thus, native sequence Bv8 can have the amino acid sequence of naturally occurring human Bv8, murine Bv8, or Bv8 from any other mammalian species. For example a full-length native sequence human Bv8 amino acid sequence is shown in FIG. 2 (SEQ ID NO: 2). A second full-length native sequence human Bv8 is shown in FIG. 4 (SEQ ID NO: 4). These two sequences are the result of the alternative splicing of an exon that encodes a canonical heparin binding domain. Thus the native sequence human Bv8 whose amino acid sequence is shown in FIG. 2 (SEQ ID NO: 2) comprises a heparin binding domain, while the native sequence Bv8 depicted in FIG. 4 (SEQ ID NO: 4) does not. A native sequence mouse Bv8 amino acid sequence is shown in FIG. 6 (SEQ ID NO: 6). Human and murine Bv8 sequences are also disclosed, for example, in Wechselberger et al., 1999, *FEBS Lett.*, 462:177-181 and Li et al., 2001, *Mol. Pharm.*, 59:692-698. Such native sequence Bv8 can be isolated from nature or can be produced by recombinant and/or synthetic means. The term "native sequence Bv8" specifically encompasses naturally occurring prepro, pro, and mature forms and truncated forms of Bv8, naturally occurring variant forms (e.g. alternatively spliced forms, such as that shown in FIG. 4 (SEQ ID NO: 4)), and naturally occurring allelic variants. A preferred native sequence Bv8 is a full-length native sequence human Bv8 as shown in FIG. 2 (SEQ ID NO: 2).

"Bv8 variants" are biologically active Bv8 polypeptides having an amino acid sequence that differs from the sequence of a native sequence Bv8 polypeptide, such as those shown in FIGS. 2, 4 and 6 (SEQ ID NOs: 2, 4 and 6) for human and murine Bv8, by virtue of an insertion, deletion, modification, and/or substitution of one or more amino acid residues within the native sequence. Bv8 variants generally have less than 100% sequence identity with a native sequence Bv8, such as the human Bv8 of FIG. 2 (SEQ ID NO: 2). Ordinarily, however, a biologically active Bv8 variant will have an amino acid sequence with at least about 70% amino acid sequence identity with the amino acid sequence of a naturally occurring Bv8 such as the human Bv8 of FIG. 2 (SEQ ID NO: 2), preferably at least about 75%, more preferably at least about 80%, even more preferably at least about 85%, even more preferably at least about 90%, with increasing preference of at least about 95% to at least about 99% amino acid sequence identity, in 1% increments. The Bv8 variants include peptide fragments of at least 5 amino acids that retain a biological activity of the corresponding native sequence Bv8 polypeptide. Bv8 variants also include Bv8 polypeptides wherein one or more amino acid residues are added at the N- or C-terminus of, or within, a native Bv8 sequence. Bv8 variants also include Bv8 polypeptides where a number of amino acid residues are deleted and optionally substituted by one or more amino acid residues. Bv8 variants also may be covalently modified, for example by substitution with a moiety other than a naturally occurring amino acid or by modifying an amino acid residue to produce a non-naturally occurring amino acid. Bv8 variants may comprise a heparin binding domain.

As used herein, the terms "EG-VEGF" and "EG-VEGF polypeptide," which are used interchangeably, refer to native sequence EG-VEGF, EG-VEGF variants, and chimeric EG-VEGF, each of which is defined herein. Optionally, the EG-VEGF is not associated with native glycosylation. "Native glycosylation" refers to the carbohydrate moieties that are covalently attached to EG-VEGF when it is produced in mammalian cells, particularly in the cells in which it is produced in nature. Accordingly, human EG-VEGF produced in a non-human cell is an example of EG-VEGF that may "not be associated with native glycosylation." Sometimes the EG-VEGF may not be glycosylated at all, as in the case where it is produced in prokaryotes, e.g. E. coli.

EG-VEGF polynucleotide is RNA or DNA that encodes a EG-VEGF polypeptide, as defined above, or which hybridizes to such DNA or RNA and remains stably bound to it under stringent hybridization conditions and is greater than about 10 nucleotides in length. Stringent conditions are those which (1) employ low ionic strength and high temperature for washing, for example, 0.15 M NaCl/0.015 M sodium citrate/0.1% NaDodSO$_4$ at 50° C., or (2) use during hybridization a denaturing agent such as formamide, for example, 50% (vol/vol) formamide with 0.1% bovine serum albumin/0.1% Ficoll/0.1% polyvinlypyrrolidone/50 mM sodium phosphate buffer at pH 6.5 with 750 mM NaCl, 75 mM sodium citrate at 42° C.

A polynucleotide is operably linked when it is placed into a functional relationship with another nucleic acid sequence. EG-VEGF poly nucleotide may be operably linked with another nucleic acid sequence in a vector such that it may be expressed in a particular host organism. This may be done by methods well known in the art. For example, DNA for a presequence or a secretory leader is operably linked to DNA for a polypeptide if it is expressed as a preprotein that participates in the secretion of the polypeptide: a promoter or enhancer is operably linked to a coding sequence if it affects the transcription of the sequence: or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adapters or linkers are used in accord with conventional practice.

"Native sequence EG-VEGF" comprises a polypeptide having the same amino acid sequence as EG-VEGF derived from nature, regardless of its mode of preparation. Thus, native sequence EG-VEGF can have the amino acid sequence of naturally occurring human EG-VEGF, murine EG-VEGF, or EG-VEGF from any other mammalian species. In an embodiment, a full-length native sequence human EG-VEGF comprises an amino acid sequence of SEQ ID NO:8. In an embodiment, a native sequence mouse EG-VEGF amino comprises an acid sequence of SEQ ID NO: 10. Human and murine EG-VEGF sequences are also disclosed, for example, in LeCouter et al., 2001, Nature, 412:877-884.

Such native sequence EG-VEGF can be isolated from nature or can be produced by recombinant and/or synthetic means. The term "native sequence EG-VEGF" specifically encompasses naturally occurring prepro, pro, and mature forms and truncated forms of EG-VEGF, naturally occurring variant forms (e.g. alternatively spliced forms), and naturally occurring allelic variants. A preferred native sequence EG-VEGF is a full-length native sequence human EG-VEGF comprising an amino acid sequence of SEQ ID NO:8.

"EG-VEGF variants" are biologically active EG-VEGF polypeptides having an amino acid sequence that differs from the sequence of a native sequence EG-VEGF polypeptide, such as for human and murine EG-VEGF (SEQ ID NOs:8 and 10), by virtue of an insertion, deletion, modification, and/or substitution of one or more amino acid residues within the native sequence. EG-VEGF variants generally have less than 100% sequence identity with a native sequence EG-VEGF. Ordinarily, however, a biologically active EG-VEGF variant will have an amino acid sequence with at least about 70% amino acid sequence identity with the amino acid sequence of a naturally occurring EG-VEGF, preferably at least about 75%, more preferably at least about 80%, even more preferably at least about 85%, even more preferably at least about 90%, with increasing preference of at least about 95% to at least about 99% amino acid sequence identity, in 1% increments. The EG-VEGF variants include peptide fragments of at least 5 amino acids that retain a biological activity of the corresponding native sequence EG-VEGF polypeptide. EG-VEGF variants also include EG-VEGF polypeptides wherein one or more amino acid residues are added at the N- or C-terminus of, or within, a native EG-VEGF sequence. EG-VEGF variants also include EG-VEGF polypeptides where a number of amino acid residues are deleted and optionally substituted by one or more amino acid residues. EG-VEGF variants also may be covalently modified, for example by substitution with a moiety other than a naturally occurring amino acid or by modifying an amino acid residue to produce a non-naturally occurring amino acid.

"Percent amino acid sequence identity" with respect to the Bv8 or EG-VEGF sequence is defined herein as the percentage of amino acid residues in the candidate sequence that are identical with the residues in the Bv8 or EG-VEGF sequence, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the candidate Bv8 or EG-VEGF sequence shall be construed as affecting sequence identity or homology. Methods and computer programs for the alignment are well known in the art. One such computer program is "ALIGN-2," authored by Genentech, Inc., which has been filed with user documentation in the United States Copyright Office, Washington, D.C. 20559, where it is registered under U.S. Copyright Registration No. TXU510087.

A "chimeric EG-VEGF" molecule is a polypeptide comprising full-length EG-VEGF or one or more domains thereof fused or bonded to heterologous polypeptide. The chimeric EG-VEGF molecule will generally share at least one biological property in common with naturally occurring EG-VEGF. An example of a chimeric EG-VEGF molecule is one that is epitope tagged for purification purposes. Another chimeric EG-VEGF molecule is a EG-VEGF immunoadhesin.

The term "epitope-tagged" when used herein refers to a chimeric polypeptide comprising Bv8 or EG-VEGF fused to a "tag polypeptide". The tag polypeptide has enough residues to provide an epitope against which an antibody can be made, yet is short enough such that it does not interfere with biological activity of the Bv8. The tag polypeptide preferably is fairly unique so that the antibody against it does not substantially cross-react with other epitopes. Suitable tag polypeptides generally have at least six amino acid residues and usually between about 8-50 amino acid residues (preferably between about 9-30 residues). Preferred are poly-histidine sequences, which bind nickel, allowing isolation of the tagged protein by Ni-NTA chromatography as described (See, e.g., Lindsay et al., 1996, *Neuron*, 17:571-574).

"Isolated" means Bv8 or EG-VEGF that has been purified from a Bv8 or EG-VEGF source, or has been prepared by recombinant or synthetic methods and purified. Purified Bv8 or EG-VEGF is substantially free of other polypeptides or peptides. "Substantially free" here means less than about 5%, preferably less than about 2%, more preferably less than about 1%, even more preferably less than about 0.5%, most preferably less than about 0.1% contamination with other source proteins.

"Essentially pure" protein means a composition comprising at least about 90% by weight of the protein, based on total weight of the composition, preferably at least about 95% by weight, more preferably at least about 90% by weight, even more preferably at least about 95% by weight. "Essentially homogeneous" protein means a composition comprising at least about 99% by weight of protein, based on total weight of the composition.

"Agonists" are molecules or compounds that have one or more of the biological properties of native sequence Bv8 or EG-VEGF. These may include, but are not limited to, small organic molecules, peptides, and agonist anti-Bv8 or anti-EG-VEGF antibodies.

The term "antagonist" is used in the broadest sense, and includes any molecule that partially or fully blocks, inhibits, or neutralizes a biological activity of a native Bv8 or EG-VEGF polypeptide. Suitable antagonist molecules specifically include antagonist antibodies or antibody fragments, fragments or amino acid sequence variants of native Bv8 or EG-VEGF polypeptides, soluble Bv8 or EG-VEGF receptors or fragments thereof, peptides, small organic molecules, etc. Methods for identifying agonists or antagonists of a Bv8 and/or EG-VEGF polypeptide may comprise contacting a Bv8 or EG-VEGF polypeptide with a candidate agonist or antagonist molecule and measuring a detectable change in one or more biological activities normally associated with the Bv8 or EG-VEGF polypeptide.

"Active" or "activity" for the purposes herein refers to form(s) of Bv8 or EG-VEGF which retain a biological and/or an immunological activity of native or naturally-occurring Bv8 or EG-VEGF, wherein "biological" activity refers to a biological function (either inhibitory or stimulatory) caused by a native or naturally-occurring Bv8 or EG-VEGF other than the ability to induce the production of an antibody against an antigenic epitope possessed by a native or naturally-occurring Bv8 or EG-VEGF and an "immunological" activity refers to the ability to induce the production of an antibody against an antigenic epitope possessed by a native or naturally-occurring Bv8 or EG-VEGF.

Thus, "biologically active" when used in conjunction with "Bv8", "isolated Bv8", an agonist of Bv8, "EG-VEGF", "isolated EG-VEGF", or an agonist of EG-VEGF means a Bv8 or EG-VEGF polypeptide that exhibits or shares an effector function of native sequence Bv8 or EG-VEGF respectively. A principal effector function of Bv8 of EG-VEGF is its ability to stimulate the proliferation of endothelial cells. Even more preferably, the biological activity is the ability to regulate hematopoiesis.

"Biological property" when used in conjunction with "Bv8" or "isolated Bv8" or an "agonist" of Bv8, means having an effector or antigenic function or activity that is directly or indirectly caused or performed by native sequence Bv8 (whether in its native or denatured conformation). Effector functions include enhancement of proliferation of endothelial cells, induction of angiogenesis and/or regulation of hematopoiesis.

"Biological property" when used in conjunction with "EG-VEGF", "isolated EG-VEGF", an "agonist" of EG-VEGF, means having an effector or antigenic function or activity that is directly or indirectly caused or performed by native sequence EG-VEGF respectively (whether in its native or denatured conformation). Effector functions include enhancement of proliferation of endothelial cells, induction of angiogenesis and/or regulation of hematopoiesis.

"Bv8 receptor" is a molecule to which Bv8 binds and mediates the biological properties of Bv8. Bv8 receptors may also bind and mediate the biological properties of EG-VEGF. Therefore, the term "Bv8 receptor" includes within its meaning Bv8/EG-VEGF receptor-1 and Bv8/EG-VEGF receptor-2 (LeCouter et al., 2003, *Proc. Natl. Acad. Sci. USA*, 100:2685-2690; Lin et al., 2002, *J. Biol. Chem.*, 277:19276-19280; Masuda et al., 2002, *Biochem. Biophys. Res. Commun.*, 293:396-402).

"EG-VEGF receptor" is a molecule to which EG-VEGF binds and mediates the biological properties of EG-VEGF. EG-VEGF receptors may also bind and mediate the biological properties of Bv8. Therefore, the term "EG-VEGF receptor" includes within its meaning Bv8/EG-VEGF receptor-1 and Bv8/EG-VEGF receptor-2 (LeCouter et al., 2003 *Proc. Natl. Acad. Sci. USA*, 100:2685-2690; Lin et al., 2002, *J. Biol. Chem.*, 277:19276-19280; Masuda et al., 2002, *Biochem. Biophys. Res. Commun.*, 293:396-402).

The term "antibody" herein is used in the broadest sense and specifically covers human, non-human (e.g. murine) and humanized monoclonal antibodies (including full length monoclonal antibodies), polyclonal antibodies, multispecific antibodies (e.g., bispecific antibodies), and antibody fragments so long as they exhibit the desired biological activity.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health. Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917). "Framework" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment that contains a complete antigen-recognition and -binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g. IgG1, IgG2. IgG3, IgG4. IgA1, and IgA2. The heavy-chain constant domains that correspond to the different classes of immunoglobulins are called α, δ, ε, γ, and μ, respectively. The subunit structures and three-dimensional configurations of different classes of immunoglobulins are well known.

"Antibody fragments" comprise a portion of a full-length antibody, generally the antigen binding or variable domain thereof. Examples of antibody fragments include Fab, Fab', $F(ab')_2$, and Fv fragments; diabodies; linear antibodies; single-chain antibody molecules; and multi-specific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., 1975, *Nature* 256:495, or may be made by recombinant DNA methods (see, e.g., U.S. Pat. No. 4,816,567). The "monoclonal antibodies" may also be isolated from phage antibody libraries using the techniques described in Clackson et al., 1991, *Nature* 352:624-628 and Marks et al., 1991, *J. Mol. Biol.* 222:581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., 1984, *Proc. Null. Acad. Sci. USA*, 81:6851-6855).

"Humanized" forms of non-human (e.g., murine) antibodies are chimeric antibodies that contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The FRs may optionally be those of a consensus or modified consensus sequence, as described, for example, in Carter et al., U.S. Pat. No. 6,054,297. The humanized antibody optionally also will comprise at least a portion of an immunoglobulin constant region (Fc), typically that of a human immunoglobulin. For further details, see Jones et al., 1986, *Nature,* 321:522-525; Reichmann et al., 1988, *Nature,* 332:323-329; and Presta, 1992, *Curr. Op. Struct. Biol.,* 2:593-596.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies,* vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example. EP 404,097; WO 93/11161; and Hollinger et al., 1993, *Proc. Natl. Acad. Sci. USA,* 90:6444-6448.

The expression "linear antibodies" when used throughout this application refers to the antibodies described in Zapata et al., 1995, *Protein Eng.,* 8(10):1057-1062. Briefly, these antibodies comprise a pair of tandem Fd segments ($V_H$-$C_H$1-$V_H$-$C_H$1) which form a pair of antigen binding regions. Linear antibodies can be bispecific or monospecific.

The term "epitope" is used to refer to binding sites for (monoclonal or polyclonal) antibodies on protein antigens.

By "agonist antibody" is meant an antibody that is a Bv8 or EG-VEGF agonist and thus possesses one or more of the biological properties of native sequence Bv8 or EG-VEGF.

The term "Bv8 immunoadhesin" and "EG-VEGF immunoadhesin" is used interchangeably with the term "Bv8 immunoglobulin chimera" and "EG-VEGF immunoglobulin chimera", respectively, and refers to a chimeric molecule that combines at least a portion of a Bv8 or EG-VEGF molecule (native or variant) with an immunoglobulin sequence. The immunoglobulin sequence preferably, but not necessarily, is an immunoglobulin constant domain. Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use.

Examples of homomultimeric immunoadhesins that have been described for therapeutic use include the CD4-IgG immunoadhesin for blocking the binding of HIV to cell-surface CD4. Data obtained from Phase I clinical trials, in which CD4-IgG was administered to pregnant women just before delivery, suggests that this immunoadhesin may be useful in the prevention of maternal-fetal transfer of HIV (Ashkenazi et al., 1993, *Intern. Rev. Immunol,* 10:219-227). An immunoadhesin that binds tumor necrosis factor (TNF) has also been developed. TNF is a proinflammatory cytokine that has been shown to be a major mediator of septic shock. Based on a mouse model of septic shock, a TNF receptor immunoadhesin has shown promise as a candidate for clinical use in treating septic shock (Ashkenazi et al., 1991, *Proc. Natl. Acad. Sci. USA,* 88:10535-10539). ENBREL® (etanercept), an immunoadhesin comprising a TNF receptor sequence fused to an IgG Fc region, was approved by the U.S. Food and Drug Administration (FDA), on Nov. 2, 1998, for the treatment of rheumatoid arthritis. The new expanded use of ENBREL™ in the treatment of rheumatoid arthritis was approved by FDA on Jun. 6, 2000. For recent information on TNF blockers, including ENBREL®, see Lovell et al., 2000, *N. Engl. J. Med.* 342:763-169, and accompanying editorial on p 810-811; and Weinblatt et al., 1999, *N. Engl. J. Med.* 340: 253-259; reviewed in Maini and Taylor, 2000, *Annu. Rev. Med.* 51:207-229.

If the two arms of the immunoadhesin structure have different specificities, the immunoadhesin is called a "bispecific immunoadhesin" by analogy to bispecific antibodies. Dietsch et al., 1993, *J. Immunol. Methods,* 162:123 describe such a bispecific immunoadhesin combining the extracellular domains of the adhesion molecules, E-selectin and P-selectin, each of which selectin is expressed in a different cell type in nature. Binding studies indicated that the bispecific immunoglobulin fusion protein so formed had an enhanced ability to bind to a myeloid cell line compared to the monospecific immunoadhesins from which it was derived.

The term "heteroadhesin" is used interchangeably with the expression "chimeric heteromultimer adhesin" and refers to a complex of chimeric molecules (amino acid sequences) in which each chimeric molecule combines a biologically active portion, such as the extracellular domain of each of the heteromultimeric receptor monomers, with a multimerization domain. The "multimerization domain" promotes stable interaction of the chimeric molecules within the heteromultimer complex. The multimerization domains may interact via an immunoglobulin sequence, leucine zipper, a hydrophobic region, a hydrophilic region, or a free thiol that forms an intermolecular disulfide bond between the chimeric molecules of the chimeric heteromultimer. The multimerization domain may comprise an immunoglobulin constant region. In addition a multimerization region may be engineered such that steric interactions not only promote stable interaction, but further promote the formation of heterodimers over homodimers from a mixture of monomers. "Protuberances" are constructed by replacing small amino acid side chains from the interface of the first polypeptide with larger side chains (e.g. tyrosine or tryptophan). Compensatory "cavities" of identical or similar size to the protuberances are optionally created on the interface of the second polypeptide by replacing large amino acid side chains with smaller ones (e.g. alanine or threonine). The immunoglobulin sequence preferably, but not necessarily, is an immunoglobulin constant domain. The immunoglobulin moiety in the chimeras of the present invention may be obtained from $IgG_1$, $IgG_2$, $IgG_3$ or $IgG_4$ subtypes, IgA, IgE, IgD or IgM, but preferably $IgG_1$ or $IgG_3$.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. Specifically, the treatment may directly prevent, slow down or otherwise decrease the pathology of cellular degeneration or damage, such as the pathology of tumor cells in cancer treatment, or may render the cells more susceptible to treatment by other therapeutic agents.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, other higher primates, domestic and farm animals, and zoo, sports, or pet animals, such as dogs, cats, cattle, horses, sheep, pigs, goats, rabbits, and the like. Preferably, the mammal is human.

"Tumor", as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, and various types of head and neck cancer.

"Hematological disorders" refers to disorders characterized by abnormal proliferation and/or differentiation of blood cells that can lead to dysplastic changes in blood cells and hematologic malignancies. Many hematological disorders can be classified as leukemias, myeloproliferative disorders (MPDs), myelodysplastic disorders, lymphoproliferative disorders, and lymphodysplastic disorders. Many of these disorders can occur in adults as well as children. Examples of hematological disorders include, but are not limited to, acute myeloid leukemia (AML), chronic myelogenous leukemia (CML), acute lymphoblastic leukemia (ALL), multiple myeloma, T-cell lymphoma, lymphodysplastic leukemia, polycythaemia vera (PV), essential thrombocythaemia (ET), and myeloid metaplasia (myelofibrosis).

The term "neutropenia" refers to disorders or conditions characterized by an abnormally low or reduced number of circulating neutrophils. Neutropenia may be the result of disease, genetic disorders, drugs, toxins, radiation, and many therapeutic treatments, such as high dose chemotherapy and conventional oncology therapy. Examples of disorders or conditions associated with neutropenia include, but are not limited to, hematological disorders, infectious diseases including tuberculosis, typhoid, hepatitis, sepsis, acute bacterial disease, severe mycobacterial or fungal disease, and mononucleosis, administration of myelotoxic and immunosuppressive agents including radiation, immunosuppressive drugs, and corticosteroids, cytotoxic chemotherapy or radiation therapy, infiltrative and hematological disorders including leukemia, myeloma, Hodgkin's disease and lymphoma, agranulocytosis and aplastic anemia, histocytosis and sarcoidosis, surgery and trauma including burns, splenectomy, and anesthesia, alcoholic cirrhosis, aging, anticonvulsant drugs, uremia, diabetes, vitamin and mineral deficiencies, and malnutrition. A patient suffering from neutropenia is at substantial risk for infection and disease, as the diminished number of neutrophils circulating in the blood substantially impairs the ability of the patient to fight any invading microorganisms.

The term "immunodeficiency disorders" refers to disorders or conditions characterized by a reduced or absent immune response. B cells, T cells, phagocytic cells, or complement may be deficient. The immunodeficiency disorder may be primary or secondary. Leukopenias, including lymphopenia, neutropenia, monocytopenia, and granulocytopenia, may be associated with primary or secondary immunodeficiency disorders. Examples of primary immunodeficiency disorders include, but are not limited to, B-cell deficiencies, including agammaglobulinemia and immunoglobulin deficiency (Ig) with hyper-IgM, T cell deficiencies including DiGeorge anomaly, chronic mucocutaneous candidiasis, combined immunodeficiency with Igs, nucleoside phosphorylase, and idiopathic CD4 lymphopenia, and combined T and B cell deficiencies including severe combined immunodeficiency, Wiskott-Aldrich syndrome, and X-linked lymphoproliferative syndrome. Examples of secondary immunodeficiency disorders include, but are not limited to, conditions associated with infectious diseases including human acquired immunodeficiency virus (HIV), hepatitis, influenza, tuberculosis, typhoid, sepsis, cytomegalovirus, acute bacterial disease, severe mycobacterial or fungal disease, congenital rubella, infectious mononucleosis, and viral exanthms, administration of myelotoxic and immunosuppressive agents including radiation, immunosuppressive drugs, and corticosteroids, cytotoxic chemotherapy, or radiation therapy, infiltrative and hematological disorders including leukemia, myeloma. Hodgkin's disease and lymphoma, agranulocytosis and aplastic anemia, histocytosis, and sarcoidosis, surgery and trauma including burns, splenectomy, and anesthesia, alcoholic cirrhosis, aging, anticonvulsant drugs, graft vs. host disease, uremia, diabetes, vitamin and mineral deficiencies, and malnutrition.

The term "autoimmune disorder" refers to disorders mediated by sustained adaptive immune responses to specific self antigens. Autoimmune disorders may be categorized by the class of hypersensitivity response associated with the disorder. Types I-III are antibody-mediated. Type I responses are mediated by IgE, which induces mast cell activation. Types II and III are mediated by IgG, which can activate either complement-mediated or phagocytic effector mechanisms. Type II responses are directed against cell-surface or matrix associated antigen leading to tissue damage. Type III responses are directed against soluble antigens and the tissue damage is caused by downstream responses triggered by immune complexes. Type IV responses are T lymphocyte mediated and can be subdivided into two classes. In the first class, tissue damage is caused by inflammatory T cells ($T_H1$ cells) mediated mainly by macrophages. In the second class, tissue damage is directly caused by cytotoxic T cells. Examples of autoimmune disorders include, but are not limited to, graft versus host disease, inflammatory bowel diseases including Crohn's disease and colitis, Guillain-Barre' syndrome, lupus, multiple sclerosis, myasthenia gravis, optic neuritis, psoriasis, rheumatoid arthritis, Graves disease, autoimmune hepatitis, type I diabetes, aplastic anemia, interstitial cystitis, scleroderma, vulvodynia, neuromyotonia, and vitiligo.

The "pathology" of a disease includes all phenomena that compromise the well-being of the patient. For cancer, this includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids: antioxidants including ascorbic acid: low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A "liposome" is a small vesicle composed of various types of lipids, phospholipids and/or surfactant which is useful for delivery of a drug (such as a Bv8 polypeptide or antibody thereto, an EG-VEGF polypeptide or antibody thereto, or combinations thereof) to a mammal. The components of the liposome are commonly arranged in a bilayer formation, similar to the lipid arrangement of biological membranes.

"small molecule" is defined herein to have a molecular weight below about 500 Daltons.

The terms "vascular endothelial growth factor", "VEGF", "VEGF polypeptide" and "VEGF protein" when used herein encompass native sequence VEGF and VEGF variants (which are further defined herein). The VEGF polypeptide may be isolated from a variety of sources, such as from human tissue types or from another source, or prepared by recombinant and/or synthetic methods.

A "native sequence VEGF" comprises a polypeptide having the same amino acid sequence as a VEGF derived from nature. Such native sequence VEGF can be isolated from nature or can be produced by recombinant and/or synthetic means. The term "native sequence VEGF" specifically encompasses naturally-occurring truncated or secreted forms (e.g., an extracellular domain sequence), naturally-occurring variant forms (e.g., alternatively spliced forms) and naturally-occurring allelic variants of the VEGF. In one embodiment of the invention, the native sequence VEGF is one of the five known isoforms, consisting of 121, 145, 165, 189, and 206 amino acid residues, respectively, as described, for example in U.S. Pat. Nos. 5,332,671 and 5,240,848: in PCT Publication No. WO 98/10071; Leung et al., 1989, *Science* 246:1306-1309; and Keck et al., 1989, *Science* 246:1309-1312.

"VEGF variant polypeptide" means an active VEGF polypeptide as defined below having at least about 80%, preferably at least about 85%, more preferably at least about 90%, event more preferably at least about 95%, most preferably at least about 98% amino acid sequence identity with the amino acid sequence of a native sequence VEGF. Such VEGF variant polypeptides include, for instance, VEGF polypeptides wherein one or more amino acid residues are added, or deleted, at the N- and/or C-terminus, as well as within one or more internal domains, of the native sequence. In one embodiment of the invention, VEGF is a receptor specific variant of native VEGF as described, for example, in PCT Publication Nos. WO 97/08313 and WO 00/63380 and U.S. Pat. No. 6,020,473.

The sequence identity (either amino acid or nucleic acid) for VEGF is determined using the same approach specifically described with regard to Bv8 or EG-VEGF. Similarly, the definitions provided for agonist and antagonists of Bv8 or EG-VEGF, including but not limited to antibodies, will apply to VEGF agonists and antagonists.

II. Methods for Carrying Out the Invention

The present invention is based on the identification of novel expression and activities of Bv8 and EG-VEGF in hematopoietic stem cells (HSCs), lineage-committed blood progenitor cells, and lymphocytes. In particular, as described in detail herein, Bv8, EG-VEGF, and their receptors are expressed in the HSCs in bone marrow, peripheral blood leukocytes (PBLs) as well as many hematological malignant cell lines. Both in vitro and in vivo experiments showed that Bv8 and EG-VEGF are capable of promoting colony formation of bone marrow mononuclear cells and spleen-derived committed mononuclear progenitor cells, increasing populations of white blood cells, and promoting activation of B lymphocytes and T lymphocytes. Accordingly, Bv8 nucleic acids and polypeptides, EG-VEGF nucleic acids and polypeptides, or combinations thereof can be used in a number of assays and in diagnosis and treatment of conditions associated with hematopoiesis, neutropenias, immunodeficiency disorders, and autoimmune disorders.

A. Hematopoiesis

Hematopoiesis refers to the proliferation and differentiation process, in which different types of blood cells develop from multipotent stem cells having the capacity to proliferate and differentiate. Most of the blood cells in the blood are short lived and thus need to be replaced constantly throughout life. The levels of mature blood cells in the circulation can change rapidly in response to different environmental stress ranging from blood loss, infections, and the like. The major site of hematopoiesis in humans, after about 20 weeks of fetal life, is the bone marrow (BM), a tissue consisting of a heterogeneous population of cells including hematopoietic stem cells (HSCs), endothelial cells (ECs), and other stromal cells as well as cells involved in bone homeostasis, including chondroclasts and osteoblasts. Gerber and Ferrara, 2003, *J. Mol. Med.*, 81:20-31.

Normal hematopoiesis is based on the dual functioning of multipotent stem cells. Extensive self-renewal maintains the population of undifferentiated stem cells, whereas differentiation results in the formation of various types of mature blood cells that are grouped into one of three major blood cell lineages: lymphoid, myeloid and erythroid cell lineages. The lymphoid lineage is comprised of B cells and T cells, which collectively function in antibody production and antigen detection, thereby functioning as a cellular and humoral immune system. The myeloid lineage is comprised of monocytes (macrophages), granulocytes (including neutrophils), and megakaryocytes, and monitors the bloodstream for antigens, scavenges antigens from the bloodstream, fights off infectious agents, and produces platelets that are involved in blood clotting. The erythroid lineage is comprised of red blood cells that carry oxygen throughout the body.

The hematopoietic stem cells as well as committed progenitor cells destined to become neutrophils, erythrocytes, platelets, and the like, may be distinguished from most other cells by the presence of the particular progenitor "marker" antigen that is present on the surface of these stem/progenitor cells. A group of antibodies capable of recognizing this particular marker antigen is referred to as "cluster of differentiation 34" or "CD34". The designation "CD34+" is used to describe a cell as one that has the particular cell surface antigen that is recognized by the CD34 group of antibodies. Stem cells, then, are CD34+. The majority of bone marrow cells that are CD34+, however, are B lymphocyte progenitor cells and myeloid progenitor cells.

1. Hematopoietic Factors

The development of early and differentiated hematopoietic cells is regulated by many hematopoietic growth factors, cytokines, and chemokines secreted by surrounding cells within the BM microenvironment as well as various non-hematopoietic organs (e.g., liver, kidney) and normal T lymphocytes. All these factors together modulate the biological functions and destinies of hematopoietic cells present in the BM. Janowska-Wieczorek et al., 2001, *Stem Cells*, 19:99-107.

At least four colony-stimulating factors (CSFs) are known to cooperate in the regulation of neutrophil production. These four factors, referred to as GM-CSF (granulocyte and macrophage), IL-3 (interleukin-3), G-CSF (granulocyte), and M-CSF (macrophage), that is also known as CSF-1, are synthesized by macrophages, T cells, endothelial cells and other types of cells. The potential of a progenitor cell to respond to a CSF is determined, in part, by the presence of receptors on the surface of the cell for that particular CSF and, in part, by the concentration of the particular CSF. There also is some indication for indirect stimulation, whether via an accessory cell or by synergistic action with other obligatory growth factors, such as c-kit ligand, IL-6 (interleukin-6), IL-11 (interleukin-11), IL-4 (interleukin-4), and IL-1 (interleukin-1).

2. Neutrophils

The main infection and disease-fighting cells of the human immune system are the white blood cells (leukocytes), which are originated from the myeloid lineage and circulate through the blood system. Of the many types of leukocytes, the neutrophil, a subtype of granulocyte that contains an oddly shaped nucleus and a highly granulated cytoplasm, is the most common cell type and accounts for about two thirds of the entire white blood cell population in humans. Neutrophils are mobile, responsive to chemotactic stimuli generated upon infection, and capable of moving into infected tissues to kill the invading microorganisms. The killing depends on the ability of the neutrophils to engulf the microorganisms and to release oxygen radicals and microbicidal enzymes. Baggiolini, 1984, *Experientia*, 40:906-909.

Neutrophils differentiate from stem cells through a series of intermediate precursor cells, which can be distinguished by their microscopic morphological appearance, including such characteristics as the size of their nuclei, the shape of their nuclei, cell size, nuclear/cytoplasmic ratio, presence/absence of granules, and staining characteristics. Initially, the multipotent stem cell, which cannot be measured directly in vitro, gives rise to myeloid "progenitor cells" that generate precursors for all myeloid cell lines. The first myeloid progenitor is designated CFU-GEMM for "colony forming unit—granulocyte, erythroid, macrophage and megakaryocyte". The CFU-GEMM progenitor, in turn, will give rise to a CFU-GM progenitor cell, which is otherwise known as "colony forming unit—granulocyte and macrophage". In all of these descriptive terms, "colony" refers to a cell that is capable of giving rise to more than 50 cells as measured in 14 day in vitro assays for clonal growth, under conditions as set forth in Example 5 of the present specification. These cells will divide at least six times.

The CFU-GM is a committed progenitor; it is committed to differentiating into granulocytes and macrophages only. It is not capable of differentiating into other types of cells nor is it capable of dedifferentiating into earlier stage progenitor cells. The CFU-GM progenitor cell may then differentiate into a myeloblast. The time required for differentiation from a CFU-GEMM to a myeloblast is believed to be about 1-4 days. A myeloblast is the first of the series of cells that may be referred to as "precursors" to the neutrophils, as such cells, once allowed to fully develop (differentiate), can only form neutrophils. Neutrophils are only capable of undergoing fewer than six cell divisions and, therefore, do not form colonies in in vitro colony assays as described previously.

Once differentiation has progressed to the myeloblast stage, the myeloblasts undergo terminal differentiation into promyelocytes, which in turn differentiate into myelocytes over a course of about 4-6 days. Within another 5 days or so, myelocytes differentiate into metamyelocytes, which in turn differentiate into banded neutrophils. These banded neutrophils finally differentiate into mature, segmented neutrophils, which have a half-life of about 0.3 to 2 days. The term "progenitor" will be used to refer to stem cells, and cells that can form colonies. "Precursor" will be used to refer to myeloblasts, promyelocytes and myelocytes and, in some instances, metamyelocytes and banded neutrophils.

During this progressive, morphologic differentiation, changes in the surface antigens of the precursor cells can be observed. For example, stem cells, CFU-GEMM and CFU-GM are CD34+. Hematopoietic cells that differentiate beyond the CFU-GM stage are no longer CD34+. Similar progressions of expression are observed for the cell-surface antigens CD33 and CD45RA. All neutrophil precursor cells subsequent to the promyelocyte precursor cells may be characterized as CD34−, CD33+, CD38+, CD13+, CD45RA−, and CD15+. More mature cells also may be characterized as CD11+ and CD16+(Terstappen et al., 1990, Leukemia, 4:657). It should be appreciated, however, that such transitions in cell-surface antigen expression are gradual, rather than abrupt, wherein some cells of a particular precursor cell type may be positive and other cells of the same type may be negative for a particular cell-surface antigen. Furthermore, the determination that a particular cell type is positive or negative for a particular cell-surface antigen will depend, in part, upon the particular method used to make that determination. The characterization of cell differentiation by cell-surface antigen expression may be confirmed by other means of characterizing cell differentiation, such as cell morphology.

"Neutropenia" is a condition characterized by an abnormally low number of circulating neutrophils. A patient suffering from neutropenia is at substantial risk for infection and disease, as the diminished number of neutrophils circulating in the blood substantially impairs the ability of the patient to fight any invading microorganisms. Neutropenia itself may be the result of disease, genetic disorders, drugs, toxins, and radiation as well as many therapeutic treatments, such as high dose chemotherapy (HDC) and conventional oncology therapy. For example, although many cancers have been found to be sensitive to extremely high doses of radiation or anti-neoplastic (anti-cancer) drugs, such intensive HDC is not widely used because it not only kills cancerous cells, but also frequently destroys the cells of the hematopoietic system that are responsible for generating the army of neutrophils that are necessary to maintain a functioning immune system. Complete destruction of neutrophil progenitor and precursor cells eliminates the patient's short-term capacity to generate mature neutrophils, thereby severely compromising the patient's ability to combat infection. The patient then becomes "immunocompromised" and subject to opportunistic infection. Such a condition may ultimately result in morbidity and death. Other situations also may be encountered where there has been a severe insult to the hematopoietic system, resulting in a substantial reduction in neutrophils and precursors thereto.

3. Hematological Disorders

Hematological disorders are characterized by abnormal proliferation and differentiation of blood cells, which can lead to dysplastic changes in blood cells and hematologic malignancies. Development of many hematological disorders is a clonal process, in which one cell type predominates. In some instances, other cell types also develop abnormally. Furthermore, the abnormal cells of a particular disorder represent clonal derivatives of undifferentiated hematopoietic progenitors, either multipotent stem cells or lineage-committed precursor cells. Gerber and Ferrara, 2003, *J. Mol. Med.*, 81:20-31; Raskind et al., 1998, *Leukemia*, 12:108-116. Many hematological disorders can be classified as leukemias, myeloproliferative disorders (MPDs) and myelodysplastic disorders. Many of these disorders can occur in adults as well as children.

Acute myeloid leukemia (AML) is the most common type of acute leukemia that occurs in adults. Several inherited genetic disorders and immunodeficiency states are associated with an increased risk of AML. These include disorders with defects in DNA stability, leading to random chromosomal breakage, such as Bloom's syndrome, Fanconi's anemia, Li-Fraumeni kindreds, ataxia-telangiectasia, and X-linked agammaglobulinemia. Cytoarabine (Ara-C) has been used alone or in combination with anthracycline or daunorubicin to treat AML.

Acute lymphoblastic leukemia (ALL) is a heterogeneous disease with distinct clinical features displayed by various subtypes. Reoccurring cytogenetic abnormalities have been demonstrated in ALL. The most common cytogenetic abnormality involves translocation of chromosome 9 and 22. The resultant Philadelphia chromosome represents poor prognosis for the patient. Vincristine, anthracyclines, and prednisone have been used to treat ALL.

The myeloproliferative disorders (MPD) are characterized by abnormal proliferation of hematopoietic cells. In each specific MPD, one particular cell type predominates, but there is evidence that some or all the other BM cell types are also proliferating abnormally to a lesser extent. For example, chronic myelogenous leukemia (CML) is a clonal MPD of a pluripotent stem cell. CML is characterized by the presence of large numbers of abnormal mature granulocytes, circulating in the blood, due to a specific chromosomal abnormality involving the translocation of chromosomes 9 and 22, creating the Philadelphia chromosome. Ionizing radiation is associated with the development of CML. Hydroxyurea, interferon (INF) and Ara-C have been used to treat patients with CML. Other typical MPDs include, but not limited to, polycythemia vera (PV; over proliferation of red blood cells), essential thrombocythemia (ET; over proliferation of platelets) and myeloid metaplasia (also known as myelofibrosis).

The myelodysplastic syndromes (MDS) are heterogeneous clonal hematopoietic stem cell disorders grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS typically develop complications related to anemia, neutropenia (infections), or thrombocytopenia (bleeding). Generally, from about 10% to about 70% of patients with MDS develop acute leukemia.

B. Bv8 and EG-VEGF

Bv8 is a small protein that was originally isolated from the skin secretions of the frog *Bombina variegata* (Mollay et al., 1999, *Eur. J. Pharmacol.*, 374:189-196). Bv8 belongs to a structurally related class of peptides including the digestive enzyme colipase, the *Xenopus* head-organizer, Dickkopf (Glinka et al., 1998, *Nature*, 391:357-362), venom protein A (VPRA) (Joubert and Strydom, 1980, *Hopper-Seyler's Z. Physiol. Chem.*, 361:1787-1794) or MIT-1 (Schweitz et al. 1999, *FEBS Lett.*, 461:183-188), a nontoxic component of *Dendroaspis polylepis polylepis* venom, and the recently identified endocrine-gland-derived vascular endothelial growth factor (EG-VEGF) (LeCouter et al., *Nature*, 412:877-884 (2001)). A distinguishing structural motif is a colipase-fold, where 10 cysteine residues form five disulfide bridges within a conserved span. EG-VEGF (80% identical to VPRA) and VPRA are most closely related to the Bv8 peptide, with 83% and 79% identity, respectively. Mouse and human orthologues of Bv8, also known as prokineticin-2 (PK2) (Li et al., 2001, *Pharm* 59:69-698), have been recently identified, and a variety of activities for these proteins have been reported, including effects on neuronal survival, gastrointestinal smooth muscle contraction, and circadian locomotor rhythm. Li et al., 2001: Melchiorri et al., 2001, *Eur. J. Neurosci.* 13:1694-1702; Cheng et al., 2002, *Nature* 417:405-410.

Both EG-VEGF and Bv8 have been identified as angiogenic factors with selective activities for endothelial cells of specific tissues. The diverse structural and functional properties of endothelial cells, and evidence from a variety of in vivo and ex vivo systems, suggest the existence of local, tissue-specific regulators of endothelial cell phenotype and growth. Expression of human (h)EG-VEGF mRNA was found principally restricted to the steroidogenic glands: ovary, testis, adrenal, and placenta. EG-VEGF promoted proliferation, migration, survival, and fenestration in cultured adrenal capillary endothelial cells. It also induced extensive angiogenesis when delivered to the ovary, but not other tissues. LeCouter et al., 2001, *Nature*, 412:877-884.

Bv8 has been found expressed predominantly in the testis and is largely restricted to primary spermatocytes (LeCouter et al., 2003, *PNAS* 5:2685-2690. Like EG-VEGF, Bv8 is able to induce proliferation, survival, and migration of adrenal cortical capillary endothelial cells. Bv8 gene expression is induced by hypoxic stress. Adenoviral delivery of Bv8 or EG-VEGF to mouse testis resulted in a potent angiogenic response. Furthermore, expression within the testis of two G protein-coupled receptors for Bv8/EG-VEGF, Bv8/EG-VEGF receptor-1 and Bv8/EG-VEGF receptor-2, was localized to vascular endothelial cells (LeCouter et al., 2003, *Proc. Natl. Acad. Sci. USA,* 100:2685-2690; Lin et al., 2002, *J. Biol. Chem.* 277:19276-19280; Masuda et al., 2002, *Biochem. Biophys. Res. Commun.* 293:396-402). The testis exhibits relatively high turnover of endothelial cells. Thus, Bv8 and EG-VEGF, along with other factors such as VEGF, are considered to be important in maintaining the integrity and regulating proliferation of the blood vessels in the testis.

C. Identification of Bv8 and EG-VEGF Variants

In addition to the full-length native sequence Bv8 and EG-VEGF polypeptides described herein, it is contemplated that Bv8 and EG-VEGF variants can be identified, prepared and used in the present invention. Bv8 and EG-VEGF variants can be prepared by introducing appropriate nucleotide changes into the Bv8 or EG-VEGF DNA, and/or by synthesis of the desired Bv8 or EG-VEGF polypeptide. Those skilled in the art will appreciate that amino acid changes may alter post-translational processes of the Bv8 or EG-VEGF, such as changing the number or position of glycosylation sites. Methods for producing Bv8 and EG-VEGF variants are preferably the same as for producing native sequence Bv8 and EG-VEGF as described in detail below, substituting the polynucleotide encoding the variant for the polynucleotide encoding the native sequence.

Polynucleotide molecules that encode Bv8 or EG-VEGF are used in the methods of the present invention. cDNAs encoding two full-length variants of human Bv8 are provided in FIGS. 1 and 2 (SEQ ID NOS: 1 and 2), and the corresponding deduced amino acid sequences are provided in FIGS. 2 and 4 (SEQ ID NOS: 2 and 4). A cDNA encoding mouse Bv8 is provided in FIG. 5 (SEQ ID NO: 5) and the corresponding deduced amino acid sequence is provided in FIG. 6 (SEQ ID NO: 6). cDNAs encoding two full length native EG-VEGFs (SEQ ID NOS:7 and 9) and the corresponding deduced amino acid sequences (SEQ ID NOS: 8 and 10) are useful in the methods of the present invention. The polynucleotides used in the present invention can be obtained using standard techniques well known to those skilled in the art such as, for example, hybridization screening and PCR methodology.

Any nucleotide sequence that encodes the amino acid sequence of Bv8 or EG-VEGF can be used to generate recombinant molecules that direct the expression of Bv8 or EG-VEGF, respectively. The methods of the present invention may also utilize a fusion polynucleotide between a Bv8 or EG-VEGF coding sequence and a second coding sequence for a heterologous protein.

In order to clone full length homologous cDNA sequences from any species encoding the entire Bv8 or EG-VEGF cDNA, or to clone family members or variant forms such as allelic variants, labeled DNA probes made from fragments corresponding to any part of the cDNA sequences disclosed herein may be used to screen a cDNA library derived from a cell or tissue type believed to express Bv8 or EG-VEGF. More specifically, oligonucleotides corresponding to either the 5' or 3' terminus of the coding sequence may be used to obtain longer nucleotide sequences.

It may be necessary to screen multiple cDNA libraries from different tissues to obtain a full-length cDNA. In the event that it is difficult to identify cDNA clones encoding the complete 5' terminal coding region, an often encountered situation in cDNA cloning, the RACE (Rapid Amplification of cDNA Ends) technique may be used. RACE is a proven PCR-based strategy for amplifying the 5' end of incomplete cDNAs. 5'-RACE -Ready RNA synthesized from human placenta containing a unique anchor sequence is commercially available (Clontech). To obtain the 5' end of the cDNA, PCR is carried out on 5'-RACE-Ready cDNA using the provided anchor primer and the 3' primer. A secondary PCR is then carried out using the anchored primer and a nested 3' primer according to the manufacturer's instructions. Once obtained, the full length cDNA sequence may be translated into amino acid sequence and examined for certain landmarks such as a continuous open reading frame flanked by translation initiation and termination sites, a potential signal sequence and finally overall structural identity to the Bv8 and/or EG-VEGF sequences disclosed herein.

Alternatively, a labeled probe may be used to screen a genomic library derived from any organism of interest using appropriate stringent conditions as described infra.

Isolation of a Bv8 or EG-VEGF coding sequence or a homologous sequence may be carried out by the polymerase chain reactions (PCR) using two degenerate oligonucleotide primer pools designed on the basis of the Bv8 or EG-VEGF coding sequences disclosed herein. The template for the reaction may be cDNA obtained by reverse transcription (RT) of mRNA prepared from, for example, human or non-human cell lines or tissues known or suspected to express a Bv8 gene allele or an EG-VEGF gene allele.

The PCR product may be subcloned and sequenced to ensure that the amplified sequences represent the sequences of a Bv8 or EG-VEGF coding sequence. The PCR fragment may then be used to isolate a full-length cDNA clone by a variety of methods. For example, the amplified fragment may be labeled and used to screen a bacteriophage cDNA library. Alternatively, the labeled fragment may be used to isolate genomic clones via the screening of a genomic library.

PCR technology may also be utilized to isolate full-length cDNA sequences. For example, RNA may be isolated, following standard procedures, from an appropriate cellular or tissue source. An RT reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated.

A cDNA clone of a mutant or allelic variant of the Bv8 or EG-VEGF gene may be isolated, for example, by using PCR. In this case, the first cDNA strand may be synthesized by hybridizing an oligo-dT oligonucleotide to mRNA isolated from tissue known or suspected to express Bv8. EG-VEGF, or a combination thereof in an individual putatively carrying the mutant Bv8 allele, mutant EG-VEGF allele, or combinations thereof, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant Bv8 or EG-VEGF allele to that of the normal Bv8 or EG-VEGF allele, the mutation(s) responsible for the loss or alteration of function of the mutant Bv8 or EG-VEGF gene product can be ascertained.

Alternatively, a genomic library can be constructed using DNA obtained from an individual suspected of or known to carry a mutant Bv8 allele or mutant EG-VEGF allele, or a cDNA library can be constructed using RNA from a tissue known, or suspected, to express a mutant Bv8 allele or mutant EG-VEGF allele. An unimpaired Bv8 or EG-VEGF gene or any suitable fragment thereof may then be labeled and used as a probe to identify the corresponding mutant Bv8 or EG-VEGF allele in such libraries. Clones containing the mutant Bv8 gene sequences or mutant EG-VEGF gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant Bv8 allele or mutant EG-VEGF allele in an individual suspected of or known to carry such a mutant allele. In this manner, gene products made by the putatively mutant tissue may be expressed and screened using standard antibody screening techniques in conjunction with antibodies raised against the normal Bv8 or EG-VEGF gene product, as described, below.

As used herein, the terms nucleic acid, polynucleotides and nucleotide are interchangeable, and refer to any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages.

The terms nucleic acid, polynucleotide, and nucleotide also specifically include nucleic acids composed of bases other than the five biologically occurring bases (adenine, guanine, thymine, cytosine, and uracil). For example, a polynucleotide of the invention might contain at least one modified base moiety which is selected from the group including, but not limited to 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2.2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

Furthermore, a polynucleotide used in the invention may comprise at least one modified sugar moiety selected from the group including but not limited to arabinose, 2-fluoroarabinose, xylulose, and hexose.

It is not intended that the methods of the present invention be limited by the source of the polynucleotide. The polynucleotide can be from a human or non-human mammal, derived from any recombinant source, synthesized in vitro or by chemical synthesis. The nucleotide may be DNA or RNA and may exist in a double-stranded, single-stranded or partially double-stranded form.

Nucleic acids useful in the present invention include, by way of example and not limitation, oligonucleotides such as antisense DNAs and/or RNAs; ribozymes; DNA for gene therapy; DNA and/or RNA chimeras; various structural forms of DNA including single-stranded DNA, double-stranded DNA, supercoiled DNA and/or triple-helix DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, *Oligonucleotide Synthesis: A Practical Approach*, IRL Press, Oxford, England). RNAs may be produced in high yield via in vitro transcription using plasmids such as SP65 (Promega Corporation, Madison, Wis.).

Any mRNA transcript encoded by Bv8 or EG-VEGF nucleic acid sequences may be used in the methods of the present invention, including, in particular, mRNA transcripts resulting from alternative splicing or processing of mRNA precursors.

In some circumstances, such as where increased nuclease stability is desired, nucleic acids having modified internucleoside linkages may be preferred. Nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—$CH_2$—S—$CH_2$—), dimethylene-sulfoxide (—$CH_2$—SO—$CH_2$—), dimethylene-sulfone (—$CH_2$—$SO_2$—$CH_2$—), 2'-O-alkyl, and 2'-deoxy-2'-fluoro phosphorothioate internucleoside linkages are well known in the art (see Uhlmann et al., 1990, *Chem. Rev.*, 90:543-584; Schneider et al., 1990, *Tetrahedron Lett.*, 31:335 and references cited therein).

In some embodiments of the present invention, the nucleotide used is an α-anomeric nucleotide. An α-anomeric nucleotide forms specific double-stranded hybrids with complementary RNA in which, contrary to the usual β-units, the strands run parallel to each other (Gautier et al., 1987, *Nucl. Acids Res.* 15:6625-6641). The nucleotide is a 2'-O-methylribonucleotide (Inoue et al., 1987, *Nucl. Acids Res.* 15:6131-6148), or a chimeric RNA-DNA analogue (Inoue et al., 1987, *FEBS Lett.* 275:327-330).

The nucleic acids may be purified by any suitable means, as are well known in the art. For example, the nucleic acids can be purified by reverse phase or ion exchange HPLC, size exclusion chromatography, or gel electrophoresis. Of course, the skilled artisan will recognize that the method of purification will depend in part on the size of the DNA to be purified.

Isolated or purified polynucleotides having at least 10 nucleotides (i.e., a hybridizable portion) of a Bv8 coding sequence, EG-VEGF coding sequence, a combination thereof, or the complement thereof, may also be used in the methods of the present invention. In other embodiments, the polynucleotides contain at least 25 (continuous) nucleotides, 50 nucleotides, 100 nucleotides, 150 nucleotides, or 200 nucleotides of a Bv8 coding sequence, EG-VEGF coding sequence, or a combination thereof, or a full-length Bv8 coding sequence, EG-VEGF coding sequence, or a combination thereof. Nucleic acids can be single or double stranded. Additionally, the invention provides to polynucleotides that selectively hybridize to a complement of the foregoing coding sequences. In preferred embodiments, the polynucleotides contain at least 10, 25, 50, 100, 150 or 200 nucleotides, or the entire length of a Bv8 coding sequence, EG-VEGF coding sequence, or a combination thereof.

Nucleotide sequences that encode a mutant of Bv8 or EG-VEGF peptide fragments of Bv8 or EG-VEGF truncated forms of Bv8 or EG-VEGF, and Bv8 fusion proteins or EG-VEGF fusion proteins may also be useful in the methods of the present invention. Nucleotides encoding fusion proteins may include, but are not limited to full length Bv8 sequences or EG-VEGF sequences truncated forms of Bv8 or EG-VEGF or nucleotides encoding peptide fragments of Bv8 or EG-VEGF fused to an unrelated protein or peptide, such as for example, a domain fused to an Ig Fc domain that increases the stability and half life of the resulting fusion protein (for example, Bv8-Ig or EG-VEGF-Ig) in the bloodstream; or an enzyme such as a fluorescent protein or a luminescent protein that can be used as a marker.

Furthermore, Bv8 and EG-VEGF polynucleotide variants that have been generated, at least in part, by some form of directed evolution, for example, gene shuffling and/or recursive sequence recombination described in U.S. Pat. Nos. 5,605,793 and 5,837,458, incorporated by reference herein in their entirety, may be used in the methods of the present invention. For example, using such techniques, a Bv8 encoding sequence and/or EG-VEGF encoding sequence, or a plurality of Bv8 and/or EG-VEGF encoding sequences can be used as the starting point for the generation of novel sequences encoding functionally and/or structurally similar proteins with altered functional and/or structural characteristics.

Highly related gene homologs of the Bv8 and/or EG-VEGF encoding polynucleotide sequences described above may also be useful in the present invention. Highly related gene homologs are polynucleotides encoding proteins that have at least about 60% amino acid sequence identity with the amino acid sequence of a naturally occurring Bv8 or EG-VEGF such as the mature human Bv8 of FIG. 2 or FIG. 4 (SEQ ID NOs:2 and 4), and mature human EG-VEGF (SEQ ID NO:8), preferably at least about 65%, 70%, 75%, or 80% amino acid sequence identity, with increasing preference of at least about 85% to at least about 99% amino acid sequence identity, in 1% increments. Highly related homologs can encode proteins sharing functional activities with Bv8 and/or EG-VEGF.

The methods of the present invention also benefit by the use of (a) DNA vectors that contain any of the foregoing Bv8 or EG-VEGF coding sequences and/or their complements (i.e., antisense); (b) DNA expression vectors that contain any of the foregoing Bv8 or EG-VEGF coding sequences operatively associated with a regulatory element that directs the expression of the coding sequences; (c) genetically engineered host cells that contain any of the foregoing Bv8 and/or EG-VEGF coding sequences, or combinations thereof operatively associated with a regulatory element that directs the expression of the coding sequences in the host cell; and (d) genetically engineered host cells that express an endogenous Bv8 gene or EG-VEGF gene under the control of an exogenously introduced regulatory element (i.e., gene activation).

Variations in native sequence Bv8 or EG-VEGF or in various domains of the Bv8 or EG-VEGF described herein, can be made, for example, using any of the techniques and guidelines for conservative and non-conservative mutations set forth, for instance, in U.S. Pat. No. 5,364,934. Variations may be a substitution, deletion or insertion of one or more codons encoding Bv8 or EG-VEGF that results in a change in the amino acid sequence of the Bv8 or EG-VEGF as compared with native sequence Bv8 or EG-VEGF. Optionally the variation is by substitution of at least one amino acid with any other amino acid in one or more of the domains of the Bv8 or EG-VEGF. Guidance in determining which amino acid residue may be inserted, substituted or deleted without adversely affecting the desired activity may be found by comparing the sequence of Bv8 or EG-VEGF with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Bv8 polypeptide fragments and EG-VEGF polypeptide fragments are also useful in the methods of the present invention. Such fragments may be truncated at the N-terminus or C-terminus, or may lack internal residues, for example, when compared with a full-length native protein. Certain fragments lack amino acid residues that are not essential for a desired biological activity of the Bv8 polypeptide or EG-VEGF polypeptide.

Bv8 fragments and EG-VEGF fragments may be prepared by any of a number of conventional techniques. Desired peptide fragments may be chemically synthesized. An alternative approach involves generating Bv8 or EG-VEGF fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment by polymerase chain reaction (PCR). Oligonucleotides that define the desired termini of the DNA fragment are employed at the 5' and 3' primers in the PCR. Preferably, Bv8 or EG-VEGF polypeptide fragments share at least one biological and/or immunological activity with a native Bv8 polypeptide and/or native EG-VEGF polypeptide, respectively.

In particular embodiments, conservative substitutions of interest are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
| --- | --- | --- |
| Ala(A) | val: leu; ile | val |
| Arg(R) | lys; gin; asn | lys |
| Asn(N) | gln; his; lys; arg | gln |
| Asp(D) | glu | glu |
| Cys(C) | ser | ser |
| Gln(Q) | asn | asn |
| Glu(E) | asp | asp |
| Gly(G) | pro; ala | ala |
| His(H) | asn; gln; lys; arg | arg |
| Ile(I) | leu; val; met; ala; phe; norleucine | leu |
| Leu(L) | norleucine; ile; val met; ala; phe | ile |
| Lys(K) | arg; gln; asn | arg |
| Met(M) | leu; phe; ile | leu |
| Phe(F) | leu; val; ile; ala; tyr | leu |
| Pro(P) | ala | ala |
| Ser(S) | thr | thr |
| Thr(T) | ser | ser |
| Trp(W) | tyr; phe | tyr |
| Tyr(Y) | trp; phe; thr; ser | phe |
| Val(V) | ile; leu; met; phe ala; norleucine | leu |

Substantial modifications in function or immunological identity of the Bv8 polypeptide or EG-VEGF polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis (Carter et al., 1986, *Nucl. Acids Res.*, 13:4331; Zoller et al., 1987, *Nucl. Acids Res.*, 10:6487), cassette mutagenesis (Wells et al., 1985, *Gene*, 34:315), restriction selection mutagenesis (Wells et al., 1986, *Philos. Trans. R. Soc. London Ser A*, 317:415) or other known techniques can be performed on cloned DNA to produce the Bv8 variant DNA and/or EG-VEGF variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells, 1989, *Science*, 244:1081-1085). Alanine is also typically preferred because it is the most common amino acid. Further, it is frequently found in both buried and exposed positions (Creighton, *The Proteins*, (W.H. Freeman & Co., N.Y.); Chothia, 1976, *J. Mol. Biol.*, 150:1). If alanine substitution does not yield adequate amounts of variant, an isoteric amino acid can be used.

D. Production of Bv8, EG-VEGF, and Variants Thereof

Techniques suitable for the production of Bv8, EG-VEGF, and variants thereof are well known in the art. Because the preferred techniques are the same for native polypeptides and variants, the techniques described below apply to Bv8 and EG-VEGF variants as well as to native sequence Bv8 and EG-VEGF, respectively.

The preferred methods of production include isolating Bv8 or EG-VEGF from an endogenous source of the polypeptide, peptide synthesis (using a peptide synthesizer), recombinant techniques, or any combination of these techniques.

Most of the discussion below pertains to recombinant production of Bv8 or EG-VEGF by culturing cells transformed with a vector containing Bv8 nucleic acid, EG-VEGF nucleic acid, or a combination thereof and recovering the polypeptide from the cell culture. However, one of skill in the art will recognize that there are many ways of producing Bv8 and EG-VEGF.

Briefly, this method involves transforming primary human cells containing an Bv8-encoding gene or EG-VEGF encoding gene with a construct (i.e., vector) comprising an amplifiable gene (such as dihydrofolate reductase (DHFR) or others discussed below) and at least one flanking region of a length of at least about 150 bp that is homologous with a DNA sequence at the locus of the coding region of the Bv8 gene or EG-VEGF gene to provide amplification of the Bv8 gene or EG-VEGF. The amplifiable gene must be at a site that does not interfere with expression of the Bv8 or EG-VEGF gene. The transformation is conducted such that the construct becomes homologously integrated into the genome of the primary cells to define an amplifiable region.

Primary cells comprising the construct are then selected for by means of the amplifiable gene or other marker present in the construct. The presence of the marker gene establishes the presence and integration of the construct into the host genome. No further selection of the primary cells need be made, since selection will be made in the second host. If desired, the occurrence of the homologous recombination event can be determined by employing PCR and either sequencing the resulting amplified DNA sequences or determining the appropriate length of the PCR fragment when DNA from correct homologous integrants is present and expanding only those cells containing such fragments. Also if desired, the selected cells may be amplified at this point by stressing the cells with the appropriate amplifying agent (such as methotrexate if the amplifiable gene is DHFR), so that multiple copies of the target gene are obtained. Preferably, however, the amplification step is not conducted until after the second transformation described below.

After the selection step, DNA portions of the genome, sufficiently large to include the entire amplifiable region, are isolated from the selected primary cells. Secondary mammalian expression host cells are then transformed with these genomic DNA portions and cloned, and clones are selected that contain the amplifiable region. The amplifiable region is then amplified by means of an amplifying agent if not already amplified in the primary cells. Finally, the secondary expression host cells now comprising multiple copies of the amplifiable region containing Bv8 or EG-VEGF are grown so as to express the gene and produce the protein.

The DNA encoding Bv8 or EG-VEGF may be obtained from any cDNA library prepared from tissue believed to possess Bv8 mRNA or EG-VEGF mRNA, respectively, and to express it at a detectable level. Accordingly, Bv8 or EG-VEGF DNA can be conveniently obtained from a cDNA library prepared, for example, from multiple human tissues. The Bv8-encoding gene or EG-VEGF-encoding gene may also be obtained from a genomic library or by oligonucleotide synthesis.

Libraries are screened with probes (such as antibodies to Bv8 or EG-VEGF or oligonucleotides of about 20-80 bases) designed to identify the gene of interest or the protein encoded by it. Screening the cDNA or genomic library with the selected probe may be conducted using standard procedures as described in chapters 10-12 of Sambrook et al., *Molecular Cloning: A Laboratory Manual* (New York: Cold Spring Harbor Laboratory Press, 1989). An alternative means to isolate the gene encoding Bv8 or the gene encoding EG-VEGF is to use PCR methodology as described in section 14 of Sambrook et al., supra.

A preferred method of isolating Bv8 and/or EG-VEGF cDNA is to use carefully selected oligonucleotide sequences to screen cDNA libraries from various human tissues. The oligonucleotide sequences selected as probes should be of sufficient length and sufficiently unambiguous that false positives are minimized. Preferred sequences are obtained from the naturally occurring Bv8 or EG-VEGF disclosed herein.

The oligonucleotide must be labeled such that it can be detected upon hybridization to DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

The nucleic acid (e.g., cDNA or genomic DNA) encoding Bv8 or EG-VEGF is inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

Bv8 or EG-VEGF useful in this invention may be produced recombinantly not only directly, but also as a fusion polypeptide with a heterologous polypeptide. The heterologous polypeptide is preferably a signal sequence or other polypeptide having a specific cleavage site at the N-terminus of the mature protein or polypeptide. In general, the signal sequence may be a component of the vector, or it may be a part of the Bv8 DNA or EG-VEGF DNA that is inserted into the vector. The heterologous signal sequence selected preferably is one that is recognized and processed (i.e., cleaved by a signal peptidase) by the host cell. For prokaryotic host cells that do not recognize and process the native Bv8 signal sequence or EG-VEGF signal sequence, the signal sequence is substituted by a prokaryotic signal sequence selected, for example, from the group consisting of the alkaline phosphatase, penicillinase, lpp, and heat-stable enterotoxin II leaders. For yeast secretion the native signal sequence may be substituted by, e.g., the yeast invertase leader, a factor leader (including *Saccharomyces* and *Kluveromyces* α-factor leaders, the latter described in U.S. Pat. No. 5,010,182 issued 23 Apr. 1991), or acid phosphatase leader, the *C. albicans* glucoamylase leader (EP 362,179 published 4 Apr. 1990), or the signal described in WO 90/13646 published 15 Nov. 1990. For mammalian cell expression, the native signal sequence (e.g., the Bv8 or EG-VEGF presequence that normally directs secretion of Bv8 or EG-VEGF from human cells in vivo) is satisfactory, although other mammalian signal sequences may be suitable, such as signal sequences from other animal Bv8 or EG-VEGF polypeptides, and signal sequences from secreted polypeptides of the same or related species, as well as viral secretory leaders, for example, the herpes simplex gD signal.

The DNA for such precursor region is ligated in reading frame to DNA encoding the mature Bv8 or EG-VEGF, or a soluble variant thereof.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 μplasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, that is, they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using *Bacillus* species as hosts, for example, by including in the vector a DNA sequence that is complementary to a sequence found in *Bacillus* genomic DNA. Transfection of *Bacillus* with this vector results in homologous recombination with the genome and insertion of Bv8 DNA and/or EG-VEGF DNA. However, the recovery of genomic DNA encoding Bv8 or EG-VEGF is more complex than that of an exogenously replicated vector because restriction enzyme digestion is required to excise the Bv8 and/or EG-VEGF DNA.

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the Bv8 or EG-VEGF nucleic acid, such as DHFR or thymidine kinase. The mammalian cell transformants are placed under selection pressure such that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes Bv8 and/or EG-VEGF. Amplification is the process by which genes in greater demand for the production of a protein critical for growth are reiterated in tandem within the chromosomes of successive generations of recombinant cells. Increased quantities of Bv8 and/or EG-VEGF are synthesized from the amplified DNA. Other examples of amplifiable genes include metallothionein-I and -II, preferably primate metallothionein genes, adenosine deaminase, ornithine decarboxylase, etc. A preferred vector system is provided in U.S. Pat. No. 5,561,053.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub et al., *Proc. Natl. Acad. Sci. USA*, 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding Bv8 and/or EG-VEGF. This amplification technique can be used with any otherwise suitable host, for example, ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding Bv8 and/or EG-VEGF wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See, for example, U.S. Pat. No. 4,965,199.

A suitable selection gene for use in yeast is the trp1 gene present in the yeast plasmid YRp7 (Stinchcomb et al., 1979, *Nature*, 282:39). The trp1 gene provides a selection marker for a mutant strain of yeast lacking the ability to grow in tryptophan, for example, ATCC No. 44076 or PEP4-1. Jones, 1977, *Genetics*, 85:12. The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 µm circular plasmid pKD 1 can be used for transformation of *Kluyveromyces* yeasts. Bianchi et al., 1987, *Curr. Genet.*, 12:185. More recently, an expression system for large-scale production of recombinant calf chymosin was reported for *K. lactis*. Van den Berg, 1990, *Bio/Technology*, 8:135. Stable multi-copy expression vectors for secretion of mature recombinant human serum albumin by industrial strains of *Kluyveromyces* have also been disclosed. Fleer et al., 1991, *Bio/Technology*, 9:968-975.

Expression and cloning vectors usually contain a promoter that is recognized by the host organism and is operably linked to the Bv8 and/or EG-VEGF nucleic acid. Promoters are untranslated sequences located upstream (5') to the start codon of a structural gene (generally within about 100 to 1000 bp) that control the transcription and translation of particular nucleic acid sequence, such as the Bv8 and/or EG-VEGF nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to Bv8-encoding DNA and/or EG-VEGF encoding DNA by removing the promoter from the source DNA by restriction enzyme digestion and inserting the isolated promoter sequence into the vector. The native Bv8 promoter sequence, native EG-VEGF promoter sequence, and many heterologous promoters may be used to direct amplification and/or expression of the Bv8 DNA or EG-VEGF DNA, respectively. However, heterologous promoters are preferred, as they generally permit greater transcription and higher yields of Bv8 and/or EG-VEGF as compared to the native promoter.

Promoters suitable for use with prokaryotic hosts include the β-lactamase and lactose promoter systems (Chang et al., 1978, *Nature*, 275:615; Goeddel et al., *Nature*, 281:544 (1979)), alkaline phosphatase, a tryptophan (trp) promoter system (Goeddel, *Nucleic Acids Res.*, 8:4057 (1980); EP 36,776), and hybrid promoters such as the tac promoter. deBoer et al., 1983, *Proc. Natl. Acad. Sci. USA*, 80:21-25. However, other known bacterial promoters are suitable. Their nucleotide sequences have been published, thereby enabling a skilled worker operably to ligate them to DNA encoding Bv8 and/or EG-VEGF (Siebenlist et al., *Cell*, 20:269 (1980)) using linkers or adaptors to supply any required restriction sites. Promoters for use in bacterial systems also will contain a Shine-Delgarno (S.D.) sequence operably linked to the DNA encoding Bv8 and/or EG-VEGF.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly-A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., 1980, *J. Biol. Chem.*, 255:2073) or other glycolytic enzymes (Hesse et al., 1968, *J. Adv. Enzyme Reg.*, 7:149: Holland, 1978, Biochemistry, 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described, for example, in EP 73,657. Yeast enhancers also are advantageously used with yeast promoters.

Bv8 transcription and/or EG-VEGF transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 5), bovine papilloma virus, avian sarcoma virus, cytomegalovirus, a retrovirus, hepatitis-B virus, and most preferably Simian Virus 40 (SV40), from heterologous mammalian promoters, e.g., the actin promoter or an immunoglobulin promoter, from heat-shock promoters, and from the promoter normally associated with the Bv8 or EG-VEGF sequence, provided such promoters are compatible with the host cell systems.

The early and late promoters of the SV40 virus are conveniently obtained as an SV40 restriction fragment that also contains the SV40 viral origin of replication. Fiers et al., 1978, *Nature*, 273:113; Mulligan et al., 1980, *Science*, 209: 1422-1427; Pavlakis et al., 1981, *Proc. Natl. Acad. Sci. USA*, 78:7398-7402. The immediate early promoter of the human cytomegalovirus is conveniently obtained as a HindIII E restriction fragment. Greenaway et al., 1982, *Gene*, 18:355-360. A system for expressing DNA in mammalian hosts using the bovine papilloma virus as a vector is disclosed in U.S. Pat. No. 4,419,446. A modification of this system is described in U.S. Pat. No. 4,601,978. See also Gray et al., 1982, *Nature*, 295:503-508 on expressing cDNA encoding immune interferon in monkey cells; Reyes et al., 1982, *Nature*, 297:598-601 on expression of human β-interferon cDNA in mouse cells under the control of a thymidine kinase promoter from herpes simplex virus; Canaani et al., *Proc.* 1982, *Natl. Acad. Sci. USA*, 79:5166-5170 on expression of the human interferon β1 gene in cultured mouse and rabbit cells; and Gorman et al., 1982, *Proc. Natl. Acad. Sci. USA*, 79:6777-6781 on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Transcription of a DNA encoding Bv8 and/or EG-VEGF by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., 1981, *Proc. Natl. Acad. Sci USA*, 78:993) and 3' (Lusky et al., 1983, *Mol. Cell Bio.*, 3:1108) to the transcription unit, within an intron (Banerji et al., 1983, *Cell*, 33:729), as well as within the coding sequence itself. Osborne et al., 1984, *Mol. Cell. Bio.*, 4:1293. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, 1982, *Nature,* 297:17-18 on enhancing elements for activation of eukaryotic promoters. The enhancer may be spliced into the vector at a position 5' or 3' to the Bv8-encoding sequence or EG-VEGF encoding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding Bv8 and/or EG-VEGF.

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., 1981, *Nucleic Acids Res.,* 9:309 or by the method of Maxam et al., 1980, *Methods in Enzymology,* 65:499.

Particularly useful in the preparation of Bv8, EG-VEGF, and variants thereof are expression vectors that provide for the transient expression in mammalian cells of DNA encoding Bv8 and/or EG-VEGF. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra. pp. 16.17-16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of Bv8 and/or EG-VEGF that are biologically active.

Other methods, vectors, and host cells suitable for adaptation to the synthesis of Bv8, EG-VEGF, or a combination thereof in recombinant vertebrate cell culture are described in Gething et al., 1981, *Nature,* 293:620-625; Mantei et al., 1979, *Nature,* 281:40-46; EP 117,060; and EP 117,058. A particularly useful plasmid for mammalian cell culture expression of Bv8 and/or EG-VEGF is pRK5 (EP 307,247) orpSVKB. WO 91/08291 published 13 Jun. 1991.

Suitable host cells for cloning or expressing the DNA in the vectors herein are prokaryote, yeast, or higher eukaryote cells. Suitable prokaryotes for this purpose include eubacteria, such as Gram-negative or Gram-positive organisms, for example, Enterobacteriaceae such as *Escherichia,* e.g., *E. coli, Enterobacter, Erwinia, Klebsiella, Proteus, Salmonella,* e.g., *Salmonella typhimurium, Serratia,* e.g., *Serratia marcescans,* and *Shigella,* as well as Bacilli such as *B. subtilis* and *B. licheniformis* (e.g., *B. licheniformis* 41P disclosed in DD 266,710 published 12 Apr. 1989), *Pseudomonas* such as *P. aeruginosa,* and *Streptomyces.* One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Strain W3110 is a particularly preferred host or parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 27C7. The complete genotype of 27C7 is tonAΔ ptr3 phoAΔE15 Δ (argF-lac)169 ompTΔ degP41kan'. Strain 27C7 was deposited on 30 Oct. 1991 in the American Type Culture Collection as ATCC No. 55,244. Alternatively, the strain of *E. coli* having mutant periplasmic protease disclosed in U.S. Pat. No. 4,946,783 issued 7 Aug. 1990 may be employed.

In addition to prokaryotes, eukaryotic microbes such as filamentous fungi or yeast are suitable cloning or expression hosts for Bv8-encoding vectors and/or EG-VEGF encoding vectors. *Saccharomyces cerevisiae,* or common baker's yeast, is the most commonly used among lower eukaryotic host microorganisms. However, a number of other genera, species, and strains are commonly available and useful herein, such as *Schizosaccharomyces pombe* (Beach et al., 1981, *Nature,* 290:140; EP 139,383 published 2 May 1985); *Kluyveromyces* hosts (U.S. Pat. No. 4,943,529; Fleer et al., supra) such as, e.g., *K. lactis* (MW98-8C, CBS683, CBS4574; Louvencourt et al., 1983, *J. Bacteriol.,* 737), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra), *K. thermotolerans,* and *K. marxianus; yarrowia* (EP 402,226); *Pichia pastoris* (EP 183,070; Sreekrishna et al., 1988, *J. Basic Microbiol.,* 28:265-278); *Candida; Trichoderma reesia* (EP 244,234); *Neurospora crassa* (Case et al., 1979, *Proc. Natl. Acad. Sci. USA,* 76:5259-5263); *Schwanniomyces* such as *Sckwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., 1983, *Biochem. Biophys. Res. Commun.,* 112:284-289; Tilburne et al., 1983, *Gene,* 26:205-221; Yelton et al., 1984, *Proc. Natl. Acad. Sci. USA,* 81:1470-1474) and *A. niger.* Kelly et al., 1985, *EMBO J.,* 4:475-479.

Suitable host cells for the expression of glycosylated Bv8 and/or glycosylated EG-VEGF are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology,* 6:47-55 (1988); Miller et al., in *Genetic Engineering,* Setlow et al., eds., Vol. 8 (Plenum Publishing, 1986), pp. 277-279; and Maeda et al., 1985, *Nature,* 315:592-594. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens* that has been previously manipulated to contain the Bv8-encoding DNA, EG-VEGF encoding DNA, or a combination thereof. During incubation of the plant cell culture with *A. tumefaciens*, the DNA encoding the Bv8 and/or EG-VEGF is transferred to the plant cell host such that it is transfected, and will, under appropriate conditions, express the Bv8-encoding DNA and/or EG-VEGF encoding DNA. In addition, regulatory and signal sequences compatible with plant cells are available, such as the nopaline synthase promoter and polyadenylation signal sequences. Depicker et al., 1982, *J. Mol. Appl. Gen.*, 1:561. In addition, DNA segments isolated from the upstream region of the T-DNA 780 gene are capable of activating or increasing transcription levels of plant-expressible genes in recombinant DNA-containing plant tissue. EP 321,196 published 21 Jun. 1989.

However, interest has been greatest in vertebrate cells, and propagation of vertebrate cells in culture (tissue culture) has become a routine procedure. See, e.g., *Tissue Culture*, Academic Press, Kruse and Patterson, editors (1973). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol,* 36:59 (1977)); baby hamster kidney cells (BHK, ATCC CCL 10); Chinese hamster ovary cells/–DHFR (CHO, Urlaub et al., *Proc. Natl. Acad. Sci. USA,* 77:4216 (1980)); mouse sertoli cells (TM4, Mather, *Biol. Reprod.,* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.,* 383:44-68 (1982)); MRC 5 cells; FS4 cells; and a human hepatoma line (Hep G2).

Host cells are transfected and preferably transformed with the above-described expression or cloning vectors for Bv8 production and/or EG-VEGF production and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, or electroporation is generally used for prokaryotes or other cells that contain substantial cell-wall barriers. Infection with *Agrobacterium tumefaciens* is used for transformation of certain plant cells, as described by Shaw et al., 1983, *Gene,* 23:315 and WO 89/05859 published 29 Jun. 1989. In addition, plants may be transfected using ultrasound treatment as described in WO 91/00358 published 10 Jan. 1991.

For mammalian cells without such cell walls, the calcium phosphate precipitation method of Graham et al., 1978, *Virology,* 52:456-457 is preferred. General aspects of mammalian cell host-system transformations have been described in U.S. Pat. No. 4,399,216 issued 16 Aug. 1983. Transformations into yeast are typically carried out according to the method of Van Solingen et al., *J. Bact,* 130:946 and Hsiao et al., 1979, *Proc. Natl. Acad. Sci. USA,* 76:3829. However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., 1990, *Methods in Enzymology,* 185:527-537 and Mansour et al., 1988, *Nature,* 336:348-352.

Prokaryotic cells used to produce Bv8 polypeptide, EG-VEGF polypeptide, or a combination thereof, are cultured in suitable media as described generally in Sambrook et al., supra.

The mammalian host cells used to produce the Bv8, EG-VEGF, or a combination thereof, of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al. 1979, *Meth. Enz.,* 58:44, Barnes et al., 1980, *Anal. Biochem.,* 102:255, U.S. Pat. Nos. 4,767,704; 4,657,866; 4,927,762; 4,560,655; or 5,122,469; WO 90/03430: WO 87/00195; or U.S. Pat. Re. 30,985 may be used as culture media for the host cells. Any of these media may be supplemented as necessary with hormones and or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed. (IRL Press, 1991).

The host cells referred to in this disclosure encompass cells in culture as well as cells that are within a host animal.

Gene amplification and/or expression may be measured in a sample directly, for example, by conventional Southern blotting, Northern blotting to quantitate the transcription of mRNA (Thomas, 1980, *Proc. Natl. Acad. Sci. USA,* 77:5201-5205), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, can be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., 1980, *Am. J. Clin. Path.*, 75:734-738.

Antibodies useful for immunohistochemical staining and/or assay of sample fluids may be either monoclonal or polyclonal, and may be prepared as described herein.

Bv8 and/or EG-VEGF preferably is recovered from the culture medium as a secreted polypeptide, although it also may be recovered from host cell lysates. If the Bv8 or EG-VEGF is membrane-bound, it can be released from the membrane using a suitable detergent solution (e.g. Triton-X 100).

When Bv8, EG-VEGF, or a combination thereof is produced in a recombinant cell other than one of human origin, the Bv8 and/or EG-VEGF is completely free of proteins or polypeptides of human origin. However, it is necessary to purify Bv8 and/or EG-VEGF from recombinant cell proteins or polypeptides to obtain preparations that are substantially homogeneous as to Bv8 and/or EG-VEGF. As a first step, the culture medium or lysate can be centrifuged to remove particulate cell debris. Bv8 and/or EG-VEGF can then be purified from contaminant soluble proteins and polypeptides with the following procedures, which are exemplary of suitable purification procedures: by fractionation on an ion-exchange column; ethanol precipitation; reverse phase HPLC; chromatography on silica; chromatofocusing; immunoaffinity; epitope-tag binding resin; SDS-PAGE; ammonium sulfate precipitation; gel filtration using, for example, Sephadex G-75; and protein A Sepharose columns to remove contaminants such as IgG.

E. Modifications of Bv8 and EG-VEGF

Covalent modifications of Bv8, EG-VEGF, and variants thereof are included within the scope of this invention. One type of covalent modification includes reacting targeted amino acid residues of a Bv8 polypeptide and/or EG-VEGF polypeptide with an organic derivatizing agent that is capable of reacting with selected side chains or the N- or C-terminal residues of the Bv8 or EG-VEGF. Derivatization with bifunctional agents is useful, for instance, for crosslinking Bv8 or EG-VEGF to a water-insoluble support matrix or surface for use in the method for purifying anti-Bv8 antibodies or EG-VEGF antibodies respectively, and vice versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, 1983, *Proteins: Structure and Molecular Properties*, W.H. Freeman & Co. San Francisco, pp. 79-86), acetylation of the N-terminal amine, and amidation of any C-terminal carboxyl group.

Another type of covalent modification of the Bv8 polypeptide and/or EG-VEGF polypeptide included within the scope of this invention comprises altering the native glycosylation pattern of the polypeptide. "Altering the native glycosylation pattern" is intended for purposes herein to mean deleting one or more carbohydrate moieties found in native sequence Bv8 (either by removing the underlying glycosylation site or by deleting the glycosylation by chemical and/or enzymatic means), and/or adding one or more glycosylation sites that are not present in the native sequence Bv8 or EG-VEGF native sequence. In addition, the phrase includes qualitative changes in the glycosylation of the native proteins, involving a change in the nature and proportions of the various carbohydrate moieties present.

Addition of glycosylation sites to the Bv8 polypeptide or EG-VEGF polypeptide may be accomplished by altering the amino acid sequence. The alteration may be made, for example, by the addition of, or substitution by, one or more serine or threonine residues to the native sequence Bv8 or native sequence EG-VEGF (for O-linked glycosylation sites). The Bv8 amino acid sequence or EG-VEGF amino acid sequence may optionally be altered through changes at the DNA level, particularly by mutating the DNA encoding the Bv8 polypeptide or EG-VEGF polypeptide at pre-selected bases such that codons are generated that will translate into the desired amino acids.

Another means of increasing the number of carbohydrate moieties on the Bv8 polypeptide or EG-VEGF polypeptide is by chemical or enzymatic coupling of glycosides to the polypeptide. Such methods are described in the art, e.g., in WO 87/05330 published 11 Sep. 1987, and in Aplin and Wriston, 1981, *CRC Crit. Rev. Biochem.*, pp. 259-306.

Removal of carbohydrate moieties present on the Bv8 polypeptide or EG-VEGF polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., 1987, *Arch. Biochem. Biophys.*, 259:52 and by Edge et al., 1981, *Anal. Biochem.*, 118:131. Enzymatic cleavage of carbohydrate moieties on polypeptides can be achieved by the use of a variety of endo- and exo-glycosidases as described by Thotakura et al., 1987, *Meth. Enzymol.*, 138:350.

Another type of covalent modification of Bv8 or EG-VEGF comprises linking the Bv8 polypeptide or EG-VEGF polypeptide, respectively, to one of a variety of non-proteinaceous polymers. e.g., polyethylene glycol (PEG), polypropylene glycol, or polyoxyalkylenes, in the manner set forth, for example, in U.S. Pat. Nos. 4,640,835; 4,496.689; 4,301,144; 4,670,417; 4,791,192 or 4,179,337.

The Bv8 and EG-VEGF of the present invention may also be modified in a way to form a chimeric molecule comprising Bv8 or EG-VEGF fused to another, heterologous polypeptide or amino acid sequence.

In one embodiment, such a chimeric molecule comprises a fusion of the Bv8 or EG-VEGF with a tag polypeptide that provides an epitope to which an anti-tag antibody can selectively bind. The epitope tag is generally placed at the amino- or carboxyl-terminus of the Bv8 or EG-VEGF. The presence of such epitope-tagged forms of the Bv8 and/or EG-VEGF can be detected using an antibody against the tag polypeptide. Also, provision of the epitope tag enables the Bv8 and/or EG-VEGF to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flue HA tag polypeptide and its antibody 12CA5 (Field et al., 1988, *Mol. Cell. Biol.,* 8:2159-2165); the c-myc tag and the 8F9, 3C7, 6E10, G4, B7 and 9E10 antibodies thereto (Evan et al., 1985, *Molecular and Cellular Biology,* 5:3610-3616); and the Herpes Simplex virus glycoprotein D (gD) tag and its antibody (Paborsky et al., 1990, *Protein Engineering,* 3(6):547-553). Other tag polypeptides include the Flag-peptide (Hopp et al., 1988, *BioTechnology,* 6:1204-1210); the KT3 epitope peptide (Martin et al., 1992, *Science,* 255:192-194); an α-tubulin epitope peptide (Skinner et al., 1991, *J. Biol. Chem.,* 266: 15163-15166); and the T7 gene 10 protein peptide tag (Lutz-Freyermuth et al., 1990, *Proc. Natl. Acad. Sci. USA,* 87:6393-6397).

In an alternative embodiment, the chimeric molecule may comprise a fusion of Bv8 and/or EG-VEGF with an immunoglobulin or a particular region of an immunoglobulin. For a bivalent form of the chimeric molecule (also referred to as an "immunoadhesin"), such a fusion could be to the Fc region of an IgG molecule.

The simplest and most straightforward immunoadhesin design combines the binding region(s) of the "adhesin" protein with the hinge and Fc regions of an immunoglobulin heavy chain. Ordinarily, when preparing Bv8-immunoglobulin chimeras or EG-VEGF-immunoglobulin chimeras for use in the present invention, nucleic acid encoding Bv8 and/or EG-VEGF will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge and CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain.

The precise site at which the fusion is made is not critical; particular sites are well known and may be selected in order to optimize the biological activity of the Bv8 and/or EG-VEGF immunoglobulin chimeras.

In some embodiments, the Bv8-immunoglobulin chimeras and/or EG-VEGF immunoglobulin chimeras are assembled as monomers, or hetero- or homo-multimer, and particularly as dimers or tetramers, essentially as illustrated in WO 191/08298.

In a preferred embodiment, the Bv8 and/or EG-VEGF sequence is fused to the N-terminus of the C-terminal portion of an antibody (in particular the Fc domain), containing the effector functions of an immunoglobulin, e.g. immunoglobulin $G_1$ (IgG1). It is possible to fuse the entire heavy chain constant region to the Bv8 and/or EG-VEGF sequence. However, more preferably, a sequence beginning in the hinge region just upstream of the papain cleavage site (which defines IgG Fc chemically; residue 216, taking the first residue of heavy chain constant region to be 114, or analogous sites of other immunoglobulins) is used in the fusion. In a particularly preferred embodiment, the Bv8 amino acid sequence and/or EG-VEGF amino acid sequence is fused to the hinge region and CH2 and CH3, or to the CHI, hinge, CH2 and CH3 domains of an IgG1, IgG2, or IgG3 heavy chain. The precise site at which the fusion is made is not critical, and the optimal site can be determined by routine experimentation.

In some embodiments, the Bv8 and/or EG-VEGF immunoglobulin chimeras are assembled as multimer, and particularly as homo-dimers or -tetramers. Generally, these assembled immunoglobulins will have known unit structures. A basic four chain structural unit is the form in which IgG, IgD, and IgE exist. A four-unit is repeated in the higher molecular weight immunoglobulins; IgM generally exists as a pentamer of basic four-units held together by disulfide bonds. IgA globulin, and occasionally IgG globulin, may also exist in multimeric form in serum. In the case of a multimer, each four-unit may be the same or different.

Alternatively, the Bv8 sequence or EG-VEGF sequence can be inserted between immunoglobulin heavy chain and light chain sequences such that an immunoglobulin comprising a chimeric heavy chain is obtained. In this embodiment, the Bv8 sequence or EG-VEGF sequence is fused to the 3' end of an immunoglobulin heavy chain in each arm of an immunoglobulin, either between the hinge and the CH2 domain, or between the CH2 and CH3 domains. Similar constructs have been reported by Hoogenboom et al., *Mol. Immunol.,* 28:1027-1037 (1991).

Although the presence of an immunoglobulin light chain is not required in the immunoadhesins of the present invention, an immunoglobulin light chain might be present either covalently associated to a Bv8 or EG-VEGF immunoglobulin heavy chain fusion polypeptide, or directly fused to Bv8 or EG-VEGF. In the former case, DNA encoding an immunoglobulin light chain is typically coexpressed with the DNA encoding the Bv8 or EG-VEGF immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567 issued 28 Mar. 1989.

In a preferred embodiment, the immunoglobulin sequences used in the construction of the immunoadhesins of the present invention are from an IgG immunoglobulin heavy chain constant domain. For human immunoadhesins, the use of human IgG1 and IgG3 immunoglobulin sequences is preferred. A major advantage of using IgG1 is that IgG1 immunoadhesins can be purified efficiently on immobilized protein A. In contrast, purification of IgG3 requires protein G, a significantly less versatile medium. However, other structural and functional properties of immunoglobulins should be considered when choosing the Ig fusion partner for a particular immunoadhesin construction. For example, the IgG3 hinge is longer and more flexible, so it can accommodate larger adhesin domains that may not fold or function properly when fused to IgG1. Another consideration may be valency; IgG immunoadhesins are bivalent homodimers, whereas Ig subtypes like IgA and IgM may give rise to dimeric or pentameric structures, respectively, of the basic Ig homodimer unit. For Bv8 and/or EG-VEGF immunoadhesins designed for in vivo application, the pharmacokinetic properties and the effector functions specified by the Fc region are important as well. Although IgG1, IgG2 and IgG4 all have in vivo half-lives of 21 days, their relative potencies at activating the complement system are different. IgG4 does not activate complement, and IgG2 is significantly weaker at complement activation than IgG1. Moreover, unlike IgG1, IgG2 does not bind to Fc receptors on mononuclear cells or neutrophils. While IgG3 is optimal for complement activation, its in vivo half-life is approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, IgG1 has only four serologically-defined allotypic sites, two of which (Glm and 2) are located in the Fc region; and one of these sites Glm1, is non-immunogenic. In contrast, there are 12 serologically-defined allotypes in IgG3, all of which are in the Fc region; only three of these sites (G3m5, 11 and 21) have one allotype which is nonimmunogenic. Thus, the potential immunogenicity of a γ3 immunoadhesin is greater than that of a γ1 immunoadhesin.

With respect to the parental immunoglobulin, a useful joining point is just upstream of the cysteines of the hinge that form the disulfide bonds between the two heavy chains. In a frequently used design, the codon for the C-terminal residue of the Bv8 or EG-VEGF part of the molecule is placed directly upstream of the codons for the sequence DKTHTCP-PCP of the IgG1 hinge region.

The general methods suitable for the construction and expression of immunoadhesins are the same as those disclosed hereinabove with regard to Bv8 and EG-VEGF. Bv8 immunoadhesins and EG-VEGF immunoadhesins are most conveniently constructed by fusing the cDNA sequence encoding the Bv8 portion or EG-VEGF portion respectively in-frame to an Ig cDNA sequence. However, fusion to genomic Ig fragments can also be used (see, e.g., Gascoigne et al., 1987, *Proc. Natl. Acad. Sci. USA,* 84:2936-2940; Aruffo et al., 1990, *Cell,* 61:1303-1313; Stamenkovic et al., 1991, *Cell,* 66:1133-1144). The latter type of fusion requires the presence of Ig regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques. The cDNAs encoding the Bv8 or EG-VEGF and Ig parts of the immunoadhesin are inserted in tandem into a plasmid vector that directs efficient expression in the chosen host cells. For expression in mammalian cells, pRK5-based vectors (Schall et al., 1990, *Cell,* 61:361-370) and CDM8-based vectors (Seed, 1989, *Nature,* 329:840) can be used. The exact junction can be created by removing the extra sequences between the designed junction codons using oligonucleotide-directed deletional mutagenesis (Zoller et al., 1982, *Nucleic Acids Res.,* 10:6487; Capon et al., 1989, *Nature,* 337:525-531). Synthetic oligonucleotides can be used, in which each half is complementary to the sequence on either side of the desired junction; ideally, these are 36 to 48-mers. Alternatively, PCR techniques can be used to join the two parts of the molecule in-frame with an appropriate vector.

The choice of host cell line for the expression of Bv8 or EG-VEGF immunoadhesins depends mainly on the expression vector. Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient immunoadhesin expression. CDM8-based vectors can be used to transfect COS cells by the DEAE-dextran method (Aruffo et al., 1990, *Cell,* 61:1303-1313; Zettmeissl et al., 1990, *DNA Cell Biol. US,* 9:347-353). If larger amounts of protein are desired, the immunoadhesin can be expressed after stable transfection of a host cell line. For example, a pRK5-based vector can be introduced into Chinese hamster ovary (CHO) cells in the presence of an additional plasmid encoding dihydrofolate reductase (DHFR) and conferring resistance to G418. Clones resistant to G418 can be selected in culture; these clones are grown in the presence of increasing levels of DHFR inhibitor methotrexate; clones are selected, in which the number of gene copies encoding the DHFR and immunoadhesin sequences is co-amplified. If the immunoadhesin contains a hydrophobic leader sequence at its N-terminus, it is likely to be processed and secreted by the transfected cells. The expression of immunoadhesins with more complex structures may require uniquely suited host cells; for example, components such as light chain or J chain may be provided by certain myeloma or hybridoma cell hosts (Gascoigne et al., 1987, supra, Martin et al., 1993, *J. Virol,* 67:3561-3568).

Immunoadhesins can be conveniently purified by affinity chromatography. The suitability of protein A as an affinity ligand depends on the species and isotype of the immunoglobulin Fc domain that is used in the chimera. Protein A can be used to purify immunoadhesins that are based on human γ1, γ2, or γ4 heavy chains (Lindmarke et al., *J. Immunol. Meth.,* 62:1-13 (1983)). Protein G is recommended for all mouse isotypes and for human γ3 (Guss et al., 1986, *EMBO J.,* 5:1567-1575). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. One distinguishing feature of immunoadhesins is that, for human γ1 molecules, the binding capacity for protein A is somewhat diminished relative to an antibody of the same Fc type. Bound immunoadhesin can be efficiently eluted either at acidic pH (at or above 3.0), or in a neutral pH buffer containing a mildly chaotropic salt. This affinity chromatography step can result in an immunoadhesin preparation that is >95% pure.

Other methods known in the art can be used in place of, or in addition to, affinity chromatography on protein A or G to purify immunoadhesins. Immunoadhesins behave similarly to antibodies in thiophilic gel chromatography (Hutchens et al., 1986, *Anal. Biochem.,* 159:217-226) and immobilized metal chelate chromatography (Al-Mashikhi et al., 1988, *J. Dairy Sci.,* 71:1756-1763). In contrast to antibodies, however, their behavior on ion exchange columns is dictated not only by their isoelectric points, but also by a charge dipole that may exist in the molecules due to their chimeric nature.

If desired, the immunoadhesins can be made bispecific. Thus, the immunoadhesins of the present invention may combine a Bv8 or EG-VEGF domain and a domain, such as a domain from another growth factor including, but not limited to VEGF, Bv8, and EG-VEGF. For bispecific molecules, trimeric molecules, composed of a chimeric antibody heavy chain in one arm and a chimeric antibody heavy chain-light chain pair in the other arm of their antibody-like structure are advantageous, due to ease of purification. In contrast to antibody-producing quadromas traditionally used for the production of bispecific immunoadhesins, which produce a mixture of ten tetramers, cells transfected with nucleic acid encoding the three chains of a trimeric immunoadhesin structure produce a mixture of only three molecules, and purification of the desired product from this mixture is correspondingly easier.

F. Modulators of Bv8 Activity and EG-VEGF Activity

The present invention also encompasses methods of screening compounds to identify those that mimic or enhance one or more biological activity of Bv8 and/or EG-VEGF (agonists) or prevent the effect of Bv8 and/or EG-VEGF (antagonists). Bv8 and EG-VEGF agonists and antagonists are also referred to as Bv8 and EG-VEGF modulators, respectively. Screening assays for antagonist drug candidates are designed to identify compounds that bind or complex with Bv8 polypeptides and/or EG-VEGF polypeptide, or otherwise interfere with the interaction of Bv8 and/or EG-VEGF with other cellular proteins.

1. Small Molecule Screening

Small molecules may have the ability to act as Bv8 agonists or antagonists and/or E-VEGF agonists or antagonists and thus to be therapeutically useful. Such small molecules may include naturally occurring small molecules, synthetic, organic, or inorganic compounds and peptides. However, small molecules in the present invention are not limited to these forms. Extensive libraries of small molecules are commercially available and a wide variety of assays are well known in the art to screen these molecules for the desired activity.

Candidate Bv8 agonist or antagonist and/or EG-VEGF agonist or antagonist small molecules are preferably identified first in an assay that allows for the rapid identification of potential modulators of Bv8 and/or EG-VEGF activity. An example of such an assay is a protein-protein binding assay wherein the ability of the candidate molecule to bind to a Bv8 or EG-VEGF receptor is measured. In another example, the ability of candidate molecules to interfere with Bv8 binding to a Bv8 receptor or EG-VEGF binding to an EG-VEGF receptor is measured. In an embodiment, the respective Bv8 receptor or EG-VEGF receptor is Bv8/EG-VEGF receptor-1 and/or Bv8/EG-VEGF receptor-2.

In a preferred embodiment, small molecule Bv8 agonists and EG-VEGF are identified by their ability to mimic one or more of the biological activities of Bv8 or EG-VEGF, respectively. For example, candidate compounds are screened for their ability to induce proliferation of endothelial cells, to promote endothelial cell survival, or to induce angiogenesis, as described below. Candidate compounds that induce one or more of the described biological activities of Bv8 or EG-VEGF are identified as agonists.

In another embodiment, small molecule Bv8 antagonists and/or EG-VEGF antagonists are identified by their ability to inhibit one or more of the biological activities of Bv8 and/or EG-VEGF, respectively. For example, candidate compounds are screened for their ability to inhibit proliferation of endothelial cells, endothelial cell survival, or angiogenesis, as described below. Candidate compounds that inhibit one or more of the described biological activities of Bv8 or EG-VEGF are identified as antagonists.

The ability of a candidate compound to induce or inhibit angiogenesis is determined, for example, in mice testes as described in WO 02/00711 and WO 03/020892.

Endothelial cell proliferation is determined, for example, as described in WO 02/00711 and WO 03/020892. Briefly, endothelial cells are grown in low glucose DMEM supplemented with 10% bovine serum albumin containing a candidate agonist compound or Bv8 and/or EG-VEGF that has been contacted with a candidate antagonist compound. The endothelial cells are plated at a density of 4000 to 6000 cells/ml in 6 or 12 well dishes. At day 5 to 7 of the assay, the endothelial cells are trypsinized and the number of cells is quantitated using a Coulter counter.

Endothelial cell survival is determined, for example, as described in WO 02/00711 and WO 03/020892. Briefly, approximately $2\times10^5$ bovine brain capillary cells are plated in low glucose DMEM supplemented with 10% bovine serum albumin and incubated for 24 hours. The media is then aspirated and replaced with media containing a candidate agonist compound or Bv8 and/or EG-VEGF that has been contacted with a candidate antagonist compound. The cells are incubated for 48 hours, trypsinized, and fixed in 70% ethanol. The fixed cells are stained with propidium iodine and RNase and the sub-G1 profile of the cells is determined by FACs analysis.

Compounds identified as Bv8 and/or EG-VEGF agonists or antagonists may be used in the methods of the present invention. For example, Bv8 and/or EG-VEGF antagonists may be used to treat cancer.

2. Preparation and Identification of Antibodies

Agonist human and non-human polyclonal and monoclonal antibodies (including humanized forms of non-human monoclonal antibodies), which mimic the biological properties of Bv8 and/or EG-VEGF, and antagonist human and non-human polyclonal and monoclonal antibodies (including humanized forms of non-human monoclonal antibodies), which inhibit the biological properties of Bv8 and/or EG-VEGF, are also contemplated in the present invention. These include amino acid sequence variants, glycosylation variants and fragments of antibodies. General techniques for the production of such antibodies and the selection of agonist antibodies are known in the art and are briefly described below.

(i) Polyclonal Antibodies

Methods of preparing polyclonal antibodies are known in the art. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. It may be useful to conjugate the immunizing agent to a protein known to be immunogenic in the mammal being immunized, such as serum albumin, or soybean trypsin inhibitor. Examples of adjuvants that may be employed include Freund's complete adjuvant and MPL-TDM.

(ii) Monoclonal Antibodies

Monoclonal antibodies may be made using the hybridoma method first described by Kohler et al., 1975, *Nature,* 256: 495, or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103, (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), conditions under which the growth of HGPRT-deficient cells is prevented.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, 1984, *J. Immunol.*, 133:3001; Brodeur et al., *Monoclonal Antibody Production Techniques and Applications*, pp. 51-63, Marcel Dekker, Inc., New York, (1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., 1980, *Anal. Biochem.*, 107:220.

After hybridoma cells are identified that produce antibodies of the desired specificity, affinity, and/or activity, the cells may be subcloned by limiting dilution procedures and grown by standard methods (Goding, *Monoclonal Antibodies Principles and Practice*, pp. 59-10$^3$ (Academic Press, 1986)). Suitable culture media for this purpose include, for example, DMEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., 1984, *Proc. Nat. Acad. Sci. U.S.A.*, 81:6851, or by covalently joining to the immunoglobulin coding sequence all or part of the coding sequence for a non-immunoglobulin polypeptide. In that manner, "chimeric" or "hybrid" antibodies are prepared that have the binding specificity of a Bv8 or EG-VEGF agonist monoclonal antibody or Bv8 or EG-VEGF antagonist monoclonal antibody described herein.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

Recombinant production of antibodies will be described in more detail below.

(iii) Humanized Antibodies

Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers (Jones et al., 1986, *Nature*, 321:522-525; Riechmann et al., 1988, *Nature*, 332:323-327; Verhoeyen et al., 1988, *Science*, 239:1534-1536), by substituting rodent CDRs or CDR sequences for the corresponding sequences of a human antibody.

Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. Pat. Nos. 5,821,337 and 6,054,297.

(Iv) Human Antibodies

Human monoclonal antibodies can be made by the hybridoma method. Human myeloma and mouse-human heteromyeloma cell lines for the production of human monoclonal antibodies have been described, for example, by Kozbor, 1984, *J. Immunol.* 133, 3001, and Brodeur, et al., *Monoclonal Antibody Production Techniques and Applications*, pages 51-63 (Marcel Dekker, Inc., New York, 1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germline mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., 1993, *Proc Natl. Acad. Sci. USA* 90, 2551-255; Jakobovits et al., 1993, *Nature* 362, 255-258.

Mendez et al. (1997, *Nature Genetics* 15:146-156) have further improved the technology and have generated a line of transgenic mice designated as "Xenomouse II" that, when challenged with an antigen, generates high affinity fully human antibodies. This was achieved by germ-line integration of megabase human heavy chain and light chain loci into mice with deletion into endogenous $J_H$ segment as described above. The Xenomouse II harbors 1,020 kb of human heavy chain locus containing approximately 66 $V_H$ genes, complete $D_H$ and $J_H$ regions and three different constant regions (μ, δ and χ), and also harbors 800 kb of human κ locus containing 32 Vκ genes, Jκ segments and Cκ genes. The antibodies produced in these mice closely resemble that seen in humans in all respects, including gene rearrangement, assembly, and repertoire. The human antibodies are preferentially expressed over endogenous antibodies due to deletion in endogenous $J_H$ segment that prevents gene rearrangement in the murine locus.

Alternatively, phage display technology (McCafferty et al., 1990, Nature 348:552-553) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson, Kevin S, and Chiswell, David J., 1993, Current Opinion in Structural Biology 3:564-571. Several sources of V-gene segments can be used for phage display. Clackson et al., 1991, Nature 352:624-628 isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., 1991, J. Mol. Biol. 222:581-597, or Griffith et al., 1993, EMBO J. 12:725-734. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., 1992, BioTechnol., 10:779-783). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires (also known as "the mother-of-all libraries") has been described by Waterhouse et al., 1993, Nucl Acids Res. 21:2265-2266, and the isolation of a high affinity human antibody directly from such large phage library is reported by Griffith et al., 1993, EMBO J. 12:725-734. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable domains capable of restoring a functional antigen-binding site, i.e. the epitope governs (imprints) the choice of partner. When the process is repeated in order to replace the remaining rodent V domain, a human antibody is obtained (see PCT patent application WO 93/06213, published 1 Apr. 1993). Unlike traditional humanization of rodent antibodies by CDR grafting, this technique provides completely human antibodies, which have no framework or CDR residues of rodent origin.

(v) Bispecific Antibodies

Bispecific antibodies are monoclonal, preferably human or humanized, antibodies that have binding specificities for at least two different antigens. Methods for making bispecific antibodies are known in the art. Traditionally, the recombinant production of bispecific antibodies is based on the coexpression of two immunoglobulin heavy chain-light chain pairs, where the two heavy chains have different specificities (Millstein and Cuello, Nature 305, 537-539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published 13 May 1993), and in Traunecker et al., 1991, EMBO 10, 3655-3659.

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in PCT Publication No. WO 94/04690, published on Mar. 3, 1994.

For further details of generating bispecific antibodies see, for example, Suresh et al., 1986, Methods in Enzymology 121, 210.

(vi) Heteroconjugate Antibodies

Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373: EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

(vii) Antibody Fragments

In certain embodiments, the agonist and/or antagonist antibody (including murine, human and humanized antibodies and antibody variants) is an antibody fragment. Various techniques have been developed for the production of antibody fragments. Traditionally, these fragments were derived via proteolytic digestion of intact antibodies (see, e.g., Morimoto et al., 1992, *J. Biochem. Biophys. Methods* 24:107-117 and Brennan et al., 1985, *Science* 229:81). However, these fragments can now be produced directly by recombinant host cells. For example, Fab'-SH fragments can be directly recovered from *E. coli* and chemically coupled to form $F(ab')_2$ fragments (Carter et al., 1992, *Bio/Technology* 10:163-167). In another embodiment, the $F(ab')_2$ is formed using the leucine zipper GCN4 to promote assembly of the $F(ab')_2$ molecule. According to another approach, Fv, Fab or $F(ab')_2$ fragments can be isolated directly from recombinant host cell culture. Other techniques for the production of antibody fragments will be apparent to the skilled practitioner.

(viii) Identification of Agonist Antibodies

Bv8 agonist antibodies and EG-VEGF agonist antibodies are identified based on their ability to induce a biological activity of Bv8 or EG-VEGF, including but not limited to proliferation of endothelial cells, survival of endothelial cells, and angiogenesis. Assays for determining proliferation of endothelial cells, survival of endothelial cells, and angiogenesis are known in the art. Induction of proliferation of endothelial cells can be assayed as described above under small molecules. Bv8 agonist antibodies and EG-VEGF agonist antibodies can be identified by their ability to induce angiogenesis, for example in mice testes, as described in WO 02/00711 and WO 03/020892.

(ix) Identification of Antagonist Antibodies

Bv8 antagonist antibodies and EG-VEGF antagonist antibodies are identified based on their ability to inhibit a biological activity of Bv8 or EG-VEGF, including but not limited to proliferation of endothelial cells, survival of endothelial cells, and angiogenesis, for example, using one of the assays described above.

G. Screening for Proteins that Interact with Bv8 and/or EG-VEGF

Any method suitable for detecting protein-protein interactions may be employed for identifying proteins or other molecules, including but not limited to transmembrane or intracellular proteins, that interact with Bv8 and/or EG-VEGF. Among the traditional methods that may be employed are co-immunoprecipitation, crosslinking and co-purification through gradients or chromatographic columns to identify proteins that interact with Bv8 or EG-VEGF. For such assays, the Bv8 component or EG-VEGF component can be a full-length protein, a soluble derivative thereof, a peptide corresponding to a domain of interest, or a fusion protein containing some region of Bv8 or EG-VEGF.

Methods may be employed which result in the simultaneous identification of genes that encode proteins capable of interacting with Bv8 or EG-VEGF. These methods include, for example, probing expression libraries, in a manner similar to the well-known technique of antibody probing of λgt11 libraries, using labeled Bv8, labeled EG-VEGF, or a labeled variant thereof.

A method that detects protein interactions in vivo, the two-hybrid system, is described in detail for illustration only and not by way of limitation. One version of this system has been described (Chien et al., 1991, *Proc. Natl. Acad. Sci. USA*, 88:9578-9582) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to a nucleotide sequence encoding Bv8 or EG-VEGF, or a polypeptide, peptide, or fusion protein thereof, and the other plasmid consists of nucleotides encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, Bv8 or EG-VEGF can be used as the bait gene product. Total genomic or cDNA sequences are fused to the DNA encoding an activation domain. This library and a plasmid encoding a hybrid of a bait Bv8 gene product or bait EG-VEGF gene product fused to the DNA-binding domain are cotransformed into a yeast reporter strain, and the resulting transformants are screened for those that express the reporter gene. For example, and not by way of limitation, a bait Bv8 gene sequence or bait EG-VEGF gene sequence, for example, the genes open reading frame of the gene, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with the bait Bv8 gene product or bait EG-VEGF gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait Bv8 gene-GAL4 fusion plasmid or bait EG-VEGF gene-GAL4 fusion plasmid into a yeast strain that contains a lacZ gene driven by a promoter which contains a GAL4 activation sequence. A cDNA encoded protein, fused to GAL4 transcriptional activation domain, that interacts with the bait Bv8 gene product or bait EG-VEGF gene product will reconstitute an active GAL4 protein and thereby drive expression. Colonies that drive expression can be detected by methods routine in the art. The cDNA can then be purified from these strains, and used to produce and isolate the bait Bv8 gene-interacting protein or bait EG-VEGF gene-interacting protein using techniques routinely practiced in the art.

1. Compounds that Modulate Bv8 and/or EG-VEGF Expression or Activity

The following assays are designed to identify compounds that interact with (e.g., bind to) Bv8 or EG-VEGF compounds that interfere with the interaction of Bv8 or EG-VEGF with their binding partners, cognate receptor, and to compounds that modulate the activity of Bv8 gene expression and/or EG-VEGF gene expression (that is, modulate the level of Bv8 gene expression and/or EG-VEGF gene expression) or modulate the levels of Bv8 and/or EG-VEGF in the body. Assays can also be used to identify compounds that bind Bv8 and/or EG-VEGF gene regulatory sequences (for example, promoter sequences) and, consequently, modulate Bv8 and/or EG-VEGF gene expression. See, for example, Platt, K. A., 1994, *J. Biol. Chem.* 269:28558-28562, which is incorporated herein by reference in its entirety.

Compounds that may be screened in accordance with the invention include, but are not limited to peptides, soluble receptors or fragments thereof, antibodies and fragments thereof and other organic compounds (e.g., peptidomimetics) that bind to Bv8 or EG-VEGF, or to a Bv8/EG-VEGF receptor and either mimic the activity triggered by a natural ligand (agonists) or inhibit the activity triggered by the natural ligand (antagonists).

Such compounds may include, but are not limited to, peptides such as, for example, soluble peptides, including but not limited to members of random peptide libraries; (see, for example, Lam, K. S. et al., 1991, *Nature* 354:82-84; Houghten, R. et al., 1991, *Nature* 354:84-86), and combinatorial chemistry-derived molecular library made of D- and/or L-configuration amino acids, phosphopeptides (including, but not limited to members of random or partially degenerate, directed phosphopeptide libraries; see, for example, Songyang, Z. et al., 1993, *Cell* 72:767-778), antibodies (including, but not limited to, polyclonal, monoclonal, humanized, anti-idiotypic, chimeric, or single chain antibodies, and FAb, F(ab')$_2$, and FAb expression library fragments, and epitope-binding fragments thereof), and small organic or inorganic molecules.

Other compounds that can be screened in accordance with the invention include, but are not limited to small organic molecules that are able to gain entry into an appropriate cell (for example, an endothelial cell) and affect the expression of a Bv8 gene or an EG-VEGF gene, or some other gene involved in a Bv8 and/or EG-VEGF mediated pathway (e.g., by interacting with the regulatory region or transcription factors involved in gene expression); or such compounds that affect or substitute for the activity of Bv8 or EG-VEGF or the activity of some other intracellular factor involved in a Bv8 and/or EG-VEGF signal transduction, catabolic, or metabolic pathways.

Computer modeling and searching technologies permit identification of compounds, or the improvement of already identified compounds, that can modulate Bv8 or EG-VEGF expression or activity. Having identified such a compound or composition, the active sites or regions are identified. Such active sites might typically be ligand binding sites. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, that can determine a complete molecular structure. On the other hand, solid or liquid phase NMR can be used to determine certain intramolecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site (or binding site), either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential modulators of Bv8 activity and/or EG-VEGF activity.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites (or binding sites) of Bv8 or EG-VEGF, and related transduction and transcription factors will be apparent to those of skill in the art.

Examples of molecular modeling systems are the CHARMm and QUANTA programs (Polygen Corporation Waltham, Mass.), CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988, *Acta Pharmaceutical Fennica* 97:159-166; Ripka, Jun. 16, 1988, *New Scientist* 54-57; McKinaly and Rossmann, 1989, *Annu. Rev. Pharmacol. Toxiciol.* 29:111-122; Perry and Davies, *OSAR: Quantitative Structure-Activity Relationships in Drug Design* pp. 189-193 (Alan R. Liss, Inc. 1989); Lewis and Dean, 1989 *Proc. R. Soc. Lond.* 236:125-140 and 141-162; and, with respect to a model receptor for nucleic acid components, Askew, et al., 1989, *J. Am. Chem. Soc.* 111: 1082-1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein may be useful, for example, in elucidating the biological function of a Bv8 gene product and/or a EG-VEGF gene product. Such compounds can be administered to a patient at therapeutically effective doses to treat any of a variety of physiological disorders. A therapeutically effective dose refers to that amount of the compound sufficient to result in any amelioration, impediment, prevention, or alteration of any biological symptom.

2. Compounds that Bind to Bv8 and/or EG-VEGF

Systems may be designed to identify compounds capable of interacting with (for example, binding to) or mimicking Bv8 and/or EG-VEGF, or capable of interfering with the binding of Bv8 and/or EG-VEGF to a cognate receptor, binding partner, or substrate. The compounds identified can be useful, for example, in modulating the activity of wild type and/or mutant Bv8 gene products, EG-VEGF gene products, or combination thereof; can be useful in elaborating the biological function of Bv8 and/or EG-VEGF; can be utilized in screens for identifying compounds that disrupt normal Bv8 interactions and/or EG-VEGF interactions; or may themselves disrupt or activate such interactions.

The principle of the assays used to identify compounds that bind to Bv8 and/or EG-VEGF, or Bv8 and/or EG-VEGF cognate receptors or substrates, involves preparing a reaction mixture of Bv8 and/or EG-VEGF and the test compound under conditions and for a time sufficient to allow the two components to interact and bind, thus forming a complex which can be removed and/or detected in the reaction mixture. The Bv8 and/or EG-VEGF species used can vary depending upon the goal of the screening assay. For example, where agonists of the natural receptor are desired, the fulllength Bv8 or EG-VEGF, or a soluble truncated Bv8 or EG-VEGF, a peptide, or fusion protein containing one or more Bv8 or EG-VEGF domains fused to a protein or polypeptide that affords advantages in the assay system (e.g., labeling, isolation of the resulting complex, etc.) can be utilized. Where compounds that directly interact with Bv8 and/or EG-VEGF are sought, peptides corresponding to Bv8 or EG-VEGF and fusion proteins containing Bv8 or EG-VEGF can be used.

The screening assays can be conducted in a variety of ways. For example, one method to conduct such an assay would involve anchoring the Bv8 or EG-VEGF polypeptide, peptide, or fusion protein thereof, or the test substance onto a solid phase and detecting Bv8/test compound complexes or EG-VEGF/test compound complexes anchored on the solid phase at the end of the reaction. In one embodiment of such a method, the Bv8 reactant or EG-VEGF reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for a Bv8 or EG-VEGF protein, polypeptide, peptide or fusion protein or the test compound to anchor any complexes formed in solution, and a labeled antibody specific for the other component of the possible complex to detect anchored complexes.

3. Compounds that Interfere with Bv8 and/or EG-VEGF Interactions

Macromolecules that interact with Bv8 and/or EG-VEGF are referred to, for purposes of this discussion, as "binding partners". These binding partners are likely to be involved in Bv8 and/or EG-VEGF mediated biological pathways. Therefore, it is desirable to identify compounds that interfere with or disrupt the interaction of such binding partners which may be useful in regulating or augmenting Bv8 activity and/or EG-VEGF activity in the body and/or controlling disorders associated with this activity (or a deficiency thereof).

The basic principle of the assay systems used to identify compounds that interfere with the interaction between Bv8 or EG-VEGF and a binding partner or partners involves preparing a reaction mixture containing Bv8 and/or EG-VEGF, or some variant thereof, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of Bv8 or EG-VEGF and its binding partner. Control reaction mixtures are incubated without the test compound or with a placebo. The formation of any complexes between the Bv8 or EG-VEGF and the binding partner is then detected. The formation of a complex in the control reaction, but not in the reaction mixture containing the test compound, indicates that the compound interferes with the interaction of the Bv8 or EG-VEGF and the interactive binding partner. Additionally, complex formation within reaction mixtures containing the test compound and normal Bv8 protein or normal EG-VEGF protein may also be compared to complex formation within reaction mixtures containing the test compound and a mutant Bv8 or mutant EG-VEGF, respectively. This comparison may be important in those cases wherein it is desirable to identify compounds that specifically disrupt interactions of mutant, or mutated, Bv8 or EG-VEGF but not the normal proteins.

The assay for compounds that interfere with the interaction between Bv8 and/or EG-VEGF and their binding partners can be conducted in a heterogeneous or homogeneous format. Heterogeneous assays involve anchoring either Bv8 or EG-VEGF, or a binding partner thereof, onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; such as, by adding the test substance to the reaction mixture prior to, or simultaneously with, Bv8 or EG-VEGF and the interactive binding partner. Alternatively, test compounds that disrupt preformed complexes, e.g. compounds with higher binding constants that displace one of the components from the complex, can be tested by adding the test compound to the reaction mixture after complexes have been formed. Various formats are described briefly below.

In a heterogeneous assay system, either the polypeptide (Bv8 or EG-VEGF) or an interactive binding partner of the polypeptide, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the polypeptide or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g. by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the polypeptide (Bv8 or EG-VEGF) and an interactive binding partner is prepared where either the polypeptide or binding partner is labeled, but the signal generated by the label is quenched due to formation of the complex (see, for example, U.S. Pat. No. 4,109,496 by Rubenstein that utilizes this approach for immunoassays). The addition of a test substance that competes with and displaces one of the species from the preformed complex will result in the generation of a signal above background. In this way, test substances that disrupt the interaction can be identified.

In a particular embodiment, a Bv8 (or EG-VEGF) fusion can be prepared for immobilization. For example, the polypeptide (Bv8 or EG-VEGF) or a peptide fragment thereof, can be fused to a glutathione-5-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art and described above. This antibody can be labeled with the radioactive isotope $^{125}$I, for example, by methods routinely practiced in the art. In a heterogeneous assay, the fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the polypeptide (Bv8 or EG-VEGF) and the interactive binding partner can be detected by measuring the amount of radioactivity that remains associated with the glutathione-agarose beads. A successful inhibition of the interaction by the test compound will result in a decrease in measured radioactivity.

Alternatively, the GST fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the interaction between Bv8 and the binding partner or EG-VEGF and the binding partner can be detected by adding the labeled antibody and measuring the radioactivity associated with the beads.

In another embodiment of the invention, these same techniques can be employed using peptide fragments that correspond to the binding domains of the polypeptide (Bv8 or EG-VEGF) and/or the interactive binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensatory mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a relatively short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not by way of limitation, Bv8 and/or EG-VEGF can be anchored to a solid material as described, above, by making a GST fusion protein and allowing it to bind to glutathione agarose beads. The interactive binding partner can be labeled with a radioactive isotope, such as $^{35}$S, and cleaved with a proteolytic enzyme such as trypsin. Cleavage products can then be added to the anchored fusion protein and allowed to bind. After washing away unbound peptides, labeled bound material, representing the intracellular binding partner binding domain, can be eluted, purified, and analyzed for amino acid sequence by well-known methods. Peptides so identified can be produced synthetically or fused to appropriate facilitative proteins using recombinant DNA technology.

H. Pharmaceutical Compositions

The Bv8 polypeptides, EG-VEGF polypeptides, and modulators thereof described herein, including agonists and antagonists of Bv8 or EG-VEGF, may be employed as therapeutic agents. These polypeptides and modulators of the present invention can be formulated according to known methods to prepare pharmaceutically useful compositions, whereby the Bv8 and/or EG-VEGF product is combined in a mixture with a pharmaceutically acceptable carrier vehicle. Therapeutic formulations of Bv8, EG-VEGF, or combinations thereof are prepared by mixing Bv8 and/or EG-VEGF having the desired degree of purity, preferably essentially pure, with optional physiologically acceptable carriers, excipients or stabilizers (Remington's Pharmaceutical Sciences, supra), in the form of lyophilized cake or aqueous solutions. Acceptable carriers, excipients or stabilizers are nontoxic to the cell or mammal being exposed at the dosages and concentrations employed. Examples include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

Bv8 and/or EG-VEGF to be used for in vivo administration must be sterile. This is readily accomplished by any method known in the art, such as filtration through sterile filtration membranes, prior to or following lyophilization and reconstitution. Bv8 may be stored in lyophilized form. Therapeutic compositions of Bv8, EG-VEGF, and combinations thereof, generally are placed into a container having a sterile access port, for example, an intravenous solution bag or vial having a stopper pierceable by a hypodermic injection needle.

Bv8 optionally is combined with or administered in concert with other growth factors. For example it may be combined with EG-VEGF or VEGF. EG-VEGF optionally is combined with or administered in concert with other growth factors. For example it may be combined with Bv8 or VEGF.

Bv8, EG-VEGF, or modulators thereof, may be used with other conventional therapies for treating cancer, other hematological disorders, neutropenias, immunodeficiency disorders, autoimmune disorders, and the like.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

Where sustained-release administration of a Bv8 and/or EG-VEGF polypeptide or modulator is desired in a formulation with release characteristics suitable for the treatment of any disease or disorder requiring administration of the Bv8 and/or EG-VEGF polypeptide or modulator, microencapsulation of the Bv8 and/or EG-VEGF polypeptide or modulator, or a combination thereof, is contemplated. For example, Bv8, EG-VEGF, or a combination thereof in purified form may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, 1980, (A. Osol, Ed).

Bv8, EG-VEGF, or a combination thereof may be incorporated into sustained release preparations for therapeutic use. Suitable examples of sustained release preparations include semipermeable polymer matrices in the form of shaped articles, e.g. films, or microcapsules. Examples of sustained release matrices include polyesters, hydrogels (e.g. poly(2-hydroxyethyl-methacrylate) as described by Langer et al., 1981, *J. Biomed. Mater. Res.*, 15:167-277 and Langer, 1982, *Chem. Tech.*, 12:98-105 or poly(vinylalcohol)), polylactides (U.S. Pat. No. 3,773,919, EP 58,481), copolymers of L-glutamic acid and gamma ethyl-L-glutamate (Sidman, et al., 1983, *Biopolymers* 22:547), non-degradable ethylene vinyl acetate (Langer, et al., supra) or degradable lactic acid-glycolic acid copolymers such as the Lupron Depo™ (injectable microspheres composed of lactic acid-glycoloic acid copolymer and leuprolide acetate), and poly-D-(–)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained release Bv8 and/or EG-VEGF compositions also include liposomally entrapped Bv8 and/or EG-VEGF. Liposomes containing Bv8 and/or EG-VEGF are prepared by methods known in the art. (Epstein, et al., 1985, *Proc. Natl. Acad. Sci.* 82:3688; Hwang, et al., 1980, *Proc. Natl. Acad. Sci. USA* 77:4030; DE 3218121A; EP 52322A; EP 36676A; EP 88046A; EP 143949A; EP 142641A; Japanese Pat. App. No. 83-118008; U.S. Pat. Nos. 4,485,045 and 4,544,545; and EP 102,324A). Ordinarily the liposomes are of the small (about 200-800 Angstroms) unilamelar type in which the lipid content is greater than about 30 mol. % cholesterol, the selected proportion being adjusted for the optimal Bv8 therapy.

When applied topically, Bv8, EG-VEGF, or a combination thereof, is suitably combined with other ingredients, such as carriers and/or adjuvants. There are no limitations on the nature of such other ingredients, except that they must be physiologically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, Bv8, EG-VEGF, or a combination thereof formulated in a liquid composition may be mixed with an effective amount of a water-soluble polysaccharide or synthetic polymer such as PEG to form a gel of the proper viscosity to be applied topically. The polysaccharide that may be used includes, for example, cellulose derivatives such as etherified cellulose derivatives, including alkyl celluloses, hydroxyalkyl celluloses and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the Bv8 and/or EG-VEGF held within the gel.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight PEGs to obtain the proper viscosity. For example, a mixture of a PEG of molecular weight 400-600 with one of molecular weight 1500 would be effective for this purpose when mixed in the proper ratio to obtain a paste.

The term "water soluble" as applied to the polysaccharides and PEGs is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water-soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2-5%, more preferably about 3%, of the gel and Bv8 and/or EG-VEGF is present in an amount of about 300-1000 mg per ml of gel.

Semipermeable, implantable membrane devices are useful as means for delivering drugs in certain circumstances. For example, cells that secrete Bv8 and/or EG-VEGF, Bv8 and/or EG-VEGF variants, Bv8 and/or EG-VEGF chimeras, or agonists or antagonists of Bv8 and/or EG-VEGF can be encapsulated, and such devices can be implanted into a patient. Accordingly, also included is a method for preventing or treating cancer, other hematological disorders, neutropenias, immunological disorders, autoimmune disorders, and the like, that comprises implanting cells that secrete Bv8 and/or EG-VEGF or agonists or antagonists thereof as may be required for the particular condition, into the body of patients in need thereof. Finally, the present invention includes a device for preventing or treating cancer, other hematological disorders, neutropenias, immunodeficiency disorders, autoimmune disorders, and the like, by implantation into a patient of an implant comprising a semipermeable membrane, and cells that secrete Bv8 and/or EG-VEGF (or agonists or antagonists thereof as may be required for the particular condition) encapsulated within said membrane and said membrane being permeable to Bv8 and/or EG-VEGF (or agonists or antagonists thereof) and impermeable to factors from the patient detrimental to the cells. The patient's own cells, transformed to produce Bv8 and/or EG-VEGF ex vivo, could be implanted directly into the patient, optionally without such encapsulation. The methodology for the membrane encapsulation of living cells is familiar to those of ordinary skill in the art, and the preparation of the encapsulated cells and their implantation into patients may be accomplished without undue experimentation.

The pharmaceutical composition comprising Bv8, EG-VEGF, or a combination thereof, or agonists or antagonists thereof, is preferably located in a suitable container. The container is preferably accompanied by instructions detailing the appropriate use and dosage of the pharmaceutical composition. One skilled in the art will recognize that these instructions will vary depending upon the method of treatment.

I. Methods of Treatment

Bv8, EG-VEGF, and their agonists and antagonists provided herein may be used in a number of diagnostic assays and treatments. Bv8 and/or EG-VEGF induce proliferation of bone marrow cells and their progeny, including but not limited to, hematopoietic stem cells, CD34+ myeloid progenitor cells, CD34+ lymphoid progenitor cells, myeloid precursor cells, lymphoid precursor cells, monocytes, and lymphocytes. This proliferation leads to an increase in the number of white blood cells, including B cells, T cells, macrophages, and in particular, neutrophils.

Bv8, EG-VEGF, and their agonists are therapeutically useful, for example, in the treatment of disorders or conditions where it is desirable to increase proliferation of bone marrow cells and their progeny, including but not limited to myeloid progenitor cells, myeloid precursor cells, neutrophils, lymphoid progenitor cells, lymphoid precursor cells, and lymphocytes, or enhance the survival of particular types of blood cells, such as neutrophils, B cells, or T cells. In an embodiment, Bv8, EG-VEGF, or an agonist thereof is administered to a mammal in an amount effective to treat the disease or disorder. Preferably, the mammal is a human. Bv8, EG-VEGF, or a combination thereof may be administered in a polypeptide or nucleic acid form.

For example, Bv8, EG-VEGF, and their agonists are therapeutically useful for treating conditions and disorders associated with neutropenia, lymphopenia, or immunodeficiency disorders, which may be primary or secondary immunodeficiency disorders. These conditions and disorders may be associated, for example, with genetic disorders, B cell deficiencies, T cells deficiencies, infectious diseases including bacterial and viral infection, infiltrative and hematological disorders, surgery and trauma, and administration of a therapeutic agent that has a secondary immunosuppressive effect. In some instances the secondary immunosuppressive effect results in an immunodeficiency disorder. Bv8, EG-VEGF, or a combination thereof may be used to promote hematopoietic recovery from myelosuppression, for example, in cancer patients undergoing therapeutic treatments wherein the therapeutic agents severely lower the level of circulating leukocytes and compromise the patient's immune system. Bv8, EG-VEGF, or a combination thereof may be administered prior to, in combination with, or subsequent to radiation, high dose chemotherapy, or other anti-cancer drugs to promote hematopoietic recovery and/or increase the number of circulating neutrophils, B cells, and T cells.

Bv8, EG-VEGF, or a combination thereof may be administered with another compound or composition. Bv8 and/or EG-VEGF may be administered prior to, during, or after treatment with the compound or composition such that the therapeutic efficacy of Bv8, EG-VEGF, and/or the compound or composition is increased. As described above, the compound or composition may be a chemotherapeutic agent. Preferred chemotherapeutic agents include but are not limited to vincristine, cisplatin, oxoplatin, methotrexate, 3'-azido-3'-deoxythymidine, taxanes (e.g. paclitaxel (TAXOL®, Bristol-Myers Squibb Oncology, Princeton, N.J.), and doxetaxel (TAXOTERER®, Rhône-Poulenc Rorer, Antony, France)) and/or anthracycline antibiotics. The manufacturers' instructions may be followed in determining the preparation and dosing schedules for such chemotherapeutic agents or they may be determined empirically by the skilled practitioner. Preparation and dosing schedules for such chemotherapy are also described in Chemotherapy Service Ed., M. C. Perry, Williams & Wilkins, Baltimore, Md. (1992).

In another embodiment. Bv8, EG-VEGF, or a combination thereof is administered with VEGF or an agonist thereof. The VEGF may be a receptor selective mutant of VEGF. In one embodiment the compound is a FLT1 receptor selective mutant of VEGF or an agonist thereof. In another embodiment, the compound is a KDR receptor selective mutant of VEGF or an agonist thereof.

Antagonists of Bv8 and EG-VEGF and combinations thereof may be therapeutically useful for treating hematological disorders associated with abnormal proliferation or differentiation of bloods. The abnormal proliferation or differentiation may result in dysplastic changes in bloods cells and hematological malignancies. Specific embodiments include treating leukemia, myeloproliferative disorders, myelodysplastic syndromes, lymphoproliferative disorders, and lymphodysplastic disorders in a patient. Cells in various leukemic disorders, such as ALL, AML, MPD, CML, and MDS cells, have been found to express receptors for Bv8 and EG-VEGF. Antagonists of Bv8 and EG-VEGF are useful to inhibit proliferation of these leukemic cells.

Bv8 and EG-VEGF induce B and T cell activation. Agonists and antagonists of these molecules are therapeutically useful to modulate an immune response. Bv8, EG-VEGF or a combination thereof or agonists thereof may be administered to induce proliferation and/or activation of B lymphocytes, CD4+ T lymphocytes, and/or CD8+ T lymphocytes. Antagonists of Bv8 and EG-VEGF may be administered to inhibit proliferation and/or activation of B lymphocytes, CD4+ T lymphocytes, and/or CD8+ T lymphocytes.

Bv8 and/or EG-VEGF may promote or inhibit proliferation and activation of CD4+ T lymphocytes. Bv8 and EG-VEGF induce cytokine production in CD4+ T lymphocytes. In an embodiment, the cytokines are IL-2 and/or IFN-γ. Bv8 or EG-VEGF agonists that selectively induce IL-2 synthesis in CD4+ T lymphocytes may be useful to induce proliferation of CD4+ T cells. Bv8 or EG-VEGF agonists that selectively induce IFN-γ synthesis in CD4+ T lymphocytes by may be useful to inhibit proliferation of CD4+ T cells.

Bv8 antagonists, EG-VEGF antagonists, and combinations thereof may be useful to treat autoimmune disorders where a decrease in the number of activated B cells, CD4+ T cells, and/or CD8+ T cells is desirable. Specific embodiments include using the agents and compositions provided herein to treat type II, III, and IV hypersensitivity responses associated with autoimmune disorders. In a preferred embodiment, the autoimmune disorder is inflammatory bowel disease, Crohn's disease, colitis, or graft versus host disease.

Compounds such as those identified by the screening assays in section 4 and 5, above, may be used to modulate the level of Bv8 and/or EG-VEGF activity or expression. Specifically, compounds identified that are Bv8 agonists and/or EG-VEGF or that are able to stimulate the binding of Bv8 and/or EG-VEGF to its receptors may be useful for treatments wherein an increased level of Bv8 and/or EG-VEGF activity is desired. Similarly, compounds identified that are able to increase Bv8 gene expression, EG-VEGF gene expression, or a combination thereof, may be useful for this type of treatment. Bv8 agonists and/or EG-VEGF agonists and compounds that increase Bv8 and/or EG-VEGF gene expression may be useful to treat neutropenia, lymphopenia, and immunodeficiency disorders, where an increase in the number of neutrophils, B lymphocytes, and/or T lymphocytes is desirable.

Compounds, such as Bv8 antagonists and/or EG-VEGF antagonists identified by the screening assays in section 4 and 5 above, may be used to modulate the level of Bv8 and/or EG-VEGF activity or expression, respectively, as described herein. Compounds, such as Bv8 agonists and/or EG-VEGF agonists identified by the screening assays in section 4 and above, may be useful to modulate an immune response as described herein.

It is understood that the methods of increasing bone marrow cell proliferation and inhibiting bone marrow cell proliferation can be performed in vivo or in vitro. In some cases, it may be desirable to add Bv8, EG-VEGF, or a combination thereof to a cell sample in vitro so as to stimulate proliferation of a specific cell type. The sample treated with Bv8, EG-VEGF, or a combination thereof can then be used in screening assays or be transplanted into an individual in need of treatment or into an animal model.

An effective amount of Bv8 or a Bv8 agonist or antagonist, EG-VEGF or an agonist or antagonist thereof, to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer the Bv8 and/or EG-VEGF until a dosage is reached that achieves the desired effect. A typical daily dosage for systemic treatment may vary from about 10 µg/kg to up to 100 mg/kg of mammal body weight or more per day, preferably about 1 µg/kg/day to 10 mg/kg/day, depending upon the route of administration. It is anticipated that different formulations will be effective for different treatment compounds and different disorders, and that administration targeting one organ or tissue, for example, may necessitate delivery in a manner different from that to another organ or tissue.

Alternatively, Bv8 and/or EG-VEGF is formulated and delivered to the target site or tissue at a dosage capable of establishing in the tissue a level of Bv8 and/or EG-VEGF that is efficacious but not unduly toxic. This intra-tissue concentration should be maintained if possible by continuous infusion, sustained release, topical application, cell implant expressing Bv8 and/or EG-VEGF, or injection at empirically determined frequencies. The progress of this therapy is easily monitored by conventional assays.

The dosing regimen must be determined based on the individual circumstances. However, in a preferred embodiment, Bv8 and/or EG-VEGF, or an agonist or antagonist thereof, is administered every day, more preferably every other day and even more preferably at least two times a week. The treatment is preferably continued for six months, more preferably for one month and even more preferably for at least two weeks. One skilled in the art will appreciate that the exact dosing regimen must be determined by the therapist based on the individual circumstances.

Polynucleotides encoding Bv8 and/or EG-VEGF polypeptide may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., 1986, *Proc. Natl. Acad. Sci. USA* 83:4143-4146). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion. DEAE-dextran, the calcium phosphate precipitation method, etc. The currently preferred in vivo gene transfer techniques include transfection with viral (typically retroviral) vectors and viral coat protein-liposome mediated transfection (Dzau et al., 1993, *Trends in Biotechnology* 11, 205-210). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., 1987, *J. Biol. Chem.* 262, 4429-4432; and Wagner et al., 1990, *Proc. Natl. Acad. Sci. USA* 87, 3410-3414. For review of gene marking and gene therapy protocols see Anderson et al., 1992, *Science* 256, 808-813.

Peptide or nucleic acid sequences encoding Bv8 and/or EG-VEGF sequence can also be used in methods of diagnosis. Abnormal expression of Bv8 and/or EG-VEGF may indicate abnormalities in hematopoiesis, onset of hematological disorders, onset of neutropenia, onset of immunodeficiency disorders, or onset of autoimmune disorders. Moreover, a sample from a patient may be analyzed for mutated or dysfunctional Bv8 and/or EG-VEGF. Generally, such methods include comparing Bv8 expression and/or EG-VEGF expression in a sample from a patient to that of a control.

J. Articles of Manufacture

In another aspect the invention contemplates an article of manufacture comprising materials useful for the treatment or prevention of a disease or disorder. The article of manufacture preferably comprises a container and a label or package insert on or associated with the container. Suitable containers include, for example, bottles, vials, syringes etc. The containers may be formed from a variety of materials such as glass and plastic. The container holds a composition comprising Bv8 and/or EG-VEGF, or an agonist or antagonist thereof, and the label or package insert preferably provides instructions for using the Bv8 and/or EG-VEGF, or an agonist or antagonist thereof. In one embodiment, the article of manufacture comprises a Bv8 antagonist and/or EG-VEGF antagonist, and instructions for using the antagonist to treat or prevent hematological disorders such as leukemia myeloproliferative disorders, myelodysplastic disorders, and the like. In another embodiment, the article of manufacture comprises Bv8 and/or EG-VEGF and instructions for using the polypeptide to treat or prevent a condition that is associated with abnormal hematopoiesis. In yet another embodiment, the article of manufacture comprises Bv8 and/or EG-VEGF and instructions for using the polypeptide to treat an immunodeficiency disorder. The package insert may also indicate the appropriate dosing regimen. In one embodiment the insert indicates that the composition is to be administered in a dose of between about 0.01 µg/kg and 50 mg/kg.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

All references cited herein are hereby incorporated by reference.

Example 1

Expression Analyses of Bv8 and its Receptors

To elucidate the expression pattern of Bv8, Dot blot analysis was performed on RNA arrays representing a panel of tissues and cell lines, from a wide variety of human, mouse and rat tissues. Tissue/cell RNA arrays and blots were purchased from CLONTECH. cDNA probes were prepared using 50 ng of human or mouse Bv8 coding sequence with methods described previously (LeCouter et al., 2001, Nature). As shown in FIG. 13, Bv8 expression appeared restricted to peripheral blood leukocytes, bone marrow tissues and the previously characterized testis (LeCouter et al., 2003, PNAS).

To identify the cell types that express hBv8, in situ hybridization (ISH) experiments were performed using a series of inflammatory tissue specimens, in which increased level of leukocytes were present. Tissues were processed for ISH and [$^{33}$P]UTP-labeled RNA probes were generated using standard methods and materials. Sense and antisense probes for hBv8 were synthesized from a cDNA fragment corresponding to nucleotides 533-1132; mBv8, nucleotides 886-1611; and mR-1, nucleotides 220-946. This probe is 81.2% identical to mR-2. Within both the inflammatory tonsils and the inflammatory appendix, strong hybridization signals of Bv8 were detected mainly in neutrophils and associated infiltrating cells (FIG. 14).

To confirm the cellular expression pattern of Bv8 and its receptors, real time quantitative PCR analyses (Heid et al., 1996, Genome Res., 6:986-994) were performed in hematopoietic cells and leukemia cell lines. Total RNA was prepared from human and mouse hematopoietic stem cells, lineage-committed progenitor cells or leukemia cell lines using the RNeasy kit and following the manufacturer's instructions. Human cell preparations were purchased from AllCells Inc. (Berkeley, Calif.), lineage committed mouse cells and stem cells (Sca+c-Kit+) were prepared from a pool of 28 femurs and sorted as previously described (Gerber, 2002, Nature). Human cell lines (HL-60. K562, Hel-92, TF-1 and KG-1) were obtained from the ATCC. For real-time RT-PCR analyses, 100 ng of total RNA was used. For both mouse and human samples, standard curves were generated using testis RNA.

| | | | |
|---|---|---|---|
| Human (h) GADPH | Forward Reverse Probe | 5' TGGGCTACACTGAGCACCAG 3' 5' CAGCGTCAAAGGTGGAGGAG 3' 5' FAM-TGGTCTCCTCTGACTTCAACAGCGACAC-TAMRA 3' | SEQ ID NO: 11 SEQ ID NO: 12 SEQ ID NO: 13 |
| Human (h) Bv8 | Forward Reverse Probe | 5' CCATTTTTTGGGCGGAGG 3' 5' CCGTAAACAGGCCAAGCCT 3' 5' FAM-TGCATCACACTTGCCCATGTCTG C-TAMRA 3' | SEQ ID NO: 14 SEQ ID NO: 15 SEQ ID NO: 16 |
| hEG-VEGF | Forward Reverse Probe | 5' CCGGCAGCCACAAGGTC 3' 5' TGGGCAAGCAAGGACAGG 3' 5' FAM-CCTTCTTCAGGAAACGCAAGCACCAC-TAMRA 3' | SEQ ID NO: 17 SEQ ID NO: 18 SEQ ID NO: 19 |
| hBv8/EG-VEGF Receptor-1 | Forward Reverse Probe | 5' GGCGCCCTTCTACGGCT 3' 5' TCTCCTTCACGAACACGGTG 3' 5' FAM-CACCATCGTGCGCGACTTCTTCC-TAMRA 3' | SEQ ID NO: 20 SEQ ID NO: 21 SEQ ID NO: 22 |
| hBv8/EG-VEGF Receptor-2 | Forward Reverse Probe | 5' GGAAATGACATCTGTGTTCATGC 3' 5' TCATTGTATGTTACGACTTTGCAGC 3' 5' FAM-CCCGTGCCCTCAAGAAGCCGA-TAMRA 3' | SEQ ID NO: 23 SEQ ID NO: 24 SEQ ID NO: 25 |
| Mouse (m) GADPH | Forward Reverse Probe | 5' ATGTTCCAGTATGACTCCACTCACG 3' 5' GAAGACACCAGTAGACTCCACGACA 3' 5' FAM-AAGCCCATCACCATCTTCCAGGAGCGAGA-TAMRA 3' | SEQ ID NO: 26 SEQ ID NO: 27 SEQ ID NO: 28 |
| Mouse (m) Bv8 | Forward Reverse Probe | 5' CGGAGGATGCACCACACC 3' 5' CCGGTTGAAAGAAGTCCTTAAACA 3' 5' FAM-CCCCTGCCTGCCAGGCTTGG-TAMRA 3' | SEQ ID NO: 29 SEQ ID NO: 30 SEQ ID NO: 31 |
| mEG-VEGF | Forward Reverse Probe | 5' TGAGGAAACGCCAACACCAT 3' 5' CCGGGAACCTGGAGCAC 3' 5' FAM-CCTGTCCCTGCTCACCCAGCCTG-TAMRA 3' | SEQ ID NO: 32 SEQ ID NO: 33 SEQ ID NO: 34 |
| mBv8/EG-VEGF Receptor-1 | Forward Reverse Probe | 5' CAGCGCACATGAAGACTTG 3' 5' GTCATCTTCGGTTTCCTGAGT 3' 5' FAM-TCCAGGCAGCACCCCTGATG-TAMRA 3' | SEQ ID NO: 35 SEQ ID NO: 36 SEQ ID NO: 37 |
| mBv8/EG-VEGF Receptor-2 | Forward Reverse Probe | 5' GAACTCCACGTGAGCGCA 3' 5' GGGTCCCATGTTGATGATGCT 3' 5' FAM-CTCCCTGATACACACCAGCCCACCTG-TAMRA 3' | SEQ ID NO: 38 SEQ ID NO: 39 SEQ ID NO: 40 |

Figure 15A:
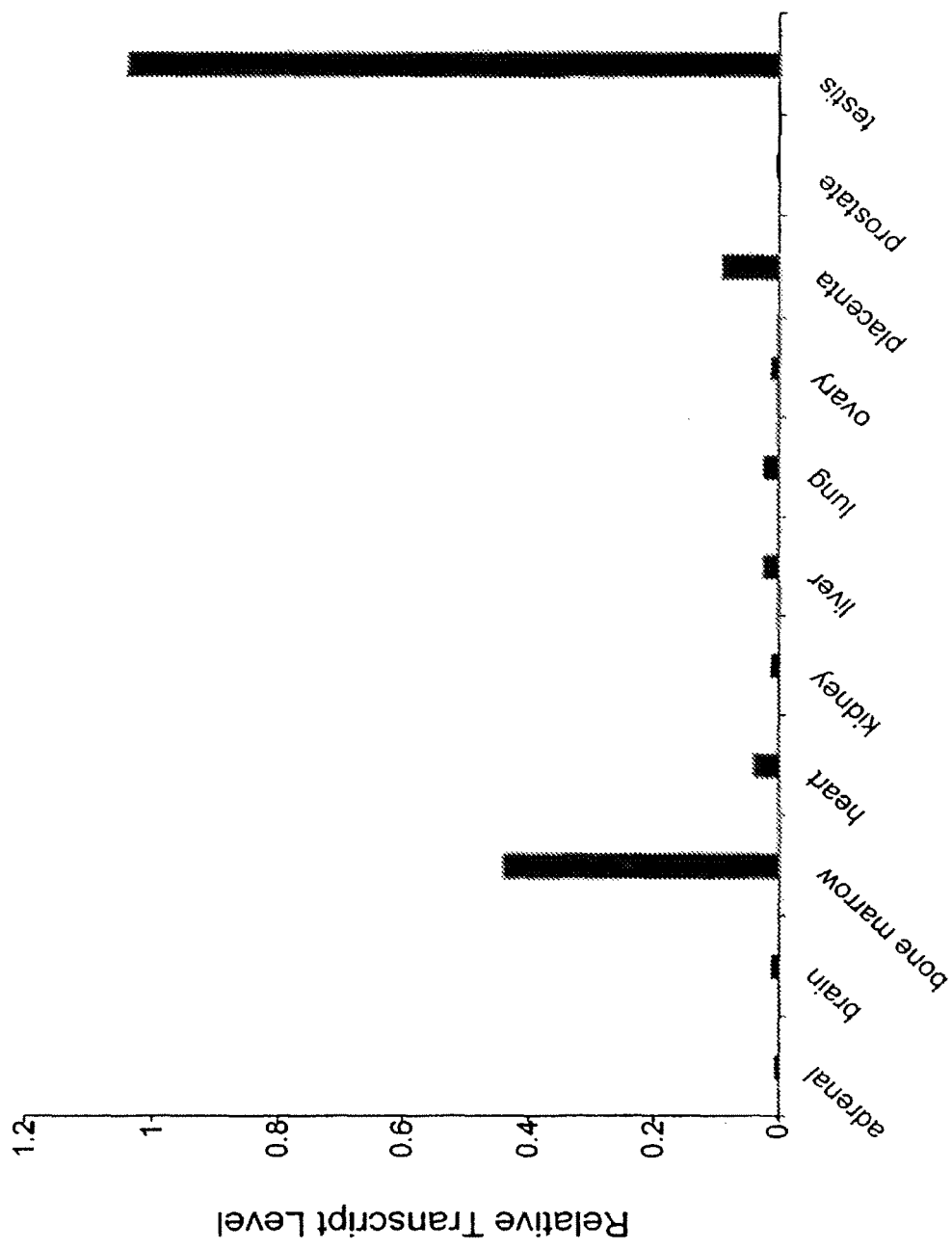
FIGS. 15A-D are graphs showing the results of real time quantitative PCR expression analysis of Bv8 and its receptors in various tissues and cells.
Figure 15B:
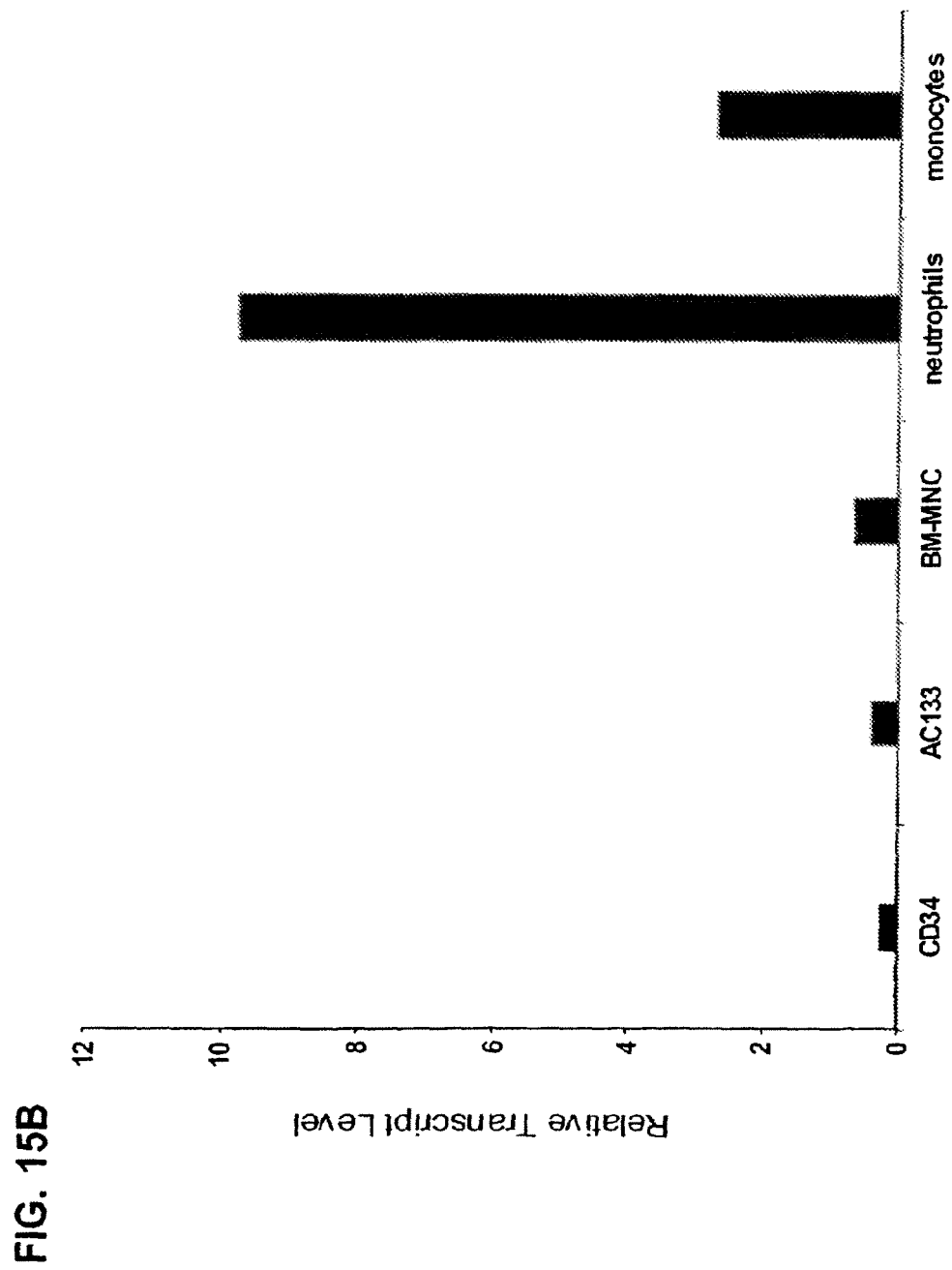
Figure 15C:
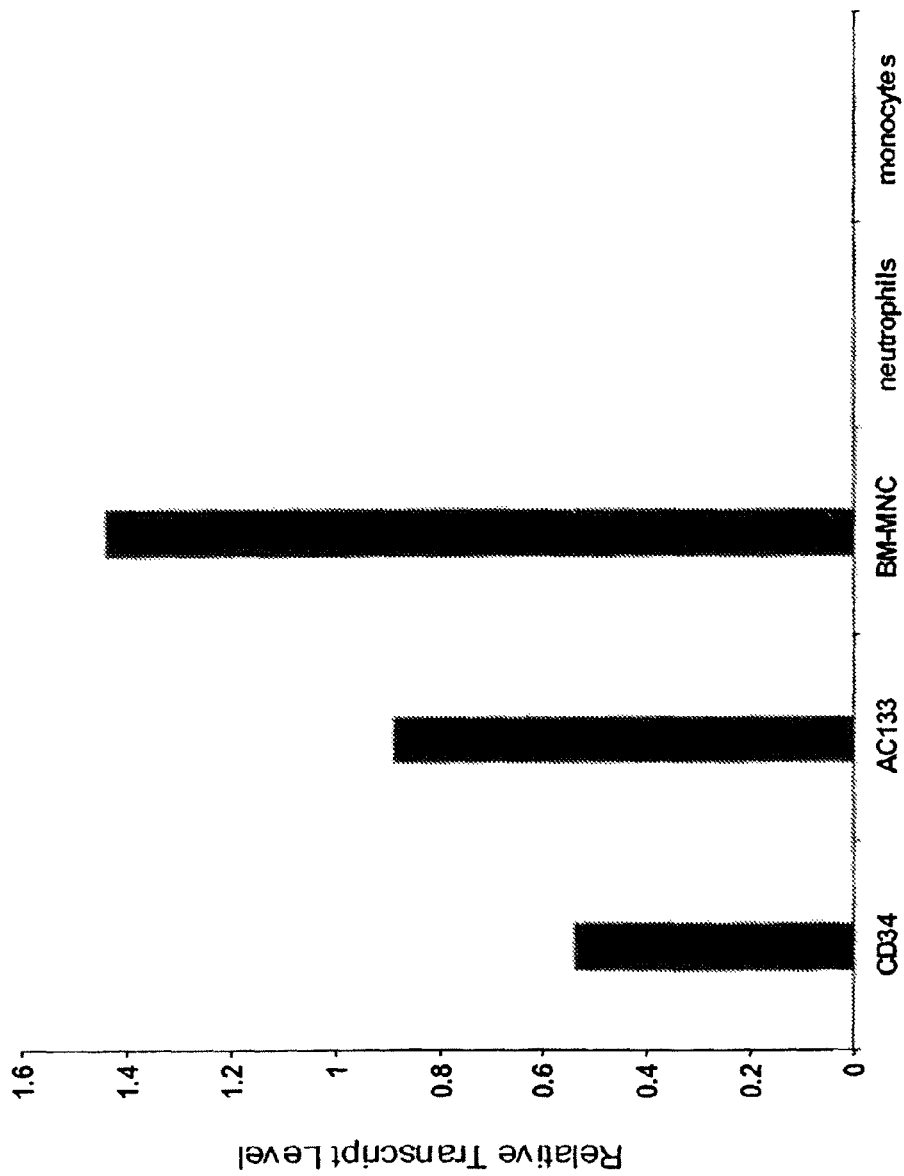
Figure 15D:
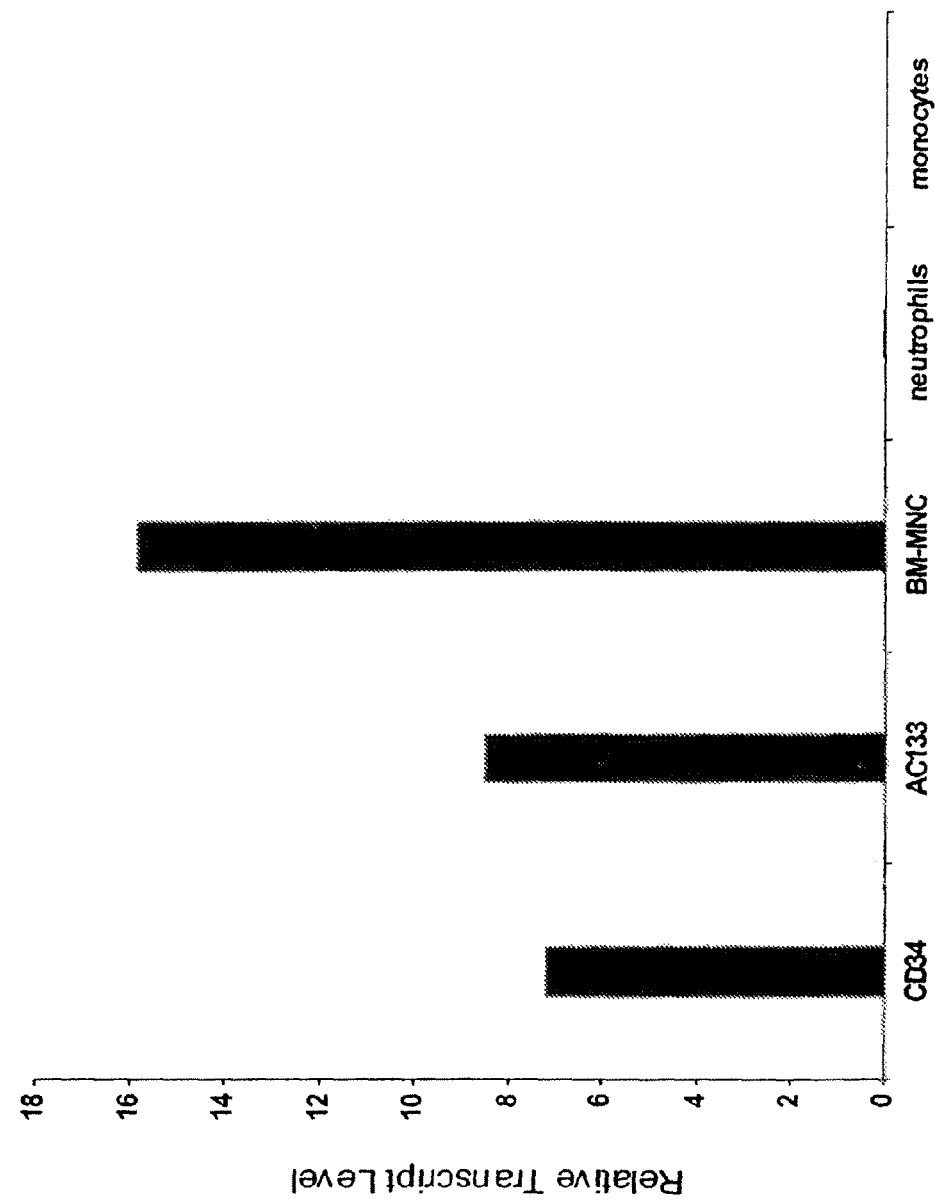

As shown in FIGS. 15A-D, hBv8 mRNA is most prominently expressed in bone marrow and testis, whereas placenta expresses about 10% of the level in testis (FIG. 15A). Among different hematopoietic cell types, hBv8 mRNA is prominently expressed in neutrophils, with moderate expressions in monocytes and bone marrow-mononuclear cells as well (FIG. 15B). In comparison, both the Bv8/EG-VEGF receptor 1 and receptor 2 are expressed at high levels in CD34+ cells, AC133 and BM-MNCs, but not in neutrophils or monocytes (FIGS. 15C, D).

Figure 16:
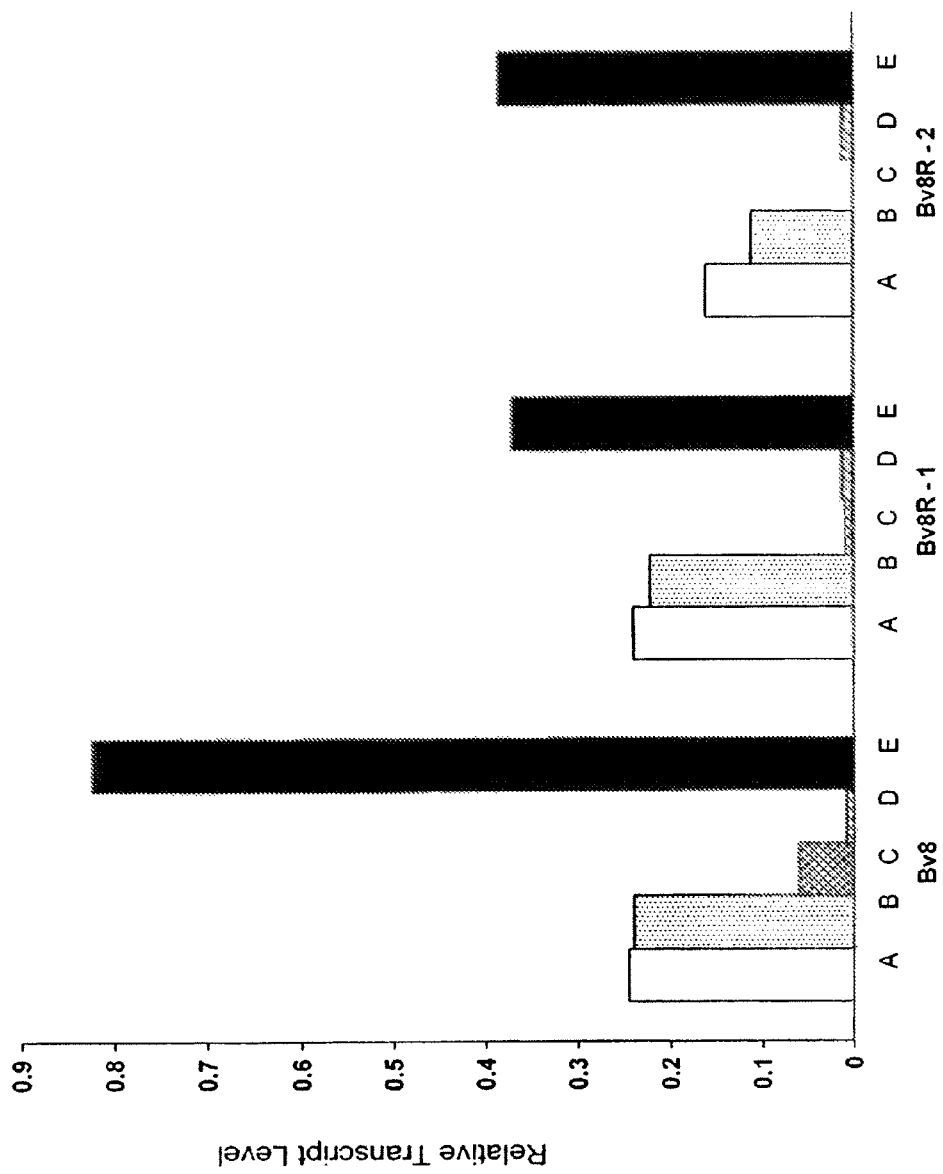
FIG. 16 is a bar graph showing the results of real time quantitative PCR expression analysis of Bv8 and Bv8/EG-VEGF receptor-1 and Bv8/EG-VEGF receptor-2 in various leukemia cell lines (A) HL60 CML; (B) K562CML; (C) Hel-92 erythroleukemia; (D) TF-1 pancytopenia; (E) KG-1 AML.

Expression of hBv8 and hBv8/EG-VEGF receptors was also studied in various leukemia cell lines using real time quantitative PCR analysis. As shown in FIG. 16, certain leukemia cell lines (such as HL60 CML, K562 CML and KG-1 AML) express significant levels of both Bv8 and its receptors.

Example 2

Colony Formation Assays

The biological functions of Bv8 in mouse and human hematopoietic cells were studied using a methylcellulose colony formation assay. Mouse bone marrow mononuclear cells were collected by flushing the femurs of mice with 3 ml of cold (4 C) Iscove's MDM containing 20% FCS. Red blood cells were lysed with 10 mM $NH_4Cl$ in 10 mM Tris pH7.2 on ice for 10 minutes. The remaining mononuclear cells were washed in media and pelleted by centrifugation. For methylcellulose cultures, 70,000 cells were plated on each 35 mm grided-plate in media preparations (MethoCult M3434, a complete media containing SCF, IL-3, IL-6 and Epo and M3334, a basal media containing Epo alone) all purchased from StemCell Technologies Inc. according to the manufacturer's instructions. Mouse IL-3, IL-6 and SCF were purchased from StemCell Technologies Inc., and VEGF, EG-VEGF and Bv8 were produced at Genentech as previously described (LeCouter et al., 2001, *Nature*, 412:877-884; LeCouter et al., 2003, *Proc. Natl. Acad. Sci. USA*, 100:2685-2690). Final concentrations of exogenous factors were as follows: 10 ng/ml mouse IL-3, 10 ng/ml mouse IL-6, 50 ng/ml mouse SCF, 10 ng ml VEGF, 5 or 50 nM EG-VEGF or 50 nM mouse Bv8. After 12 days in culture at 37 C and 5% $CO_2$, hematopoietic colonies were enumerated for triplicate samples using a light microscope.

Figure 17A:
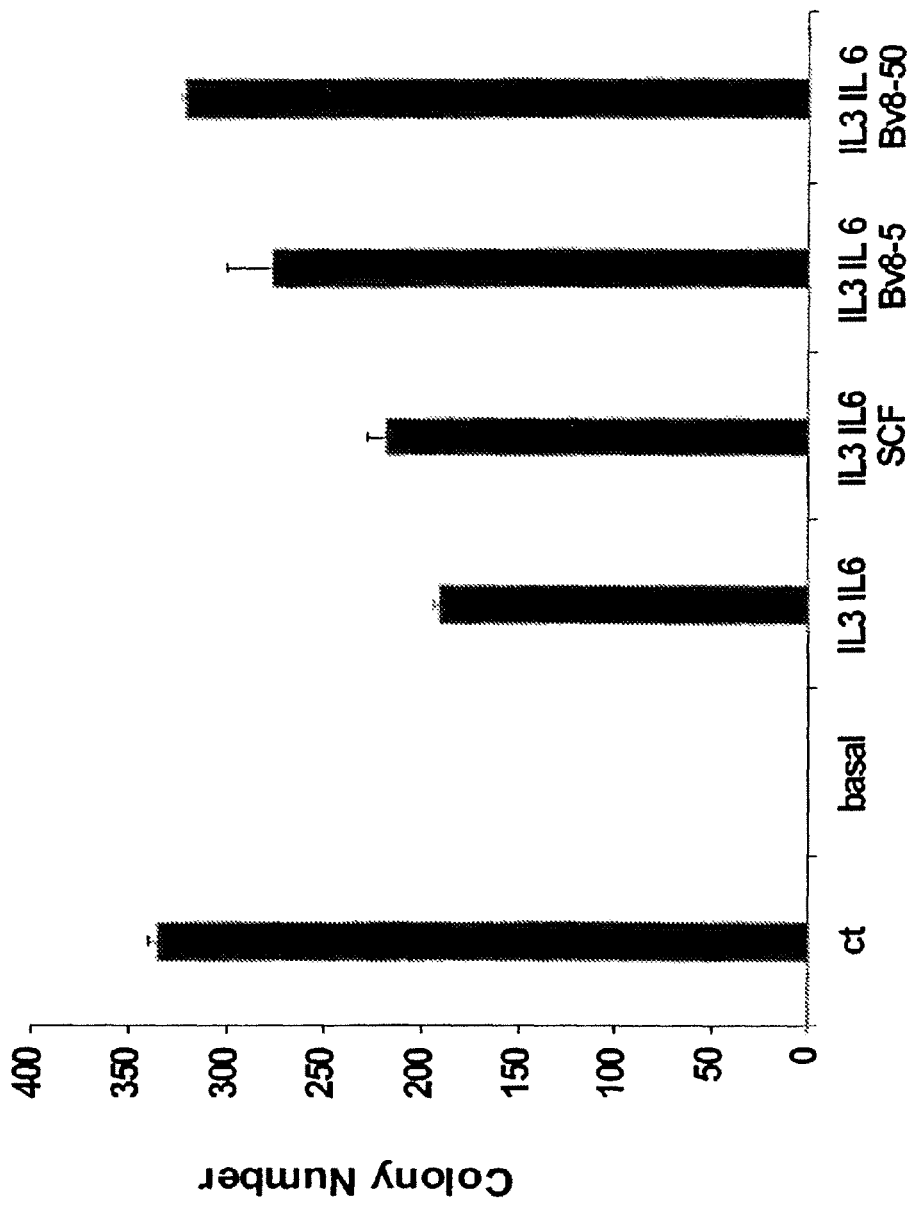
FIGS. 17A-B are graphs showing colony formations in bone marrow mononuclear cultures in vitro, in the presence of various growth factors.

As shown in FIG. 17A, addition of Bv8 at either 5 nM or 50 nM significantly increased the number of colonies formed in mouse BM-MNCs.

For human cultures, 70,000 bone marrow derived mononuclear cells (AllCells Inc.) were plated in MethoCult 4434 complete, 4330 basal media or basal media supplemented with 10 ng/ml IL-3, 10 ng/ml IL-6, 5 ng/ml G-CSF, 5 ng/ml GM-CSF, 50 nM EG-VEGF, and 50 nM Bv8, as indicated (all from StemCell Technologies Inc.). Cell colonies were identified and counted by microscopic observation following 14-16 days in culture.

Figure 17B:
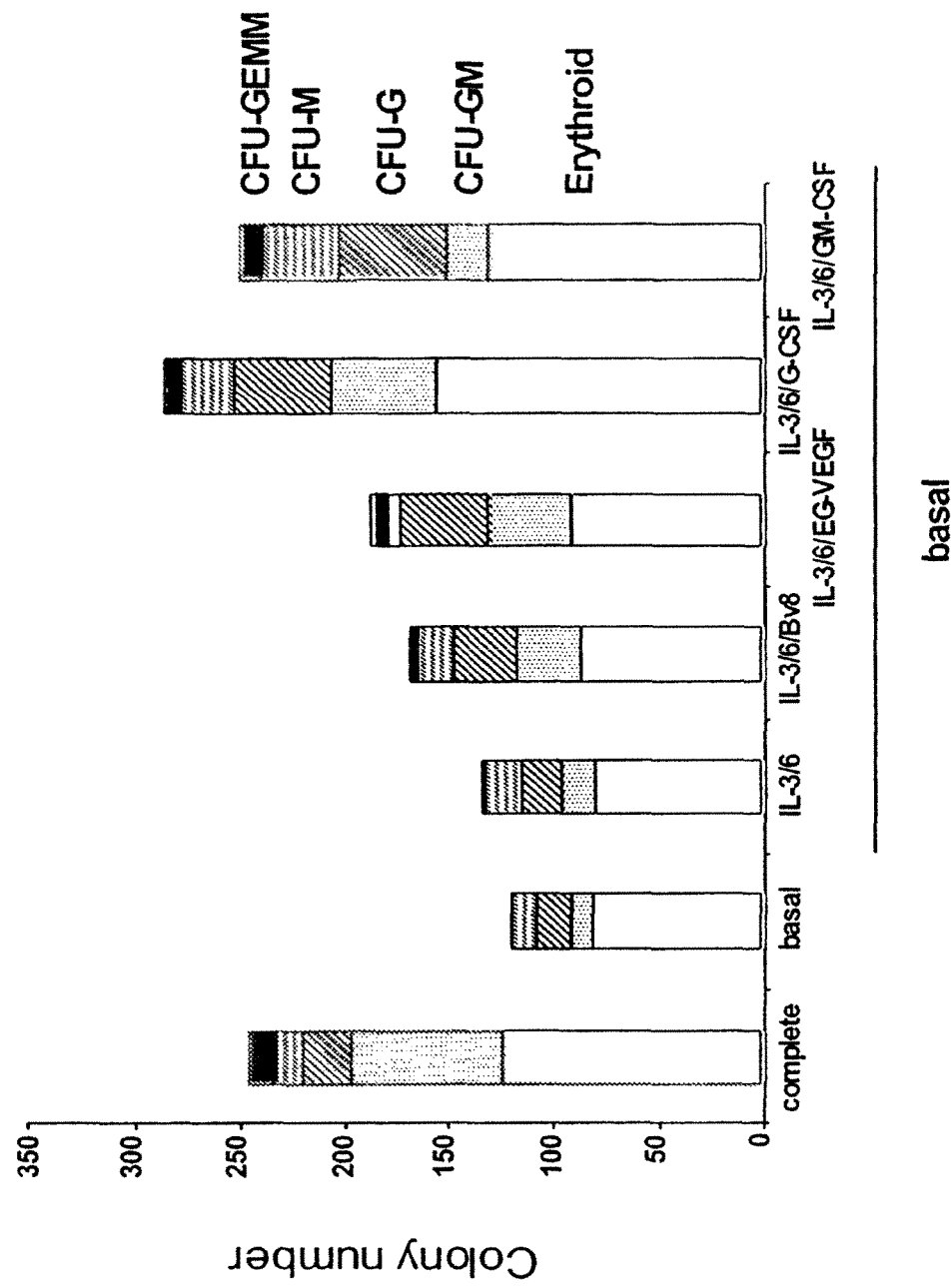

As shown in FIG. 17B, Bv8 or EG-VEGF increased colony formations of at least certain types of lineage-committed myeloid progenitor cells. For example, when Bv8 or EG-VEGF were added to the basal media supplemented with IL-3 and IL-6, colony numbers for CFU-GM cells was increased by about 1.7-fold and about 2.2-fold, respectively; CFU-G cells by about 1.7-fold and about 2.5-fold, respectively; and CFU-GEMM cells by about 4-fold and about 7-fold, respectively. It is worth of noticing that, in terms of colony numbers, these increases resembled the groups treated with G-CSF, a well known granulocyte colony-stimulating factor.

Example 3

Cell Mobilization Assays

Immunodeficient (nude) mice were injected via the tail vein with Adenovirus encoding LacZ ($5 \times 10^8$ pfu), VEGF ($10^7$ pfu), EG-VEGF ($5 \times 10^8$ pfu) or Bv8 ($5 \times 10^8$ pfu). This route of administration was employed to achieve systemic production of the secreted factors. To assess HSC mobilization, blood samples were collected from the retro-orbital sinus at days 3, 6 and 12, and differential blood cell counts were determined using a Coulter counter. At necropsy sessions on days 6 and 12, body weight and organ weights were determined. Bv8 enhanced the survival of BBC epithelial cells. In particular, fewer apoptotic cells were visible in culture in the presence of either concentration of Bv8 than in the presence of 2% FCS or 25 nM EG-VEGF. Bv8 and VEGF showed a synergistic effect, with a combination of the two compounds increasing cell survival to a greater extent than either growth factor on its own or 10% FCS.

Figure 18:
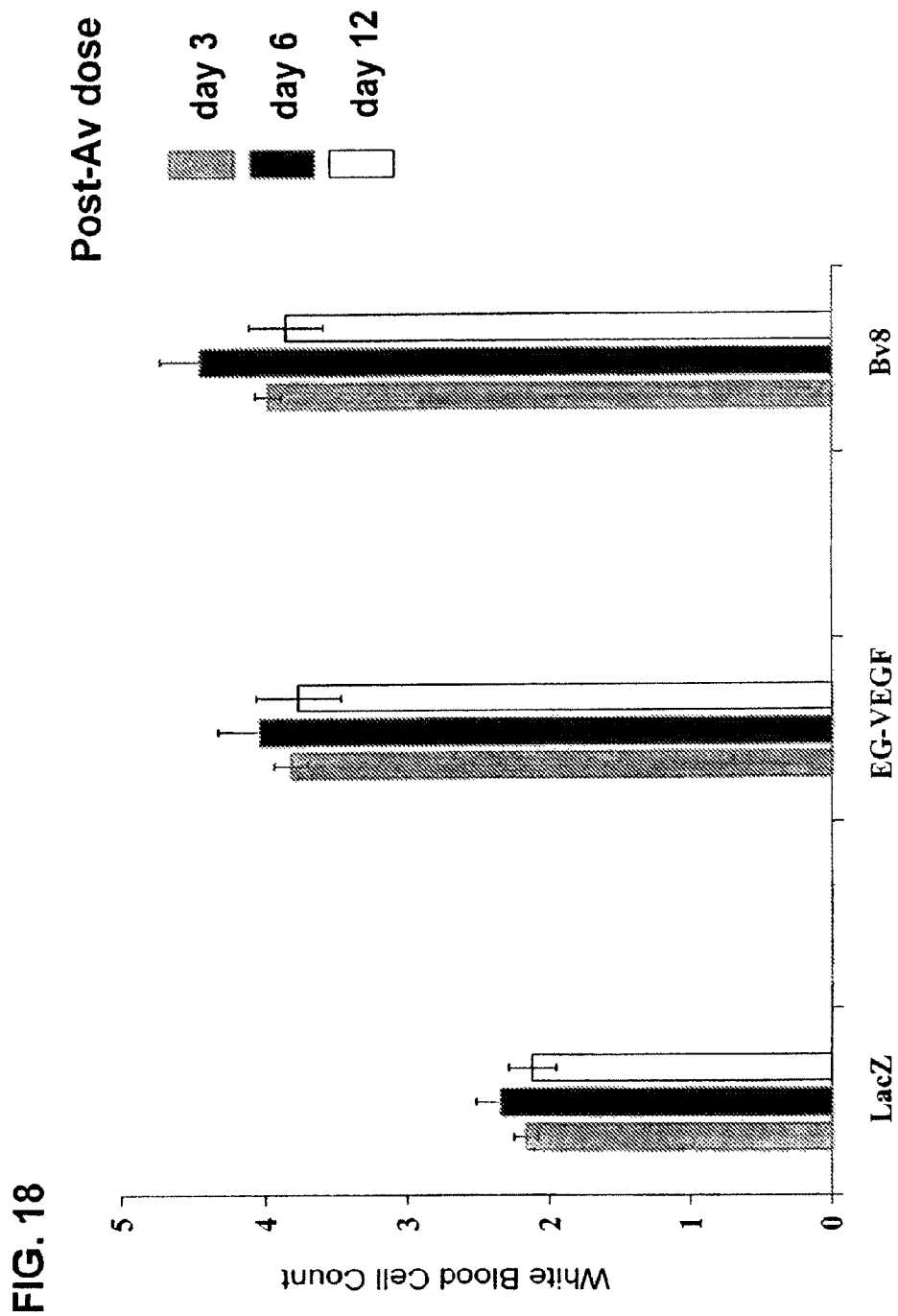
FIG. 18 is a graph showing that Bv8, similar to EG-VEGF, increases white blood cell count in vivo. Cell counts were measured at 3 days (light gray), 6 days (dark gray), or 12 days (open bar) after in vivo introduction of Bv8-expressing adenoviral vectors.

As shown in FIG. 18, adenoviral-Bv8 injection resulted in increase of white blood cell counts by about 2 to about 2.5 fold. Meanwhile, the counts of red blood cells or platelets did not have any significant changes. Similar effects can be seen when EG-VEGF expression was introduced by adenoviral injection.

Example 4

Bv8/EG-VEGF Receptor Expression in Lymphocytes

Expression of Bv8/EG-VEGF and their respective receptors by human and murine lymphocytes was studied using Real time quantitative PCR analysis. Acutely isolated human and mouse purified cells and human cells from commercially available preparations (AllCells Inc., Berkeley, Calif.) were analyzed for receptor expression. B cells, $CD4^+$ T cells, $CD8^+$ T cells, and natural killer cells were positively selected using an appropriate antibody (anti-CD19, anti-CD4, anti-CD8, and anti-CD56 antibodies respectively) conjugated to paramagnetic beads (Miltenyi Biotec, Auburn, Calif.). Briefly, $10^7$ total cells in 90 µl of MACS buffer (PBS with 0.5% bovine serum albumin and 2 mM EDTA) and 10 µl antibody-conjugated paramagnetic beads were incubated at 4° C. for 15 minutes. The beads were then washed in an excess of MACS buffer, centrifuged at 300×g for 10 minutes, and the pellet resuspended in 2 ml of MACS buffer. The cell suspension was then applied to a LS+/VS+ selection column (Miltenyi Biotec, Auburn, Calif.) that had been placed in the magnetic field of a MACS separator (Miltenyi Biotec, Auburn, Calif.). The column was rinsed two times with 3 ml of MACS buffer, removed from the separator, and the positive cell fraction flushed from the column with MACS buffer using the plunger supplied with the column.

Total RNA was prepared from positively selected cells using a RNeasy kit (Qiagen, Valencia, Calif.) following the manufacturer's instructions. At least two independently purified human and mouse RNA isolates were analyzed in these studies with similar results. For real time quantitative PCR analysis, 50 ng of total RNA served as template for reactions that assessed expression of EG-VEGF, Bv8, and their cognate receptors Bv8/EG-VEGF receptor-1 and Bv8/EG-VEGF receptor-2 (LeCouter et al., 2003, *Proc. Natl. Acad. Sci. USA*, 100:2685-2690). For both mouse and human samples, standard curves were generated using testis RNA. Primers and probes used in the analysis were as follows:

| | | | | |
|---|---|---|---|---|
| Human (h) Bv8 | Forward | 5' | CCATTTTTTGGGCGGAGG 3' | SEQ ID NO: 14 |
| | Reverse | 5' | CCGTAAACAGGCCAAGCCT 3' | SEQ ID NO: 15 |
| | Probe | 5' | FAM-TGCATCACACTTGCCCATGTCTG C-TAMRA 3' | SEQ ID NO: 16 |
| hEG-VEGF | Forward | 5' | CCGGCAGCCACAAGGTC | SEQ ID NO: 17 |
| | Reverse | 5' | TGGGCAAGCAAGGACAGG | SEQ ID NO: 18 |
| | Probe | 5' | FAM-CCTTCTTCAGGAAACGCAAGCACCAC-TAMRA 3' | SEQ ID NO: 19 |
| hBv8/EG-VEGF Receptor-1 | Forward | 5' | GGCGCCCTTCTACGGCT 3' | SEQ ID NO: 20 |
| | Reverse | 5' | TCTCCTTCACGAACACGGTG 3' | SEQ ID NO: 21 |
| | Probe | 5' | FAM-CACCATCGTGCGCGACTTCTTCC-TAMRA 3' | SEQ ID NO: 22 |
| hBv8/EG-VEGF Receptor-2 | Forward | 5' | GGAAATGACATCTGTGTTCATGC 3' | SEQ ID NO: 23 |
| | Reverse | 5' | TCATTGTATGTTACGACTTTGCAGC 3' | SEQ ID NO: 24 |
| | Probe | 5' | FAM-CCCGTGCCCTCAAGAAGCCGA-TAMRA 3' | SEQ ID NO: 25 |
| Mouse (m) Bv8 | Forward | 5' | CGGAGGATGCACCACACC 3' | SEQ ID NO: 29 |
| | Reverse | 5' | CCGGTTGAAAGAAGTCCTTAAACA 3' | SEQ ID NO: 30 |
| | Probe | 5' | FAM-CCCCTGCCTGCCAGGCTTGG-TAMRA 3' | SEQ ID NO: 31 |
| mEG-VEGF | Forward | 5' | TGAGGAAACGCCAACACCAT 3' | SEQ ID NO: 32 |
| | Reverse | 5' | CCGGGAACCTGGAGCAC 3' | SEQ ID NO: 33 |
| | Probe | 5' | FAM-CCTGTCCCTGCTCACCCAGCCTG-TAMRA 3' | SEQ ID NO: 34 |
| mBv8/EG-VEGF Receptor-1 | Forward | 5' | CAGCGCACATGAAGACTTG 3' | SEQ ID NO: 35 |
| | Reverse | 5' | GTCATCTTCGGTTTCCTGAGT 3' | SEQ ID NO: 36 |
| | Probe | 5' | FAM-TCCAGGCAGCACCCCTGATG-TAMRA 3' | SEQ ID NO: 37 |
| mBv8/EG-VEGF Receptor-2 | Forward | 5' | GAACTCCACGTGAGCGCA 3' | SEQ ID NO: 38 |
| | Reverse | 5' | GGGTCCCATGTTGATGATGCT 3' | SEQ ID NO: 39 |
| | Probe | 5' | FAM-CTCCCTGATACACACCA GCCCACCTG-TAMRA 3' | SEQ ID NO: 40 |

As shown in FIGS. 19A-D, human and mouse B cells, CD4+ T cells, CD8+ T cells, and natural killer cells express Bv8/EG-VEGF receptor-1 and receptor-2. These results indicate that these lymphocytes may be responsive in vivo to Bv8 and/or EG-VEGF ligand, which is primarily expressed by neutrophils.

Example 5

B Cell Proliferation Promoted by Bv8/EG-VEGF

The ability of Bv8 and/or EG-VEGF to promote the proliferation of B cells was studied. B cells were isolated from the spleens of Balb/C or C57Bl/6J mice. Spleens were harvested from the mice and mechanically dissociated between two glass slides. The cell preparation was suspended in MACS buffer (PBS with 0.5% bovine serum albumin and 2 mM EDTA) and then passed through a 40 µm nylon cell strainer. The resultant single cell suspension was applied to a Ficoll gradient (Lymphocyte M, Cedarlane Laboratories Ltd., Ontario, Canada) and centrifuged at 2500 rpm for 15 minutes. The cells at the interface were collected and washed three times in MACS buffer. B cells were then positively selected from the purified cell population using CD19 Microbeads (Miltenyi Biotec, Auburn, Calif.) as described above for Example 1.

For proliferation assays, $5 \times 10^5$ cells per well were plated in a flat-bottom 96-well plate in RPMI assay media (RMPI 1640 supplemented with 10% fetal calf serum and penicillin/streptomycin solution (Life Technologies, Inc., Rockville, Md.). Recombinant Bv8 or EG-VEGF was added to each well at a concentration ranging from 2 to 200 nM. In some wells, 20 or 30 µg/ml of anti-mouse IgM Fab fragment (Jackson ImmunoResearch, West Grove, Pa.) was added to induce basal activation of the B cells. In the positive controls, 1 µg/ml LPS (Sigma-Aldrich, St. Louis, Mo.) or 10 µg/ml Bly (Genentech, Inc., South San Francisco, Calif.) was added to each well in lieu of recombinant Bv8 and EG-VEGF. The cells were incubated at 37° C. for 72 hours and then pulsed with 1 µcurie of 3H-thymidine per ml (Amersham Biosciences, Piscataway, N.J.). Samples were collected using a Filtermate 196 Harvester (Packard, Boston, Mass.) and analyzed using a Microplate Scintillation Counter (Packard, Boston, Mass.).

Figure 20:
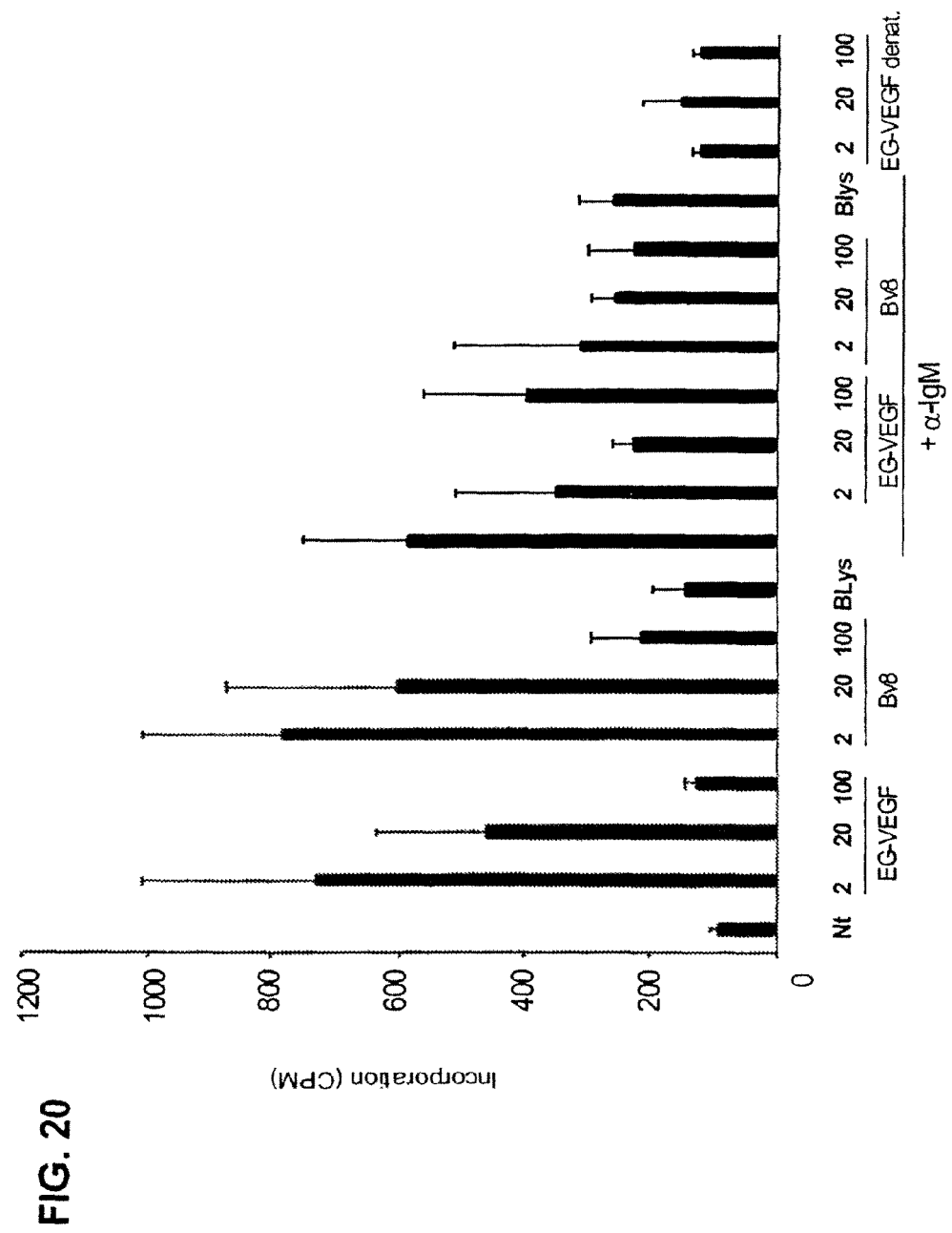
FIG. 20 is a graph showing that Bv8 and EG-VEGF increases 3H-thymidine incorporation in mouse B lymphocytes ex vivo.

Proliferation of mouse B cells was analyzed by assessing 3H-thymidine incorporation. As shown in FIG. 20, each of Bv8 and EG-VEGF reproducibly induced a 4 to 6 fold increase in 3H-thymidine incorporation in B cells. This data indicates that Bv8 and EG-VEGF function as mitogens and survival factors for B lymphocytes.

Example 6

T Cell Proliferation Promoted by Bv8/EG-VEGF

The ability of Bv8 and/or EG-VEGF to promote the proliferation of CD4+ T cells was studied. CD4+ T cells were isolated from spleens of Balb/C or C57Bl/6J mice. Spleens were harvested and mechanically dissociated as described above for Example 5. The cell preparation was then suspended in MACS buffer and purified as described above for Example 5. T cells were negatively selected from the purified cell population using a CD4+ T Cell Isolation Kit (Miltenyi Biotec, Auburn, Calif.).

Briefly, $10^7$ total cells in 90 μl of MACS buffer (PBS with 0.5% bovine serum albumin and 2 mM EDTA) and 10 μl MACS Anti-Hapten Microbeads were incubated at 4° C. for 10 minutes. The beads were then washed in an excess of MACS buffer, centrifuged at 300×g for 10 minutes, and the pellet resuspended in 2 ml of MACS buffer. The cell suspension was then applied to a LS+/VS+ selection column (Miltenyi Biotec, Auburn, Calif.) that had been placed in the magnetic filed of a MACS separator (Miltenyi Biotec. Auburn, Calif.). The effluent from the column, representing the enriched CD4+ T cell fraction, was collected. The column was rinsed four times with 3 ml of MACS buffer and the effluent representing the enriched CD4+ T cell fraction was collected. The enriched CD4+ T cell fraction was washed in MACS buffer and then resuspended in RPMI assay media.

Proliferation assays employing the negatively selected CD4+ T cells were performed as described above for Example 5. Recombinant Bv8 or EG-VEGF was added to each well at a concentration ranging from 2 to 200 nM. Some wells were precoated for 2 hours at 37° C. with 0.5 g/ml anti-mouse CD3 antibody (Pharmingen, La Jolla, Calif.) and/or 1 μg/ml anti-mouse CD28 antibody (Pharmingen, La Jolla, Calif.) in carbonate buffer, pH 9.0. The antibodies crosslinked the respective receptors on the surface of the T cells, inducing basal activation. Addition of anti-CD3 antibodies in combination with anti-CD28 antibodies induced optimal activation.

Figure 21:
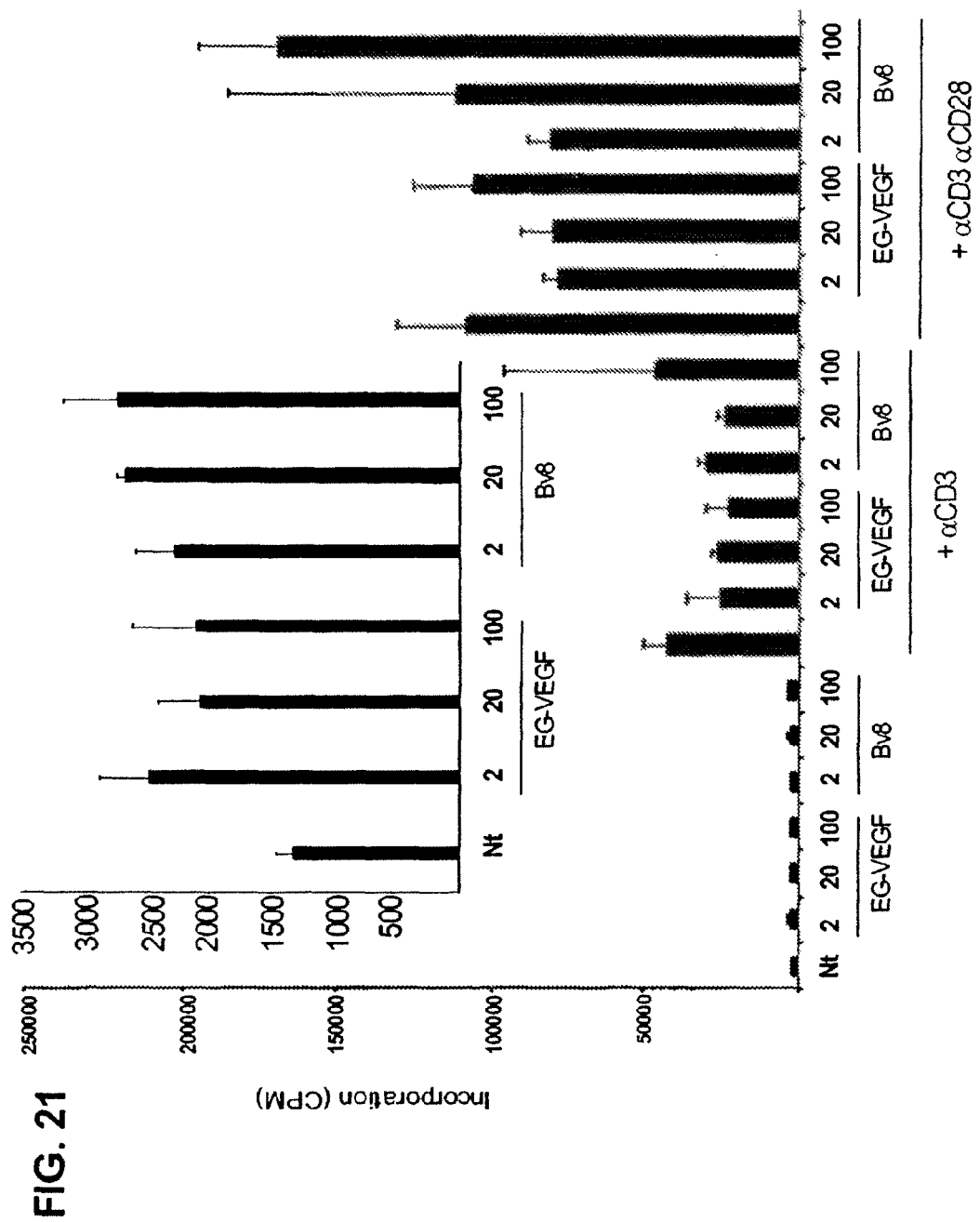
FIG. 21 is a graph showing that Bv8 and EG-VEGF increase 3H-thymidine incorporation in mouse CD4+ T lymphocytes ex vivo. The insert shows incorporation of 3H-thymidine in CD4+ T cells in the presence of increasing concentrations of EG-VEGF or Bv8.

As shown in FIGS. 21A and B, each of Bv8 and EG-VEGF induced a 5 to 8 fold increase in 3H-thymidine incorporation into T cells. This data indicates that Bv8 and EG-VEGF function as mitogens and potential survival factors for CD4+ T cells.

Example 7

Induction of Cytokine Production EG-VEGF in CD4+ T Cells

The ability of EG-VEGF to induce cytokine production in CD4+ T cells was studied. CD4+ T cells were isolated and purified as described above for Example 6. T Cell proliferation assays were performed as described above for Example 6. Recombinant EG-VEGF was added to each well at a concentration ranging from 2 to 200 nM. The wells were precoated for 2 hours at 37° C. with 0.5 μg/ml anti-mouse CD3 antibody (Pharmingen, La Jolla, Calif.) and/or 1μg/ml anti-mouse CD28 antibody (Pharmingen, La Jolla, Calif.) in carbonate buffer, pH 9.0. The antibodies crosslinked the respective receptors on the surface of the T cells, inducing basal activation. Addition of anti-CD3 antibodies in combination with anti-CD28 antibodies induced optimal activation. Prior to the incubation step, a 30 μl aliquot of the RPMI assay media was collected and replaced with an equal volume of fresh assay media. During the 72 hour incubation step, a 30 μl aliquot of the RPMI assay media was collected at 24 hour for analysis of cytokine production and replaced with an equal volume of fresh RPMI assay media. A second aliquot was collected immediately prior to the addition of $^3$H-thymidine. Analysis of the collected samples for IL-2 and IFN-γ was performed using the Luminex Multiplex Assay system (Luminex Corp., Austin, Tex.).

Cytokine production from CD4+ T cells was monitored following stimulation with EG-VEGF. Within 24 hours of ligand addition, EG-VEGF induced production of IL-2 (FIGS. 22A and B) and IFN-γ by the T cells (FIGS. 22C and D). The concentration of IFN-γ produced by the T cells after 72 hours of incubation with EG-VEGF exceeded the detection limits of the assay. These results indicate that Bv8 and EG-VEGF are capable of regulating the development of the CD4+ T cell response.

Example 8

Bv8 Promotes Recovery after 5-FU Myelosuppression

The ability of Bv8 to promote hematopoietic recovery after myelosuppression with 5-FU was studied. Recombinant adenoviruses were produced using the AdEasy vector system (Stratagene, La Jolla, Calif.). cDNA encoding an 81 amino acid isoform of mouse Bv8 (SEQ ID NO:6) or full-length human EG-VEGF (SEQ ID NO:8) were cloned into the multiple cloning site of the pCMV shuttle vector. Recombination and subsequent amplification in 293 cells was performed as recommended by the manufacturer. The virus was purified from the supernatant and cell pellet using the AAV purification kit (Virapur, San Diego, Calif.). Virus titers were determined by standard plaque assays utilizing CMV-LacZ virus as a control. Additional controls included receptor selective mutants of VEGF.

Control nude mice were injected with recombinant adenoviruses via the tail vein. The virus dose for each animal was $10^8$ pfu in 100 microlitres of phosphate buffered saline. Blood cell counts were monitored for 12 days following virus administration. Blood samples were obtained from orbital sinus bleeds of the mice and analyzed using the Cell Dyn automated hematology analyzer (Abbott Diagnostics, Santa Clara, Calif.). Differential counts were performed manually in conjunction with the automated analysis using light microscopy.

Test animals were injected with the recombinant adenovirus was administered to the mice 3 days prior to induction of myelosuppression. The virus dose for each animal was $10^8$ pfu in 100 microlitres of phosphate buffered saline. To induce myelosuppression in mice, a single dose of 125 mg/kg 5-fluorouracil (Adrucil, NDC 0013-1046-94) was injected in the peritoneum. Blood cell counts and differentials counts were measured 5, 10 and 14 days following administration of the 5-FU. Blood samples were obtained from orbital sinus bleeds of the mice and analyzed using the Cell Dyn automated hematology analyzer (Abbott Diagnostics, Santa Clara, Calif.). Differential counts were performed manually in conjunction with the automated analysis using light microscopy. At 14 days following the administration 5-FU, animals were sacrificed and the spleens excised. The spleens were weighed and then mechanically dissociated as described for Example 5. The spleen cellularity was measured by counting cells in the single cell suspension using a Coulter counter (Beckman Coulter, Miami, Fla.). $2 \times 10^4$ cells from each spleen were plated in triplicate in mouse complete Methocult (Stem Cell Technologies, Inc.) media and hematopoietic cell colony types were scored following 10-14 days in culture.

Figure 23D:
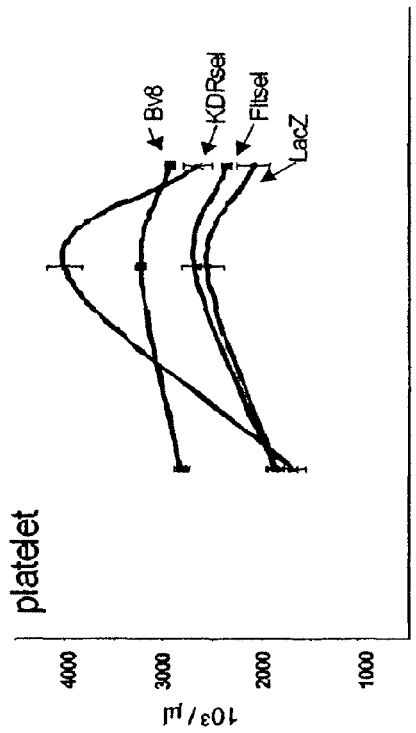
Figure 23E:
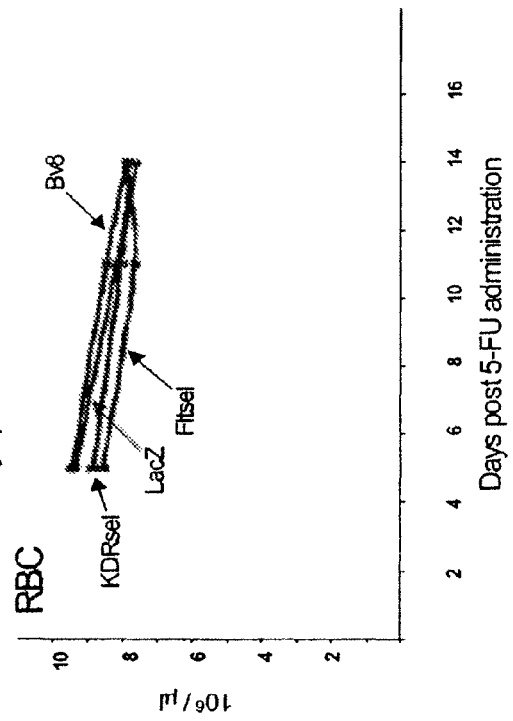
Figure 24:
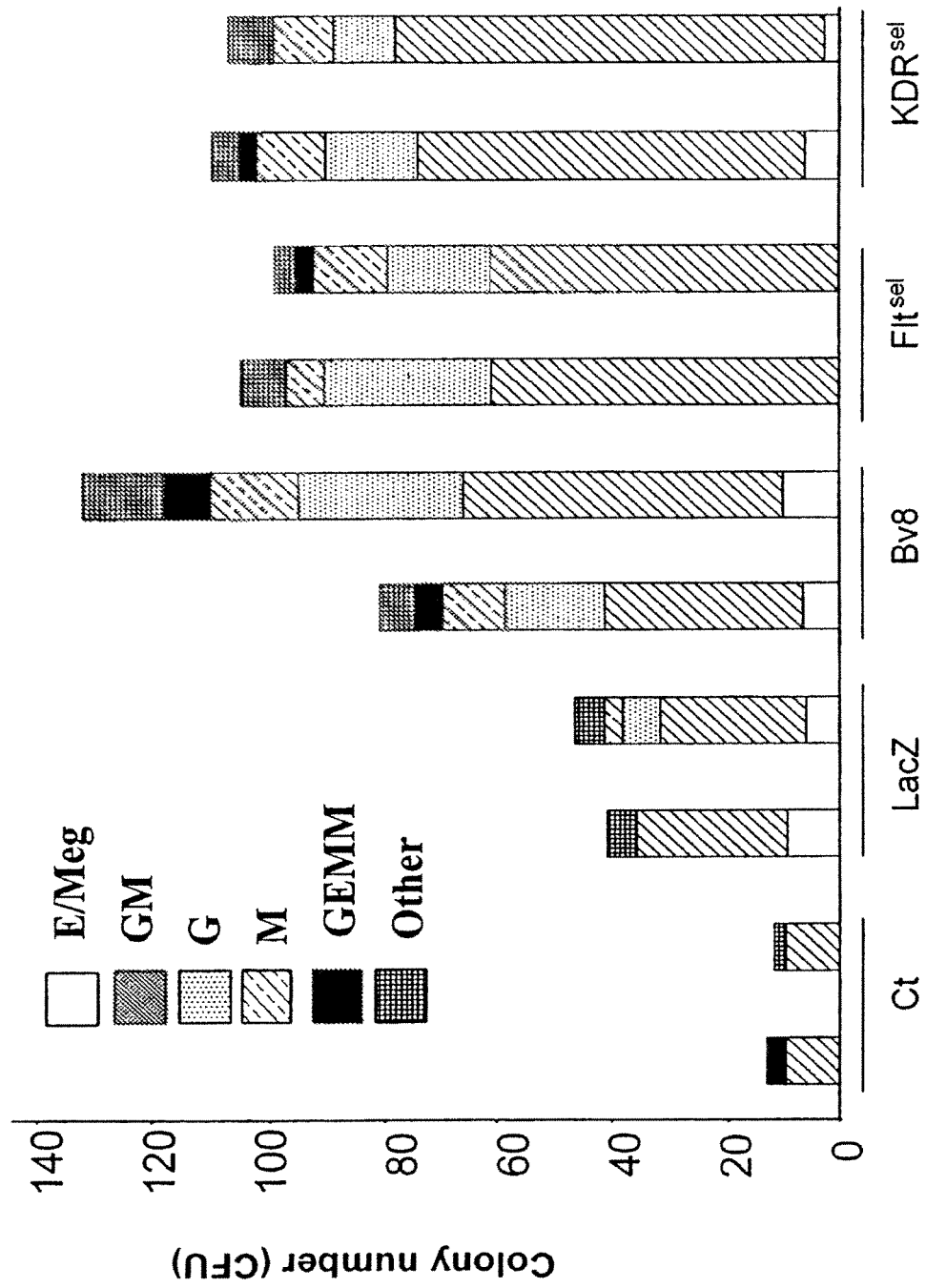
FIG. 24 is a graph showing spleen-derived committed mononuclear cell colony formation in vitro in the presence of various growth factors following myelosuppression with 5-FU. Spleen cells isolated from animals treated with Bv8 contained a significantly higher number of myeloid progenitor cells (CFU-GM) than the non-virus or LacZ treated control mice.

As shown in FIG. 23, the white blood cell counts in the Bv8 treatment group were significantly higher than other groups over the course of the study. Consistent with this data, granulocyte and monocyte numbers were also higher (FIGS. 23B and C). Spleen cellularity was significantly greater (at least 2.5-fold) in the Bv8 treated mice, than in control groups (FIG. 24). In addition, the Bv8 spleens contained a significantly higher number of progenitor cells than the non-virus or LacZ treated mice (FIG. 24).

The foregoing written specification is considered to be sufficient to enable one skilled in the art to practice the invention. However, various modifications of the invention in addition to those shown and described herein will be apparent to those skilled in the art from the foregoing description and fall within the scope of the appended claims.

We claim:

1. A method for inhibiting proliferation of lymphoid lineage progenitor cells or progeny thereof in a mammal, comprising administering to said mammal a Bv8 antagonist, or a combination of a Bv8 antagonist and an EG-VEGF antagonist, wherein the antagonist is an antibody or a binding fragment thereof, an antisense molecule, or a soluble receptor or a fragment thereof.

2. The method of claim 1, wherein said mammal is a human.

3. The method of claim 1, wherein the progeny are lymphoid precursor cells or lymphocytes.

4. The method of claim 3, wherein the lymphoid lineage progenitor cells or progeny thereof are T cells.

5. The method of claim 4, wherein the T cells are CD4+ T cells.

6. The method of claim 1, wherein the antibody is polyclonal, monoclonal, human, humanized or chimeric.

7. The method of claim 1, wherein the antibody is human monoclonal antibody or humanized monoclonal antibody.

8. The method of claim 1, wherein the antibody binding fragment s a Fab, Fab', F(ab')₂, or Fv fragment.

9. The method of claim 1, wherein the soluble receptor is Bv8/EG-VEGF receptor-1 or Bv8/EG-VEGF receptor-2.

10. A method for inhibiting proliferation of lymphoid lineage progenitor cells or progeny thereof, comprising contacting the lymphoid lineage progenitor cells or progeny thereof with a Bv8 antagonist or a combination of a Bv8 antagonist and an EG-VEGF antagonist, wherein the antagonist is an antibody or a binding fragment thereof, an antisense molecule, or a soluble receptor or a fragment thereof.

11. The method of claim 10, wherein the progeny are lymphoid precursor cells or lymphocytes.

12. The method of claim 10, wherein the lymphoid lineage progenitor cells or progeny thereof are T cells.

13. The method of claim 12, wherein the T cells are CD4+ T cells.

14. The method of claim 10, wherein the antibody is polyclonal, monoclonal, human, humanized or chimeric.

15. The method of claim 10, wherein the antibody is human monoclonal antibody or humanized monoclonal antibody.

16. The method of claim 10, wherein the antibody binding fragment is a Fab, Fab', F(ab')₂, or Fv fragment.

17. The method of claim 10, wherein the soluble receptor is Bv8/EG-VEGF receptor-1 or Bv8/EG-VEGF receptor-2.

18. The method of claim 10, wherein the Bv8 antagonist or the combination of the Bv8 antagonist and the EG-VEGF antagonist is administered to a human.

\* \* \* \* \*

SEQUENCE LISTING

```
<160> NUMBER OF SEQ ID NOS: 41

<210> SEQ ID NO 1
<211> LENGTH: 427
<212> TYPE: DNA
<213> ORGANISM: Artificial Sequence
<220> FEATURE:
<223> OTHER INFORMATION: cDNA encoding a human Bv8 homologue

<400> SEQUENCE: 1
tgagggcgcc atgaggagcc tgtgctgcgc cccactcctg ctcctcttgc tgctgccgcc      60
gctgctgctc acgccccgcg ctggggacgc cgccgtgatc accggggctt gtgacaagga     120
ctcccaatgt ggtggaggca tgtgctgtgc tgtcagtatc tgggtcaaga gcataaggat     180
ttgcacacct atgggcaaac tgggagacag ctgccatcca ctgactcgta aaacaatttt     240
tggaaatgga aggcaggaaa gaagaaagag gaagagaagc aaaaggaaaa aggaggttcc     300
attttttggg cggaggatgc atcacacttg cccatgtctg ccaggcttgg cctgtttacg     360
gacttcattt aaccgattta tttgtttagc ccaaaagtaa tcgctctgga gtagaaacca     420
aatgtga                                                              427

<210> SEQ ID NO 2
<211> LENGTH: 129
<212> TYPE: PRT
<213> ORGANISM: Homo sapiens
<220> FEATURE:
<223> OTHER INFORMATION: human Bv8 homologue

<400> SEQUENCE: 2

Met Arg Ser Leu Cys Cys Ala Pro Leu Leu Leu Leu Leu Leu Leu Pro
 1               5                  10                  15

Pro Leu Leu Leu Thr Pro Arg Ala Gly Asp Ala Ala Val Ile Thr Gly
             20                  25                  30

Ala Cys Asp Lys Asp Ser Gln Cys Gly Gly Met Cys Cys Ala Val
         35                  40                  45

Ser Ile Trp Val Lys Ser Ile Arg Ile Cys Thr Pro Met Gly Lys Leu
     50                  55                  60

Gly Asp Ser Cys His Pro Leu Thr Arg Lys Asn Asn Phe Gly Asn Gly
 65                  70                  75                  80

Arg Gln Glu Arg Lys Arg Lys Arg Ser Lys Arg Lys Lys Glu Val
             85                  90                  95

Pro Phe Phe Gly Arg Arg Met His His Thr Cys Pro Cys Leu Pro Gly
            100                 105                 110

Leu Ala Cys Leu Arg Thr Ser Phe Asn Arg Phe Ile Cys Leu Ala Gln
            115                 120                 125

Lys

<210> SEQ ID NO 3
<211> LENGTH: 423
<212> TYPE: DNA
<213> ORGANISM: Artificial Sequence
<220> FEATURE:
<223> OTHER INFORMATION: cDNA encoding human Bv8 homologue

<400> SEQUENCE: 3
```

```
tgagggcgcc atgaggagcc tgtgctgcgc cccactcctg ctcctcttgc tgctgccgcc      60
gagggcgcca tgaggagcct gtgctgcgcc ccactcctgc tcctcttgct gctgccgccg     120
ctgctgctca cgccccgcgc tggggacgcc gccgtgatca ccggggcttg tgacaaggac     180
tcccaatgtg gtgaggcat  gtgctgtgct gtcagtatct gggtcaagag cataaggatt     240
tgcacaccta tgggcaaact gggagacagc tgccatccac tgactcgtaa agttccattt     300
tttgggcgga ggatgcatca cacttgccca tgtctgccag gcttggcctg tttacggact     360
tcatttaacc gatttatttg tttagcccaa aagtaatcgc tctggagtag aaaccaaatg     420
tga                                                                  423

<210> SEQ ID NO 4
<211> LENGTH: 108
<212> TYPE: PRT
<213> ORGANISM: Homo sapiens
<220> FEATURE:
<223> OTHER INFORMATION: human Bv8 homologue

<400> SEQUENCE: 4

Met Arg Ser Leu Cys Cys Ala Pro Leu Leu Leu Leu Leu Leu Leu Pro
1               5                   10                  15

Pro Leu Leu Thr Pro Arg Ala Gly Asp Ala Ala Val Ile Thr Gly Ala
            20                  25                  30

Cys Asp Lys Asp Ser Gln Cys Gly Gly Met Cys Cys Ala Val Ser
        35                  40                  45

Ile Trp Val Lys Ser Ile Arg Ile Cys Thr Pro Met Gly Lys Leu
    50                  55                  60

Gly Asp Ser Cys His Pro Leu Thr Arg Lys Val Pro Phe Phe Gly Arg
65                  70                  75                  80

Arg Met His His Thr Cys Pro Cys Leu Pro Gly Leu Ala Cys Leu Arg
                85                  90                  95

Thr Ser Phe Asn Arg Phe Ile Cys Leu Ala Gln Lys
            100                 105

<210> SEQ ID NO 5
<211> LENGTH: 1338
<212> TYPE: DNA
<213> ORGANISM: Mus musculus
<220> FEATURE:
<223> OTHER INFORMATION: mouse Bv8 homologue

<400> SEQUENCE: 5
cggacgcgtg ggcgtcccct aaccgccacc gcgtccccgg gacgccatgg gggacccgcg      60
ctgtgccccg ctactgctac ttctgctgct accgctgctg ttcacaccgc ccgccgggga     120
tgccgcggtc atcaccgggg cttgcgacaa ggactctcag tgcggaggag gcatgtgctg     180
tgctgtcagt atctgggtta agagcataag gatctgcaca cctatgggcc aagtgggcga     240
cagctgccac cccctgactc ggaaagttcc attttggggg cggaggatgc accacacctg     300 ccctgcctg ccaggcttgg cgtgtttaag gacttctttc aaccggttta tttgcttggc      360
ccggaaatga tcactctgaa gtaggaactt gaaatgcgac cctccgctgc acaatgtccg     420
tcgagtctca cttgtaattg tggcaaacaa agaatactcc agaaagaaat gttctccccc     480
ttccttgact ttccaagtaa cgtttctatc tttgattttt gaagtggctt ttttttttt     540 ttttttttcc tttccttgaa ggaaagtttt gattttggg gagatttata gaggactttc      600
tgacatggct tctcatttcc ctgtttatgt tttgccttga catttttgaa tgccaataac     660
```

```
aactgttttc acaaatagga gaataagagg gaacaatctg ttgcagaaac ttccttttgc    720
cctttgcccc actcgcccg ccccgcccg cccgccctg cccatgcgca gacagacaca      780
cccttactct tcaaagactc tgatgatcct caccttactg tagcattgtg ggtttctaca   840
cttccccgcc ttgctggtgg acccactgag gaggctcaga gagctagcac tgtacaggtt   900
tgaaccagat cccccaagca gctcatttgg ggcagacgtt gggagcgctc caggaacttt   960
cctgcaccca tctggcccac tggctttcag ttctgctgtt taactggtgg gaggacaaaa   1020
ttaacgggac cctgaaggaa cctggcccgt ttatctagat ttgtttaagt aaaagacatt   1080
ttctccttgt tgtggaatat tacatgtctt tttctttttt atctgaagct tttttttttt   1140
ttctttaagt cttcttgttg gagacatttt aaagaacgcc actcgaggaa gcattgattt   1200
tcatytggca tgacaggagt catcatttta aaaaatcggt gttaagttat aatttaaact   1260
ttatttgtaa cccaaaggty taatgtaaat ggatttcctg atatcctgcc atttgtactg   1320
gtatcaatat ttytatgt                                                 1338
```

<210> SEQ ID NO 6
<211> LENGTH: 107
<212> TYPE: PRT
<213> ORGANISM: Mus musculus
<220> FEATURE:
<223> OTHER INFORMATION: mouse Bv8 homologue

<400> SEQUENCE: 6

```
Met Gly Asp Pro Arg Cys Ala Pro Leu Leu Leu Leu Leu Leu Pro
 1               5                  10                  15

Leu Leu Phe Thr Pro Pro Ala Gly Asp Ala Ala Val Ile Thr Gly Ala
            20                  25                  30

Cys Asp Lys Asp Ser Gln Cys Gly Gly Gly Met Cys Cys Ala Val Ser
        35                  40                  45

Ile Trp Val Lys Ser Ile Arg Ile Cys Thr Pro Met Gly Gln Val Gly
    50                  55                  60

Asp Ser Cys His Pro Leu Thr Arg Lys Val Pro Phe Trp Gly Arg Arg
65                  70                  75                  80

Met His His Thr Cys Pro Cys Leu Pro Gly Leu Ala Cys Leu Arg Thr
                85                  90                  95

Ser Phe Asn Arg Phe Ile Cys Leu Ala Arg Lys
            100                 105
```

<210> SEQ ID NO 7
<211> LENGTH: 1415
<212> TYPE: DNA
<213> ORGANISM: Artificial Sequence
<220> FEATURE:
<223> OTHER INFORMATION: cDNA encoding human native EG-VEGF

<400> SEQUENCE: 7

```
tggcctcccc agcttgccag gcacaaggct gagcgggagg aagcgagagg catctaagca    60
ggcagtgttt tgccttcacc ccaagtgacc atgagaggtg ccacgcgagt ctcaatcatg   120
ctcctcctag taactgtgtc tgactgtgct gtgatcacag gggcctgtga gcgggatgtc   180
cagtgtgggg caggcacctg ctgtgccatc agcctgtggc ttcgagggct gcggatgtgc   240 acccccgctgg ggcgggaagg cgaggagtgc accccggca gccacaaggt cccccttcttc   300 aggaaacgca agcaccacac ctgtcccttgc ttgcccaacc tgctgtgctc caggttcccg   360
gacggcaggt accgctgctc catggacttg aagaacatca atttttaggc gcttgcctgg   420
```

```
tctcaggata cccaccatcc ttttcctgag cacagcctgg attttatttt ctgccatgaa    480
acccagctcc catgactctc ccagtcccta cactgactac cctgatctct cttgtctagt    540
acgcacatat gcacacaggc agacatacct cccatcatga catggtcccc aggctggcct    600
gaggatgtca cagcttgagg ctgtggtgtg aaaggtggcc agcctggttc tcttccctgc    660
tcaggctgcc agagaggtgg taaatggcag aaaggacatt cccctcccc tccccaggtg    720 acctgctctc tttcctgggc cctgccctc tccccacatg tatccctcgg tctgaattag    780
acattcctgg gcacaggctc ttgggtgcat tgctcagagt cccaggtcct ggcctgaccc    840 tcaggcccctt cacgtgaggt ctgtgaggac caatttgtgg gtagttcatc ttccctcgat    900
tggttaactc cttagtttca gaccacagac tcaagattgg ctcttcccag agggcagcag    960
acagtcaccc caaggcaggt gtagggagcc cagggaggcc aatcagcccc ctgaagactc   1020
tggtcccagt cagcctgtgg cttgtggcct gtgacctgtg accttctgcc agaattgtca   1080
tgcctctgag gccccctctt accacacttt accagttaac cactgaagcc cccaattccc   1140
acagcttttc cattaaaatg caaatggtgg tggttcaatc taatctgata ttgacatatt   1200
agaaggcaat tagggtgttt ccttaaacaa ctcctttcca aggatcagcc ctgagagcag   1260
gttggtgact ttgaggaggg cagtcctctg tccagattgg ggtgggagca agggacaggg   1320
agcagggcag gggctgaaag gggcactgat tcagaccagg gaggcaacta cacaccaaca   1380
tgctggcttt agaataaaag caccaactga aaaaa                              1415
```

<210> SEQ ID NO 8
<211> LENGTH: 105
<212> TYPE: PRT
<213> ORGANISM: Homo sapiens
<220> FEATURE:
<223> OTHER INFORMATION: human native EG-VEGF popypeptide sequence

<400> SEQUENCE: 8

Met Arg Gly Ala Thr Arg Val Ser Ile Met Leu Leu Leu Val Thr Val
1               5                   10                  15

Ser Asp Cys Ala Val Ile Thr Gly Ala Cys Glu Arg Asp Val Gln Cys
            20                  25                  30

Gly Ala Gly Thr Cys Cys Ala Ile Ser Leu Trp Leu Arg Gly Leu Arg
        35                  40                  45

Met Cys Thr Pro Leu Gly Arg Glu Gly Glu Glu Cys His Pro Gly Ser
    50                  55                  60

His Lys Val Pro Phe Phe Arg Lys Arg Lys His His Thr Cys Pro Cys
65                  70                  75                  80

Leu Pro Asn Leu Leu Cys Ser Arg Phe Pro Asp Gly Arg Tyr Arg Cys
                85                  90                  95

Ser Met Asp Leu Lys Asn Ile Asn Phe
            100                 105

<210> SEQ ID NO 9
<211> LENGTH: 757
<212> TYPE: DNA
<213> ORGANISM: Artificial Sequence
<220> FEATURE:
<223> OTHER INFORMATION: cDNA encoding native mouse EG-VEGF

<400> SEQUENCE: 9

```
gaagtgaggg gtaccaaagt agactgtgtt tgtcgtcacc tcaagtgatc atgagaggcg     60
ctgtgcatat cttcatcatg ctccttctag caacggcgtc cgactgtgcg gtcatcacag    120
```

```
gggcctgtga acgagatatc cagtgtgggg ccggcacctg ctgcgctatc agtctgtggc    180
tgcggggcct gcggttgtgt accccactgg ggcgtgaagg agaggagtgc acccaggaa     240 gccacaagat ccccttcttg aggaaacgcc aacaccatac ctgtccctgc tcacccagcc   300
tgctgtgctc caggttcccg gacggcaggt accgctgctt ccgggacttg aagaataact   360
tttagtttgt ctggactctg tctggagcct gactgggtga cctcttgctt tacacctgtg   420
tgatttagct ccctgcaact tcgccattcc ccatcttgtc cgtgtatgtg cagacaggca   480
gaccttccgc tatggaatag ttcaccaggg tgcagagagg agttcgtggc cttgagaagt   540
tggccagccc gaccttcctg ctcagactg cctgaagttg tgacagtgtg ggccttctca    600
gttgcctgcc ccttcctgca tgtgcgcttc ttcctaaacc acactttct gggcactggc    660 ccatggatgc accactaaat caacaggtct gtggggtgga tgatcaactt tctctccatt   720
tttcttttat tgactggctt cctaatttaa ggactgt                             757
```

```
<210> SEQ ID NO 10
<211> LENGTH: 105
<212> TYPE: PRT
<213> ORGANISM: Mus musculus
<220> FEATURE:
<223> OTHER INFORMATION: EG-VEGF polypeptide sequence

<400> SEQUENCE: 10

Met Arg Gly Ala Val His Ile Phe Ile Met Leu Leu Leu Ala Thr Ala
 1               5                  10                  15

Ser Asp Cys Ala Val Ile Thr Gly Ala Cys Glu Arg Asp Ile Gln Cys
            20                  25                  30

Gly Ala Gly Thr Cys Cys Ala Ile Ser Leu Trp Leu Arg Gly Leu Arg
        35                  40                  45

Leu Cys Thr Pro Leu Gly Arg Glu Gly Glu Glu Cys His Pro Gly Ser
    50                  55                  60

His Lys Ile Pro Phe Leu Arg Lys Arg Gln His His Thr Cys Pro Cys
65                  70                  75                  80

Ser Pro Ser Leu Leu Cys Ser Arg Phe Pro Asp Gly Arg Tyr Arg Cys
                85                  90                  95

Phe Arg Asp Leu Lys Asn Ala Asn Phe
            100                 105
```

```
<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
tgggctacac tgagcaccag                                                20
```

```
<210> SEQ ID NO 12
<211> LENGTH: 20
<212> TYPE: DNA
<213> ORGANISM: Artificial Sequence
<220> FEATURE:
<223> OTHER INFORMATION: PCR primer

<400> SEQUENCE: 12
cagcgtcaaa ggtggaggag                                                20
```

```
<210> SEQ ID NO 13
```

```
<211> LENGTH: 28
<212> TYPE: DNA
<213> ORGANISM: Artificial Sequence
<220> FEATURE:
<223> OTHER INFORMATION: Probe

<400> SEQUENCE: 13
tggtctcctc tgacttcaac agcgacac                                              28

<210> SEQ ID NO 14
<211> LENGTH: 18
<212> TYPE: DNA
<213> ORGANISM: Artificial Sequence
<220> FEATURE:
<223> OTHER INFORMATION: PCR primer

<400> SEQUENCE: 14
ccattttttg ggcggagg                                                         18

<210> SEQ ID NO 15
<211> LENGTH: 19
<212> TYPE: DNA
<213> ORGANISM: Artificial Sequence
<220> FEATURE:
<223> OTHER INFORMATION: PCR primer

<400> SEQUENCE: 15
ccgtaaacag gccaagcct                                                        19

<210> SEQ ID NO 16
<211> LENGTH: 24
<212> TYPE: DNA
<213> ORGANISM: Artificial Sequence
<220> FEATURE:
<223> OTHER INFORMATION: Probe

<400> SEQUENCE: 16
tgcatcacac ttgcccatgt ctgc                                                  24

<210> SEQ ID NO 17
<211> LENGTH: 17
<212> TYPE: DNA
<213> ORGANISM: Artificial Sequence
<220> FEATURE:
<223> OTHER INFORMATION: PCR primer

<400> SEQUENCE: 17
ccggcagcca caaggtc                                                          17

<210> SEQ ID NO 18
<211> LENGTH: 18
<212> TYPE: DNA
<213> ORGANISM: Artificial Sequence
<220> FEATURE:
<223> OTHER INFORMATION: PCR primer

<400> SEQUENCE: 18
tgggcaagca aggacagg                                                         18

<210> SEQ ID NO 19
<211> LENGTH: 26
<212> TYPE: DNA
<213> ORGANISM: Artificial Sequence
<220> FEATURE:
<223> OTHER INFORMATION: probe

<400> SEQUENCE: 19
```
ccttcttcag gaaacgcaag caccac                                    26

<210> SEQ ID NO 20
<211> LENGTH: 17
<212> TYPE: DNA
<213> ORGANISM: Artificial Sequence
<220> FEATURE:
<223> OTHER INFORMATION: PCR primer

<400> SEQUENCE: 20
ggcgcccttc tacggct                                              17

<210> SEQ ID NO 21
<211> LENGTH: 20
<212> TYPE: DNA
<213> ORGANISM: Artificial Sequence
<220> FEATURE:
<223> OTHER INFORMATION: PCR primer

<400> SEQUENCE: 21
tctccttcac gaacacggtg                                           20

<210> SEQ ID NO 22
<211> LENGTH: 23
<212> TYPE: DNA
<213> ORGANISM: Artificial Sequence
<220> FEATURE:
<223> OTHER INFORMATION: Probe

<400> SEQUENCE: 22
caccatcgtg cgcgacttct tcc                                       23

<210> SEQ ID NO 23
<211> LENGTH: 23
<212> TYPE: DNA
<213> ORGANISM: Artificial Sequence
<220> FEATURE:
<223> OTHER INFORMATION: PCR primer

<400> SEQUENCE: 23
ggaaatgaca tctgtgttca tgc                                       23

<210> SEQ ID NO 24
<211> LENGTH: 25
<212> TYPE: DNA
<213> ORGANISM: Artificial Sequence
<220> FEATURE:
<223> OTHER INFORMATION: PCR primer

<400> SEQUENCE: 24
tcattgtatg ttacgacttt gcagc                                     25

<210> SEQ ID NO 25
<211> LENGTH: 21
<212> TYPE: DNA
<213> ORGANISM: Artificial Sequence
<220> FEATURE:
<223> OTHER INFORMATION: probe

<400> SEQUENCE: 25
cccgtgccct caagaagccg a                                         21

<210> SEQ ID NO 26
<211> LENGTH: 25
<212> TYPE: DNA

```
<213> ORGANISM: Artificial Sequence
<220> FEATURE:
<223> OTHER INFORMATION: PCR primer

<400> SEQUENCE: 26
atgttccagt atgactccac tcacg                                          25

<210> SEQ ID NO 27
<211> LENGTH: 25
<212> TYPE: DNA
<213> ORGANISM: Artificial Sequence
<220> FEATURE:
<223> OTHER INFORMATION: PCR primer

<400> SEQUENCE: 27
gaagacacca gtagactcca cgaca                                          25

<210> SEQ ID NO 28
<211> LENGTH: 29
<212> TYPE: DNA
<213> ORGANISM: Artificial Sequence
<220> FEATURE:
<223> OTHER INFORMATION: probe

<400> SEQUENCE: 28
aagcccatca ccatcttcca ggagcgaga                                      29

<210> SEQ ID NO 29
<211> LENGTH: 18
<212> TYPE: DNA
<213> ORGANISM: Artificial Sequence
<220> FEATURE:
<223> OTHER INFORMATION: PCR primer

<400> SEQUENCE: 29
cggaggatgc accacacc                                                  18

<210> SEQ ID NO 30
<211> LENGTH: 24
<212> TYPE: DNA
<213> ORGANISM: Artificial Sequence
<220> FEATURE:
<223> OTHER INFORMATION: PCR primer

<400> SEQUENCE: 30
ccggttgaaa gaagtcctta aaca                                           24

<210> SEQ ID NO 31
<211> LENGTH: 20
<212> TYPE: DNA
<213> ORGANISM: Artificial Sequence
<220> FEATURE:
<223> OTHER INFORMATION: probe

<400> SEQUENCE: 31
cccctgcctg ccaggcttgg                                                20

<210> SEQ ID NO 32
<211> LENGTH: 20
<212> TYPE: DNA
<213> ORGANISM: Artificial Sequence
<220> FEATURE:
<223> OTHER INFORMATION: PCR primer

<400> SEQUENCE: 32
tgaggaaacg ccaacaccat                                                20
```

<210> SEQ ID NO 33
<211> LENGTH: 17
<212> TYPE: DNA
<213> ORGANISM: Artificial Sequence
<220> FEATURE:
<223> OTHER INFORMATION: PCR primer

<400> SEQUENCE: 33
ccgggaacct ggagcac                                                    17

<210> SEQ ID NO 34
<211> LENGTH: 23
<212> TYPE: DNA
<213> ORGANISM: Artificial Sequence
<220> FEATURE:
<223> OTHER INFORMATION: PCR primer

<400> SEQUENCE: 34
cctgtccctg ctcacccagc ctg                                             23

<210> SEQ ID NO 35
<211> LENGTH: 19
<212> TYPE: DNA
<213> ORGANISM: Artificial Sequence
<220> FEATURE:
<223> OTHER INFORMATION: PCR primer

<400> SEQUENCE: 35
cagcgcacat gaagacttg                                                  19

<210> SEQ ID NO 36
<211> LENGTH: 21
<212> TYPE: DNA
<213> ORGANISM: Artificial Sequence
<220> FEATURE:
<223> OTHER INFORMATION: PCR primer

<400> SEQUENCE: 36
gtcatcttcg gtttcctgag t                                               21

<210> SEQ ID NO 37
<211> LENGTH: 20
<212> TYPE: DNA
<213> ORGANISM: Artificial Sequence
<220> FEATURE:
<223> OTHER INFORMATION: Probe

<400> SEQUENCE: 37
tccaggcagc acccctgatg                                                 20

<210> SEQ ID NO 38
<211> LENGTH: 18
<212> TYPE: DNA
<213> ORGANISM: Artificial Sequence
<220> FEATURE:
<223> OTHER INFORMATION: PCR primer

<400> SEQUENCE: 38
gaactccacg tgagcgca                                                   18

<210> SEQ ID NO 39
<211> LENGTH: 21
<212> TYPE: DNA
<213> ORGANISM: Artificial Sequence
<220> FEATURE:

```
<223> OTHER INFORMATION: PCR primer

<400> SEQUENCE: 39
gggtcccatg ttgatgatgc t                                         21

<210> SEQ ID NO 40
<211> LENGTH: 26
<212> TYPE: DNA
<213> ORGANISM: Artificial Sequence
<220> FEATURE:
<223> OTHER INFORMATION: probe

<400> SEQUENCE: 40
ctccctgata cacaccagcc cacctg                                    26

<210> SEQ ID NO 41
<211> LENGTH: 128
<212> TYPE: PRT
<213> ORGANISM: Mus musculus
<220> FEATURE:
<223> OTHER INFORMATION: Mouse Bv8 homologue

<400> SEQUENCE: 41

Met Gly Asp Pro Arg Cys Ala Pro Leu Leu Leu Leu Leu Leu Leu Pro
 1               5                  10                  15

Leu Leu Phe Thr Pro Pro Ala Gly Asp Ala Ala Val Ile Thr Gly Ala
            20                  25                  30

Cys Asp Lys Asp Ser Gln Cys Gly Gly Gly Met Cys Cys Ala Val Ser
        35                  40                  45

Ile Trp Val Lys Ser Ile Arg Ile Cys Thr Pro Met Gly Gln Val Gly
    50                  55                  60

Asp Ser Cys His Pro Leu Thr Arg Lys Ser His Val Ala Asn Gly Arg
 65                 70                  75                  80

Gln Glu Arg Arg Arg Ala Lys Arg Arg Lys Lys Glu Val Pro
                85                  90                  95

Phe Trp Gly Arg Arg Met His His Thr Cys Pro Cys Leu Pro Gly Leu
            100                 105                 110

Ala Cys Leu Arg Thr Ser Phe Asn Arg Phe Ile Cys Leu Ala Arg Lys
            115                 120                 125
```